United States Patent
Jiao et al.

(10) Patent No.: US 7,230,008 B2
(45) Date of Patent: Jun. 12, 2007

(54) TETRAHYDROPYRANYL CYCLOPENTYL TETRAHYDROPYRIDOPYRIDINE MODULATORS OF CHEMOKINE RECEPTOR ACTIVITY

(75) Inventors: Richard Jiao, Collingswood, NJ (US); Gabor Butora, Martinsville, NJ (US); Stephen D. Goble, Edison, NJ (US); Deodialsingh Guiadeen, Linden, NJ (US); Sander G. Mills, Scotch Plains, NJ (US); Gregori Morriello, Randolph, NJ (US); Alexander Pasternak, Princeton, NJ (US); Cheng Tang, East Brunswick, NJ (US); Lihu Yang, Edison, NJ (US); Changyou Zhou, Plainsboro, NJ (US); Shankaran Kothandaraman, Kendall Park, NJ (US); Christopher Moyes, Hertford (GB)

(73) Assignee: Merck & Co, Inc., Rahway, NJ (US)

( * ) Notice: Subject to any disclaimer, the term of this patent is extended or adjusted under 35 U.S.C. 154(b) by 52 days.

(21) Appl. No.: 10/923,594

(22) Filed: Aug. 20, 2004

(65) Prior Publication Data

US 2005/0107422 A1 May 19, 2005

Related U.S. Application Data

(63) Continuation-in-part of application No. 10/425,167, filed on Apr. 29, 2003, now Pat. No. 6,812,234.

(60) Provisional application No. 60/376,180, filed on Apr. 29, 2002.

(51) Int. Cl.
*A61K 31/47* (2006.01)
*C07D 471/02* (2006.01)

(52) U.S. Cl. ..................... 514/300; 546/113; 546/122

(58) Field of Classification Search ................ 514/300; 546/113, 122
See application file for complete search history.

(56) References Cited

U.S. PATENT DOCUMENTS

| | | | |
|---|---|---|---|
| 3,647,804 | A | 3/1972 | Rynbrandt et al. |
| 3,772,308 | A | 11/1973 | Pioch et al. |
| 2002/0012664 | A1 | 1/2002 | LaRosa |

OTHER PUBLICATIONS

Liang et al., Species Selectivity of a Small Molecule Antagonist for the CCR1 Chemokine Receptor, EUR. J. of Pharmacol, 389:41-49 (2000).*
Sarau et al., Characterization of Functional chemokine Receptors (CCR1 and CCR2) on EoL-3 Cells: A Model System to Examine the Role of Chemokines in Cell Function, J. Parm. Exp. Ther., 283(1):411-418 (1997).*

Ferie & Diaz-Gonzalez, The CCR2 Receptor as a Therapeutic Target, Expert Opin. Ther. Patents, 16:1 (2006).*
Israel et al., The Many Roles of Chemokines and Chemokine Receptors in Inflammation, New Eng. J. of Med., 354:6 610-621 (2006).*
Grainger & Reckless, Broad-spectrum Chemokine Inhibitors (BSCIs) and their Anti-inflammatory Effects in vivo, Biochemical Pharmacology 65:1027-1034 (2003).*
Aiello, Arterioscler Thromb Vac Biol., vol. 19, pp. 1518-1525, 1999.*
Dawson, Atherosclerosis, vol. 143, pp. 205-211, 1999.*
Egashira, Circ Res., vol. 90, pp. 1167-1172, 2002.*
R. Horuk, Trends in Pharm. Sci., 15:159-165(1994).
O. Mitsunobu, Synthesis, 1:1-28(1981).
H.K. Deng et al., Nature, 381: 661-666(1996).
A.J. Mancuso et al., J. Org. Chem., 43:2480-2482(1978).
J.P. Depres et al., J. Org. Chem., 49: 928-931(1984).
K. Neote et al., Cell, 72:415-425(1993).
J.J. Gomez-Reino et al., Arthritis & Rheumatism, 42:989-992(1999).
S.Y. Sung et al., Arch. Pharm. Pharm. Med. Chem., 329:291-300(1996).
K.S. Warmington et al., Am. J. Path., 154:1407-1416(1999).
T. Kurihara et al., J. Exp. Med., 186:1757-1762(1997).
B. Lu et al., J. Exp. Med., 187:601-608(1998).
L. Boring et al., J. Clin. Inves., 100:2552-2561(1997).
B. J. Rollins, Blood, 90:909-928(1997).

(Continued)

*Primary Examiner*—D. Margaret Seaman
(74) *Attorney, Agent, or Firm*—William Krovatin; David Rubin

(57) ABSTRACT

The present invention is directed to methods for treating, preventing, ameliorating, controlling or reducing the risk of an inflammatory or immunoregulatory disorder or disease, which method comprises the administration to a patient of an effective amount of the compound of formula I:

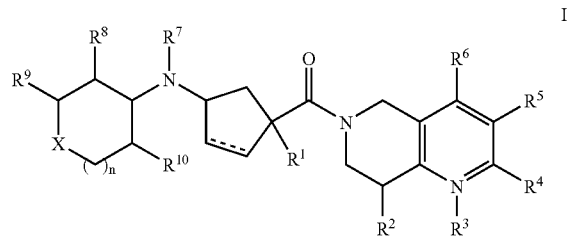

(wherein $R^1$, $R^2$, $R^3$, $R^4$, $R^5$, $R^6$, $R^7$, $R^8$, $R^9$, $R^{10}$, X, n and the dashed line are defined herein) which are useful as modulators of chemokine receptor activity. In particular, these compounds are useful as modulators of the chemokine receptor CCR-2.

12 Claims, No Drawings

OTHER PUBLICATIONS

M. Samson et al., Biochemistry, 35:3362-3367(1996).
A.D. Luster, New Eng. J. Med., 338:436-445(1998).
R. M. Burk et al., Tetrahedron Lett., 34:975-978(1993).
S.W. Wright et al., Tetrahedron Lett., 38:7345-7348(1997).
W.A. Kuziel et al., Proc. Natl. Acad. Sci. USA, 94:12053-12058(1997).
H. Kita et al., J. Exp. Med., 183:2421-2426(1996).
B.M. Trost et al., J. Am. Chem. Soc., 105:2315-2325(1983).
A. Chaudhuri et al., J. Bio. Chem., 269:7835-7838(1994).
P.M. Murphy, Annu. Rev. Immunol., 12:593-633(1994).
T.J. Schall, Cytokine, 3:165-183(1991).
H. Stetter et al., Liebigs Ann. Chem., 944-949(1979).
L. Boring, et al., Nature, 394:894-897(1998).
Sarau, et al., J. Pharm. Exp. Therapeutics, vol. 283 (1997), No. 1, pp. 411-418.
Liang, et al., Eur. Journal of Pharmacology, vol. 389 (2000), pp. 41-49.

* cited by examiner

TETRAHYDROPYRANYL CYCLOPENTYL TETRAHYDROPYRIDOPYRIDINE MODULATORS OF CHEMOKINE RECEPTOR ACTIVITY

CROSS REFERENCE TO RELATED APPLICATIONS

This application is a continuation-in-part of U.S. application Ser. No. 10/425,167 filed Apr. 29, 2003, now U.S. Pat. No. 6,812,234 issued Nov. 2, 2004, which claims the benefit, under 35 U.S.C. § 119 (e), of U.S. Provisional Application Ser. No. 60/376,180 filed Apr. 29, 2002.

BACKGROUND OF THE INVENTION

The chemokines are a family of small (70–120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature*, 381, 661–666 (1996)).

The chemokines are secreted by a wide variety of cell types and bind to specific G-protein coupled receptors (GPCRs) (reviewed in Horuk, *Trends Pharm. Sci.*, 15, 159–165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/"CKR-2A" or "CC-CKR-2A"/ "CC-CKR-2A") [MCP-1, MCP-2, MCP-3, MCP4]; CCR-3 (or "CKR-3" or "CC-CKR-3") [Eotaxin, Eotaxin 2, RANTES, MCP-2, MCP-3] (Rollins, et al., *Blood*, 90, 908–928 (1997)); CCR-4 (or "CKR-4" or "CC-CKR-4") [MIP-1α, RANTES, MCP-1] (Rollins, et al., *Blood*, 90, 908–928 (1997)); CCR-5 (or "CKR-5" or "CC-CKR-5") [MIP-1α, RANTES, MIP-1β] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989–992 (1999)). A review of the role of eosinophils in allergic inflammation is provided by Kita, H., et al., *J. Exp. Med.* 183, 2421–2426 (1996). A general review of the role of chemokines in allergic inflammation is provided by Lustger, A. D., *New England J. Med.*, 338(7), 426–445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.*, 187, 601–608 (1998); Kurihara et al. *J. Exp. Med.*, 186, 1757–1762 (1997); Boring et al. *J. Clin. Invest.*, 100, 2552–2561 (1997); Kuziel et al. *Proc. Natl. Acad. Sci.*, 94, 12053–12058 (1997)). Furthermore, these animals show reduced monocyte infiltration into granulomatous lesions induced by the injection of schistosomal or mycobacterial antigens (Boring et al. *J. Clin. Invest.*, 100, 2552–2561 (1997); Warmington et al. *Am J. Path.*, 154, 1407–1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1 −/− or CCR2 −/− mice backcrossed to APO-E −/−, LDL-R −/− or Apo B transgenic mice maintained on high fat diets (Boring et al. *Nature*, 394, 894–897 (1998); Gosling et al. *J. Clin. Invest.*, 103, 773–778 (1999)). Thus, CCR2 antagonists may inhibit atherosclerotic lesion formation and pathological progression by impairing monocyte recruitment and differentiation in the arterial wall.

SUMMARY OF THE INVENTION

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of the formula I:

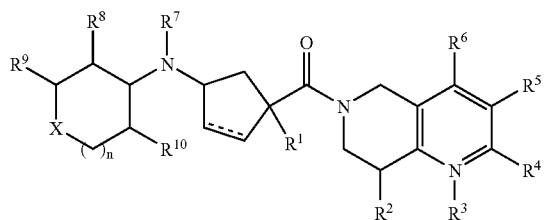

I wherein:

X is selected from the group consisting of:
—O—, —$NR^{20}$—, —S—, —SO—, —$SO_2$—, and —$CR^{21}R^{22}$—, —$NSO_2R^{20}$—, —$NCOR^{20}$—, —$NCO_2R^{20}$—, —$CR^{21}CO_2R^{20}$—, —$CR^{21}OCOR^{20}$—, —CO—, where $R^{20}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl, where $R^{21}$ and $R^{22}$ are independently selected from: hydrogen, hydroxy,
$C_{1-6}$ alkyl, —O—$C_{1-6}$alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl;

$R^1$ is selected from:
—$C_{1-6}$alkyl, —$C_{0-6}$alkyl-O—$C_{1-6}$alkyl-, —$C_{0-6}$alkyl-S—$C_{1-6}$alkyl-, —($C_{0-6}$alkyl)-($C_{3-7}$cycloalkyl)-($C_{0-6}$alkyl), hydroxy, -heterocycle, —CN, —$NR^{20}R^{26}$, —$NHSO_2R^{20}$, —$NHCOR^{20}$, —$NHCO_2R^{20}$, —$CO_2R^{20}$, —$CR^{21}CO_2R^{20}$, —$CR^{21}OCOR^{20}$ and phenyl,
where $R^{26}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —$CO_2H$, —$CO_2$—$C_{1-6}$ alkyl, and trifluoromethyl
where the alkyl and the cycloalkyl are unsubstituted or substituted with 1–7 substituents where the substituents are independently selected from:
(a) halo,
(b) hydroxy,
(c) —O—C1–3alkyl,
(d) trifluoromethyl,
(f) C1–3alkyl,
(g) —O—C1–3alkyl,
(h) —CO2R20,
(i) —SO2R20,
(j) —NHCOCH3,
(k) —NHSO2CH3,
(l) -heterocycle,
(m) =O,
(n) —CN,
and where the phenyl and pyridyl are unsubstituted or substituted with 1–3 substituents where the substituents are independently selected from: halo, hydroxy, $C_{1-3}$alkyl, $C_{1-3}$alkoxy and trifluoromethyl;

$R^2$ is selected from:
(a) hydrogen,
(b) hydroxy,
(c) halo,
(d) $C_{1-3}$alkyl, where the alkyl is unsubstituted or substituted with 1–6 substituents independently selected from: fluoro, and hydroxy,
(e) —$NR^{20}R^{26}$,
(f) —$CO_2R^{20}$,
(g) —$CONR^{20}R^{26}$,
(h) —$NR^{20}COR^{21}$,
(i) —$OCONR^{20}R^{26}$,
(j) —$NR^{20}CONR^{20}R^{26}$,
(k) -heterocycle,
(l) —CN,
(m) —$NR^{20}$—$SO_2$—$NR^{20}R^{26}$,
(n) —$NR^{20}$—$SO_2$—$R^{26}$,
(o) —$SO_2$—$NR^{20}R^{26}$ and
(p) =O, where $R^2$ is connected to the ring via a double bond;

$R^3$ is oxygen or is absent;

$R^4$ is selected from:
(a) hydrogen,
(b) $C_{1-6}$alkyl,
(c) trifluoromethyl,
(d) trifluoromethoxy,
(e) chloro,
(f) fluoro,
(g) bromo, and
(h) phenyl;

$R^5$ is selected from:
(a) $C_{1-6}$alkyl, where alkyl may be unsubstituted or substituted with 1–6 fluoro and optionally substituted with hydroxyl,
(b) —O—$C_{1-6}$alkyl, where alkyl may be unsubstituted or substituted with 1–6 fluoro,
(c) —CO—$C_{1-6}$alkyl, where alkyl may be unsubstituted or substituted with 1–6 fluoro,
(d) —S—$C_{1-6}$alkyl, where alkyl may be unsubstituted or substituted with 1–6 fluoro, (e) -pyridyl, which may be unsubstituted or substituted with one or more substituents selected from the group consisting of: halo, trifluoromethyl, $C_{1-4}$alkyl, and $CO_2R^{20}$,
(f) fluoro,
(g) chloro,
(h) bromo,
(i) —$C_{4-6}$cycloalkyl,
(j) —O—$C_{4-6}$cycloalkyl,
(k) phenyl, which may be unsubstituted or substituted with one or more substituents selected from the group consisting of: halo, trifluoromethyl, $C_{1-4}$alkyl, and $CO_2R^{20}$,
(l) —O-phenyl, which may be unsubstituted or substituted with one or more substituents selected from the group consisting of: halo, trifluoromethyl, $C_{1-4}$alkyl, and $CO_2R^{20}$,
(m) —$C_{3-6}$cycloalkyl, where alkyl may be unsubstituted or substituted with 1–6 fluoro,
(n) —O—$C_{3-6}$cycloalkyl, where alkyl may be unsubstituted or substituted with 1–6 fluoro,
(o) -heterocycle,
(p) —CN, and
(q) —$CO_2R^{20}$;

$R^6$ is selected from:
(a) hydrogen,
(b) C1–6alkyl, and
(c) trifluoromethyl
(d) fluoro
(e) chloro, and
(f) bromo;

$R^7$ is selected from:
(a) hydrogen, and
(b) $C_{1-6}$alkyl, which is unsubstituted or substituted with 1–3 substituents where the substituents are independently selected from: halo, hydroxy, —$CO_2H$, —$CO_2C_{1-6}$alkyl, and —O—$C_{1-3}$alkyl;

$R^8$ is selected from:
(a) hydrogen,
(b) $C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
(c) fluoro,
(d) —O—$C_{1-3}$alkyl, where alkyl may be unsubstituted or substituted with 1–3 fluoro, and
(e) $C_{3-6}$ cycloalkyl,
(f) —O—$C_{3-6}$cycloalkyl,
(g) hydroxy,
(h) —$CO_2R^{20}$,
(i) —$OCOR^{20}$,
or $R^7$ and $R^8$ may be joined together via a $C_{2-4}$alkyl or a $C_{0-2}$alkyl-O—$C_{1-3}$alkyl chain to form a 5–7 membered ring;

$R^9$ is selected from:
(a) hydrogen,
(b) $C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
(c) $CO_2R^{20}$,
(d) hydroxy, and
(e) —O—$C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$, or $R^8$ and $R^9$ may be joined together by a $C_{1-4}$alkyl chain or a $C_{0-3}$alkyl-O—$C_{0-3}$alkyl chain to form a 3–6 membered ring;

$R^{10}$ is selected from:
(a) hydrogen, and
(b) $C_{1-6}$alkyl, where alkyl may be unsubstituted or substituted with 1–6 fluoro,
(c) fluoro,
(d) —O—$C_{3-6}$cycloalkyl, and
(e) —O—$C_{1-3}$alkyl, where alkyl may be unsubstituted or substituted with 1–6 fluoro,
or $R^8$ and $R^{10}$ may be joined together by a $C_{2-3}$alkyl chain to form a 5–6 membered ring, where the alkyl are unsubstituted or substituted with 1–3 substituents where the substituents are independently selected from: halo, hydroxy, —$CO_2R^{20}$, $C_{1-3}$alkyl, and $C_{1-3}$alkoxy,
or $R^8$ and $R^{10}$ may be joined together by a $C_{1-2}$alkyl-O—$C_{1-2}$alkyl chain to form a 6–8 membered ring, where the alkyl are unsubstituted or substituted with 1–3 substituents where the substituents are independently selected from: halo, hydroxy, —$CO_2R^{20}$, $C_{1-3}$alkyl, and $C_{1-3}$alkoxy, or $R^8$ and $R^{10}$ may be joined together by a —O—$C_{1-2}$alkyl-O-chain to form a 6–7 membered ring, where the alkyl are unsubstituted or substituted with 1–3 substituents where the substituents are independently selected from: halo, hydroxy, —$CO_2R^{20}$, $C_{1-3}$alkyl, and $C_{1-3}$alkoxy;

n is selected from 0, 1 and 2;
the dashed line represents a single or a double bond;
and pharmaceutically acceptable salts thereof and individual diastereomers thereof.

Preferred compounds of the present invention include those of formula Ia:

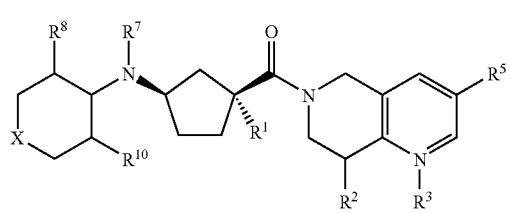

Ia wherein $R^1$, $R^2$, $R^3$, $R^5$, $R^7$, $R^8$, $R^{10}$ and X are defined herein, and pharmaceutically acceptable salts and individual diastereomers thereof.

More preferred compounds of the present invention also include those of formula Ib:

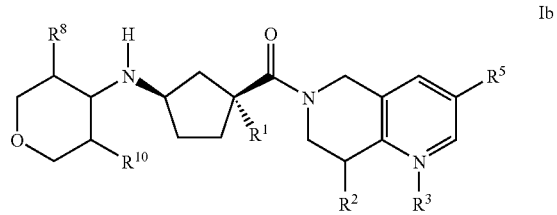

Ib wherein $R^1$, $R^2$, $R^3$, $R^5$, $R^8$ and $R^{10}$ are defined herein, and pharmaceutically acceptable salts and individual diastereomers thereof.

Even more preferred compounds of the present invention also include those of formula Ic:

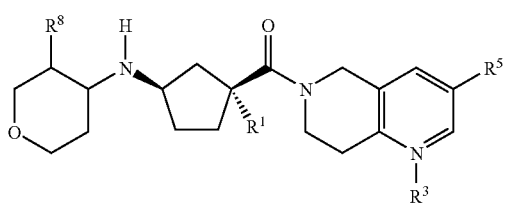

Ic wherein $R^1$, $R^3$, $R^5$ and $R^8$ are defined herein.

Still more preferred compounds of the present invention also include those of formula Id:

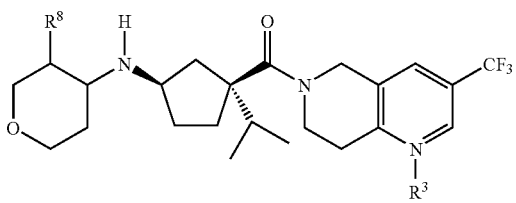

Id wherein $R^3$ and $R^8$ are defined herein and pharmaceutically acceptable salts and individual diastereomers thereof.

In the present invention it is preferred that X is selected from the group consisting of: —O—, —CH$_2$—, —S—, —SO—, and —SO$_2$—.

In the present invention it is more preferred that X is selected from the group consisting of: —O—, and —CH$_2$—.

In the present invention it is even more preferred that X is —O—.

In the present invention it is preferred that $R^1$ is selected from:
  (1) —C$_{1-6}$alkyl, which is unsubstituted or substituted with 1–6 substituents where the substituents are independently selected from:
    (a) halo,
    (b) hydroxy,
    (c) —O—C1–3alkyl, and
    (d) trifluoromethyl,
  (2) —C$_{0-6}$alkyl-O—C$_{1-6}$alkyl-, which is unsubstituted or substituted with 1–6 substituents where the substituents are independently selected from:
    (a) halo, and
    (b) trifluoromethyl,
  (3) —C$_{0-6}$alkyl-S—C$_{1-6}$alkyl-, which is unsubstituted or substituted with 1–6 substituents where the substituents are independently selected from:
    (a) halo, and
    (b) trifluoromethyl,
  (4) —(C$_{3-5}$cycloalkyl)-(C$_{0-6}$alkyl), which is unsubstituted or substituted with 1–7 substituents where the substituents are independently selected from:
    (a) halo,
    (b) hydroxy,
    (c) —O—C$_{1-3}$alkyl, and
    (d) trifluoromethyl.

In the present invention it is more preferred that $R^1$ is C$_{1-6}$alkyl which is unsubstituted or substituted with 1–5 substituents where the substituents are independently selected from:
  (a) hydroxy, and
  (b) fluoro.

In the present invention it is even more preferred that $R^1$ is selected from:
  (a) isopropyl,
  (b) —CH(OH)CH$_3$, and
  (c) —CH$_2$CF$_3$.

In the present invention it is still more preferred that $R^1$ is isopropyl.

In the present invention it is preferred that $R^2$ is selected from:
  (a) hydrogen,
  (b) hydroxy,
  (c) —NH$_2$,
  (d) —CO$_2$H,
  (e) -triazolyl,
  (f) -tetrazolyl,
  (g) —CO$_2$—C$_{1-6}$alkyl,
  (h) —CONH$_2$,
  (i) —CONH—C$_{1-6}$alkyl,
  (j) —NHCO—C$_{1-6}$alkyl,
  (k) —NHCONH$_2$,
  (l) —NHCONH—C$_{1-6}$alkyl
  (m) —OCONH—C$_{1-6}$alkyl,
  (n) —NH—SO$_2$—C$_{1-6}$alkyl, and
  (o) —SO$_2$—NH—C$_{1-6}$alkyl.

In the present invention it is more preferred that $R^2$ is selected from:
  (a) hydrogen,
  (b) hydroxy,
  (c) —NH$_2$,
  (d) —CO$_2$H,
  (e) -triazolyl,
  (f) -tetrazolyl,
  (g) —NHCOCH$_3$,
  (h) —NHCONH$_2$,
  (i) —CONH$_2$,
  (j) —NH—SO$_2$—CH$_3$, and
  (k) —SO$_2$—NH—CH$_3$.

In the present invention it is even more preferred that $R^2$ is hydrogen.

In the present invention it is preferred that $R^4$ is selected from:
  (a) hydrogen, and
  (b) trifluoromethyl.

In the present invention it is more preferred that $R^4$ is hydrogen.

In the present invention it is preferred that $R^5$ is selected from:
  (a) C$_{1-3}$alkyl substituted with 1–6 fluoro,
  (b) chloro,
  (c) bromo,
  (d) —O-phenyl, which may be unsubstituted or substituted with one or more substituents selected from the group consisting of: halo and trifluoromethyl,
  (e) phenyl, which may be unsubstituted or substituted with one or more substituents selected from the group consisting of: halo and trifluoromethyl, and
  (f) —O—C$_{1-3}$alkyl substituted with 1–6 fluoro.

In the present invention it is more preferred that $R^5$ is selected from:
  (a) trifluoromethyl,
  (b) trifluoromethoxy, (c) bromo, and
(d) chloro.

In the present invention it is most preferred that $R^5$ is trifluoromethyl.

In the present invention it is preferred that $R^6$ is hydrogen.

In the present invention it is preferred that $R^7$ is hydrogen or methyl.

In the present invention it is preferred that $R^8$ is selected from:
(a) hydrogen,
(b) $C_{1-3}$alkyl, which is unsubstituted or substituted with 1–6 fluoro,
(c) —O—$C_{1-3}$alkyl, and
(d) fluoro, and
(e) hydroxy.

In the present invention it is more preferred that $R^8$ is selected from:
(a) hydrogen,
(b) trifluoromethyl,
(c) methyl,
(d) methoxy,
(e) ethoxy,
(f) ethyl,
(g) fluoro, and
(h) hydroxy.

In the present invention it is preferred that $R^9$ is hydrogen.

In the present invention it is preferred that $R^{10}$ is selected from:
(a) hydrogen,
(b) methyl, and
(c) methoxy.

In the present invention it is preferred that $R^{10}$ is hydrogen.

In the present invention it is also preferred that $R^8$ and $R^{10}$ are joined together by a —$CH_2CH_2$— chain or a —$CH_2CH_2CH_2$— chain to form a cyclopentyl ring or a cyclohexyl ring.

In the present invention it is preferred that n is 1.

Representative compounds of the present invention include those presented in the Examples and pharmaceutically acceptable salts and individual diastereomers thereof.

The compounds of the instant invention have at least two asymmetric centers at the 1- and 3-positions of the cyclopentyl ring and one asymmetric center at the 4-position of the ring bearing X. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of the more preferred compounds of this orientation, where the substituents on the cyclopentyl ring (amide and amine units) are cis, as depicted:

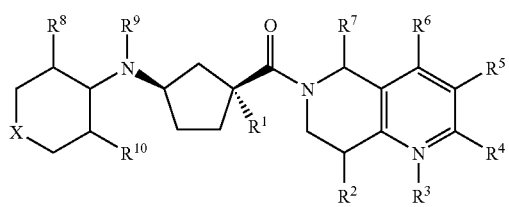

The absolute configurations of the most preferred compounds of this invention are those of the orientation as depicted:

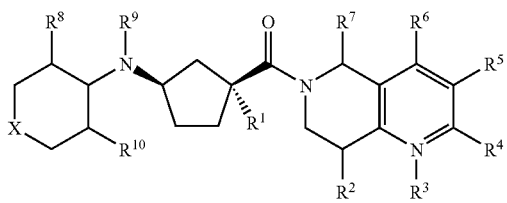

wherein the carbon bearing the amine substituent is designated as being of the (R) absolute configuration and the carbon bearing the amide subunit can be designated as being of either the (S) or (R) absolute configuration depending on the priority for $R^1$. For example if R is isopropyl then the absolute stereochemistry at the carbon bearing the amide subunit would be (S) since the amide and amine units are preferred to have the cis arrangement on the cyclopentyl ring.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$alkyl is defined to identify the group as having 1, 2, 3, 4, 5, 6, 7 or 8 carbons in a linear or branched arrangement, such that $C_{1-8}$alkyl specifically includes methyl, ethyl, n-propyl, iso-propyl, n-butyl, iso-butyl, tert-butyl, pentyl, hexyl, heptyl and octyl. Likewise, $C_0$, as in $C_0$alkyl is defined to identify the presence of a direct covalent bond. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA or 0.5% human serum) and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1 \times 10^7$ cells/ml. Cells were fluorescently labeled in the dark with 2 µM Calcien-AM (Molecular Probes), for 30 min at 37° C. Labeled cells were washed twice and suspended at $5 \times 10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant.

In particular, the compounds of the following examples had activity in binding to the CCR-2 receptor in the aforementioned assays, generally with an $IC_{50}$ of less than about 1 µM. Such a result is indicative of the intrinsic activity of the compounds in use as modulators of chemokine receptor activity.

Mammalian chemokine receptors provide a target for interfering with or promoting eosinophil and/or leukocyte function in a mammal, such as a human. Compounds which inhibit or promote chemokine receptor function, are particularly useful for modulating eosinophil and/or leukocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis, and further, chronic obstructive pulmonary disease, and multiple schlerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In a certain embodiment, the disease or condition is one in which the actions of leukocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersentitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; and cancers, including cancers with leukocyte infiltration of the skin or organs and other cancers. Inhibitors of chemokine receptor function may also be useful in the treatment and prevention of stroke (Hughes et al., *Journal of Cerebral Blood Flow & Metabolism*, 22:308–317, 2002, and Takami et al., *Journal of Cerebral Blood Flow & Metabolism*, 22:780–784, 2002), neurodegenerative conditions including but not limited to Alzheimer's disease, amyotrophic lateral sclerosis (ALS) and Parkinson's disease, obesity, type II diabetes, neuropathic and inflammatory pain, and Guillain Barre syndrome. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis and chronic obstructive pulmonary disease.

Diseases or conditions of humans or other species, which can be treated with modulators of chemokine receptor function, include or involve but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (Trichuriasis, Enterobiasis, Ascariasis, Hookworm, Strongyloidiasis, Trichinosis, filariasis), trematodes (flukes) (Schistosomiasis, Clonorchiasis), cestodes (tape worms) (Echinococcosis, Taeniasis saginata, Cysticercosis), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*).

In addition, treatment of the aforementioned inflammatory, allergic, infectious and autoimmune diseases can also be contemplated for agonists of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis, psoriatic arthritis and multiple schlerosis.

In another aspect, the instant invention may be used to evaluate putative specific agonists or antagonists of chemokine receptors, including CCR-2. Accordingly, the present invention is directed to the use of these compounds in the preparation and execution of screening assays for compounds that modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a further aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, for instance a human being, male or female, in whom modulation of chemokine receptor activity is desired. "Modulation" as used herein is intended to encompass antagonism, agonism, partial antagonism, inverse agonism and/or partial agonism. In an aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and multiple sclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, biological TNF sequestrants, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with CCR2 antagonists, such as the CCR2 antagonists compounds of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin, EDG receptor agonists including FTY-720, and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as $\beta$2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106, 203), leukotriene biosynthesis inhibitors (zileuton, BAY-1005); (f) non-steroidal antiinflammatory agents (NSAIDs) such as propionic acid derivatives (alimoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3, CXCR4 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) anti-diabetic agents such as insulin, sulfonylureas, biguanides (metformin), $\alpha$-glucosidase inhibitors (acarbose) and glitazones (troglitazone and pioglitazone); (l) preparations of interferon beta (interferon beta-1$\alpha$, interferon beta-1$\beta$); (m) preparations of glatiramer acetate; (n) preparations of CTLA4Ig; (o) preparations of hydroxychloroquine, (p) Copaxone® and (q)

other compounds such as 5-aminosalicylic acid and prodrugs thereof, antimetabolites such as azathioprine, 6-mercaptopurine and methotrexate, leflunomide, teriflunomide, and cytotoxic and other cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin.

The oily suspensions may contain a thickening agent, for example beeswax, hard paraffin or cetyl The oily suspensions may contain a thickening agent, for example beeswax, hard paraffin or cetyl a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the parenterally-acceptable diluent or solvent, for example as a solution in 1,3-butane diol. Among the chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.0001 to 500 mg per kg patient body weight per day which can be administered in single or multiple doses. In certain embodiments the dosage level will be about 0.0005 to about 400 mg/kg per day; or from about 0.005 to about 300 mg/kg per day; or from about 0.01 to about 250 mg/kg per day, or from about 0.05 to about 100 mg/kg per day, or from about 0.5 to about 50 mg/kg per day. Within this range the dosage may be 0.0001 to 0.005, 0.005 to 0.05, 0.05 to 0.5, 0.5 to 5 or 5 to 50 mg/kg per day. For oral administration, the compositions may be provided in the form of tablets containing 0.01 to 1000 milligrams of the active ingredient, or 0.1 to 500, 1.0 to 400, or 2.0 to 300, or 3.0 to 200, particularly 0.01, 0.05, 0.1, 4, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, or once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made by known procedures or as illustrated.

Several methods for preparing the compounds of this invention are illustrated in the following Schemes and Examples. Starting materials are either commercially available or made by known procedures in the literature or as illustrated. The present invention further provides processes for the preparation of compounds of the formula I as defined above, which comprises many different sequences of assembling compounds of formula (II), formula (III), and formula (IV), or compounds of formula (V), formula (VI), and formula (IV), or compounds of formula (VII) and formula (IV).

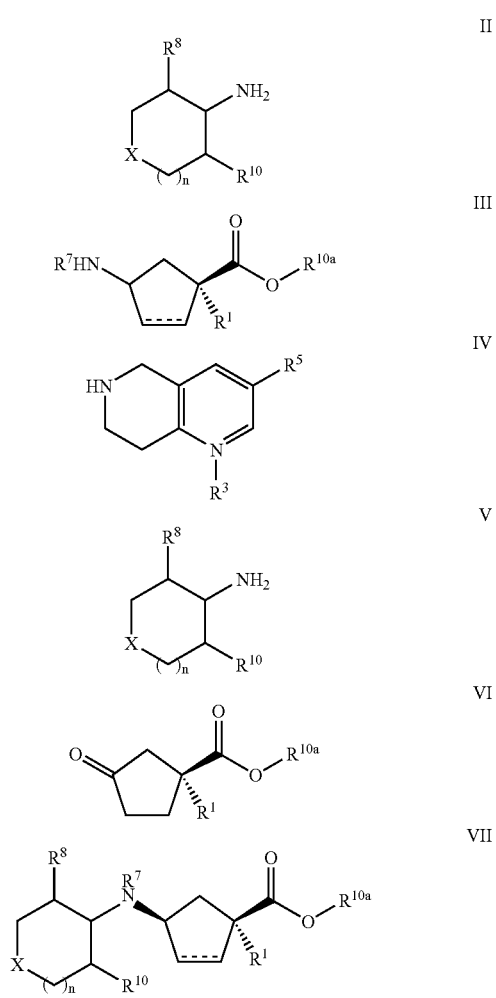

wherein $R^1$, $R^3$, $R^5$, $R^8$, $R^{10}$, and X are defined as in formula I, and $R^{10a}$ represents either a hydrogen or an alkyl group such as methyl, ethyl, t-butyl, or benzyl which serves as a protecting group, $R^7$ represent either hydrogen or an amine protecting group (Greene, T; Wuts, P. G. M. *Protective Groups in Organic Synthesis*, John Wiley & Sons, Inc., New York, N.Y. 1991) such as Boc or trifluoroacetate. The bond between the two carbon atoms where a dashed line is shown in formula III and in formula VII represent either a single or double bond as defined in formula I.

One general way of constructing target compounds I utilizing Intermediates of the formulas II, III, and IV is illustrated in Scheme 1. Coupling of the acid IIIa and the amine IV under standard amide bond formation reaction conditions such as PyBrop in the presence of a base such as N,N-diisopropylethylamine and a catalyst such as DMAP gives the intermediate 1-1. Removal of the Boc protecting group yields the amine 1-2. Reductive alkylation of 1-2 with ketones II in the presence of a borohydride such as sodium triacetoxyborohydride or sodium cyanoborohydride then provides the compound of formula Ia. Note that when $R^8$ or $R^{10}$ are other than hydrogen, a mixture of diastereomers (Eliel, E. E., Wilen, S. H., *Stereochemistry of Organic Compounds*, John Wiley & Sons, Inc., New York) results from the reductive amination step. These can be separated into their components by chromatography using normal phase, reverse phase or chiral columns, depending on the nature of the separation. Compound Ia can be further elaborated to the compound of the formula I by reductive alkylation with an aldehyde or by alkylation with, for example, an alkyl halide.

SCHEME 1

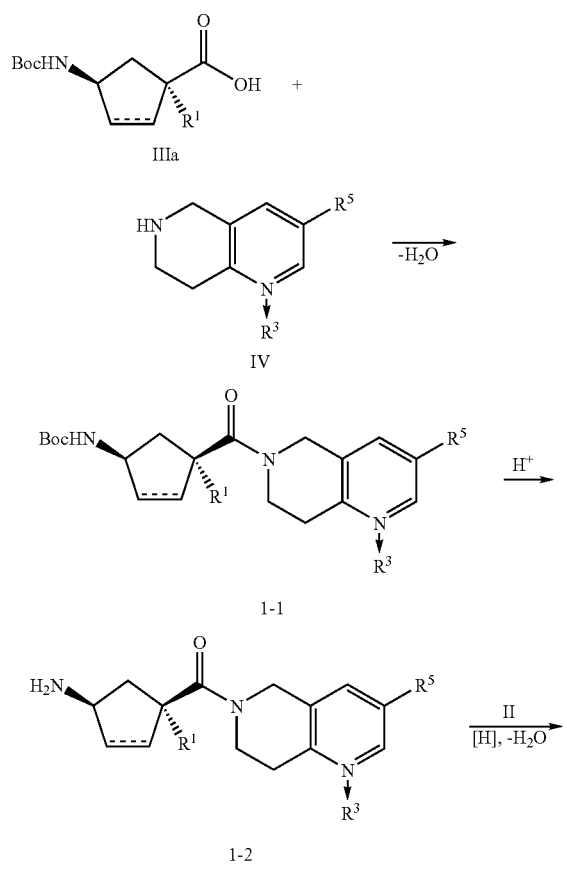

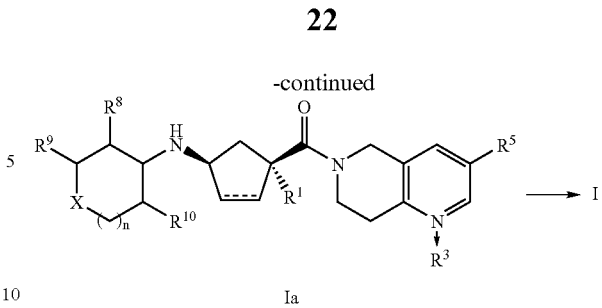

In some cases Intermediate 1-1 may require modification prior to elaboration to 1-2. For example (see below) oxidation of the 5-azatetrahydroisoquinoline moiety (where $R^3$ in 1-1 is nothing) to its N-oxide (where $R^3$=O) may be conveniently performed at this stage to give 1-1a. This can be accomplished with a variety of oxidants including mCPBA. Compound 1-1a can be carried on in the same fashion as 1-1 in Scheme 1 to give Ia.

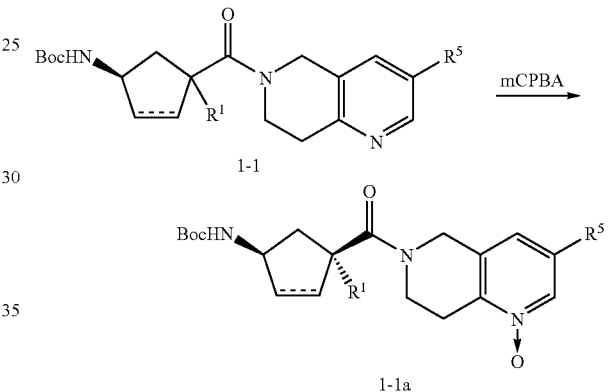

An alternative sequence of construction involving fragments of the formulas II, III, and IV is depicted in Scheme 1A. Amine IIIb is reductively alkylated with ketone II in the presence of a borohydride such as sodium triacetoxyborohydride or sodium cyanoborohydride to give secondary amine 1-3. Protection of the amine group can be accomplished using any of a number of protecting groups, including the trifluoroacetamide group ($R^{12}$=COCF$_3$), which can be installed by treatment with trifluoroacetic anhydride in the presence of a base such as triethylamine. The ester functionality of the resulting compound 1-4 is then cleaved using conditions that are dependent upon the nature of $R^{10a}$. For example, a benzyl ester is cleaved by hydrogenolysis using a catalyst such as Pd on carbon to give the fragment of the formula VII. Coupling of the acid VII and the amine IV under standard amide bond formation reaction conditions such as PyBrop in the presence of a base such as N,N-diisopropylethylamine and a catalyst such as DMAP gives the intermediate 1-5. Alternatively, the acid VII can be converted to its corresponding acid chloride and then treated with amine IV in the presence of a base such as triethylamine to give 1-5. Removal of the protecting group ($R^{12}$) to give compound Ia can be achieved in various ways depending upon the nature of the protecting group. For example the trifluoroacetate group can be removed by treatment with excess sodium borohydride, or by treatment with a base such as lithium hydroxide.

SCHEME 1A

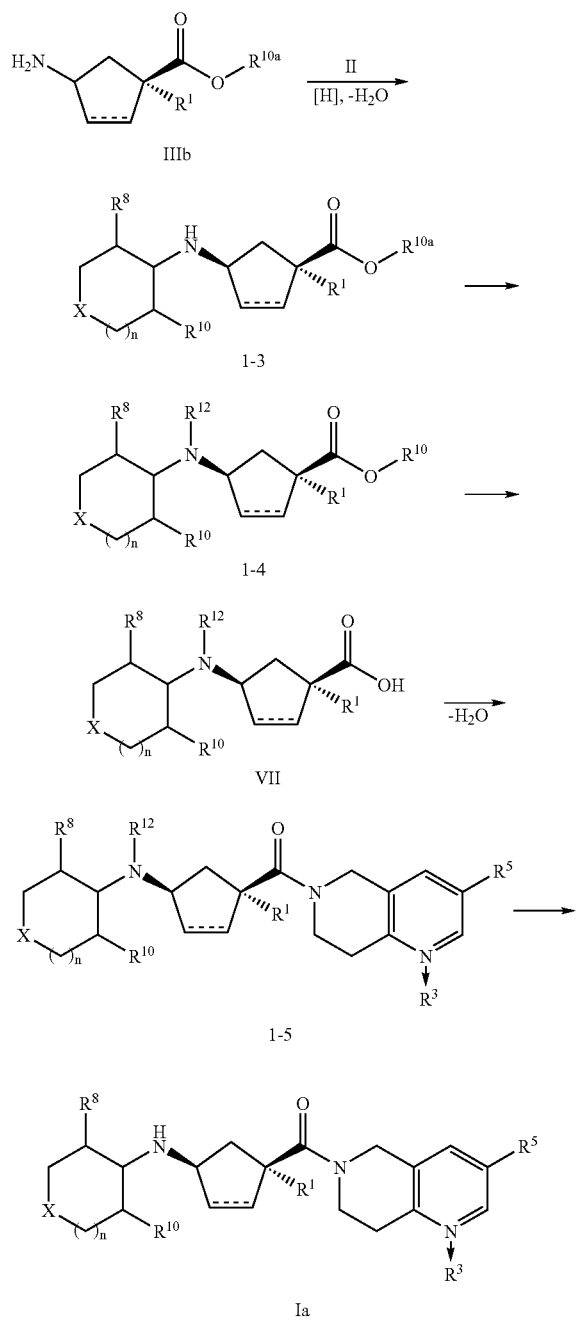

Alternatively, Intermediate 1-3 from Scheme 1A can be more directly accessed as shown in Scheme 1B. In this case amine IIIc is reductively alkylated with ketone II in the presence of a borohydride such as sodium triacetoxyborohydride or sodium cyanoborohydride to give secondary amine 1-3a. Treatment with a base such as LDA then generates the enolate of 1-3a which can be alkylated with 1-3a. Treatment with a base such as LDA then generates the enolate of 1-3a which can be alkylated with compound 1-3 can be carried on to compounds of the formula I or Ia, using the same steps as outlined in Scheme 1A.

SCHEME 1B

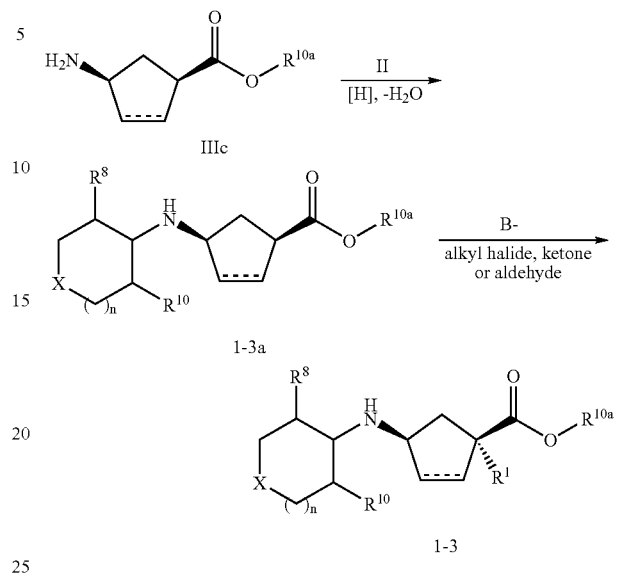

In addition to assembly according to Schemes 1, and 1A–1B, compounds of the formula I can be prepared using Intermediates of the formula IV, V and VII (Scheme 2). According to this protocol, known keto acid VIa is simultaneously converted to dimethyl acetal-ester VIb using trimethylorthoformate, methanol and an acid catalyst such as toluene sulfonic acid. Alkylation of 2-1 can be carried out with a base such as LDA and an electrophile such as an alkyl halide to give 2-2. Hydrolysis of the methyl ester and removal of the dimethyl acetal protecting group can be accomplished by treatment with a base such as NaOH, followed by an acid such as HCl. The resulting acid VIb can be coupled to amine IV using various conditions. For example acid VIb can be converted to its corresponding acid chloride with oxalyl chloride and catalytic DMF, then treated with amine IV. The amide 2-3 can be resolved using chiral HPLC to give a single enantiomer 2-3a. Reductive amination of 2-3a with amine V using, for example, NaB(OAc)$_3$H gives target compound Ia, which can, if appropriate, be further modified to compounds I as shown in Scheme 1. Note that the compound Ia formed in the above mentioned transformation was obtained initially as a mixture of 1,3-cis- and 1,3-trans-diastereoisomers. ways, including by preparative TLC, column chromatography, and chiral HPLC to provide the preferred 1,3-cis-isomer Ia shown.

SCHEME 2

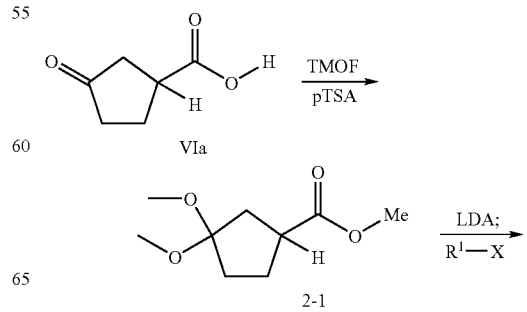

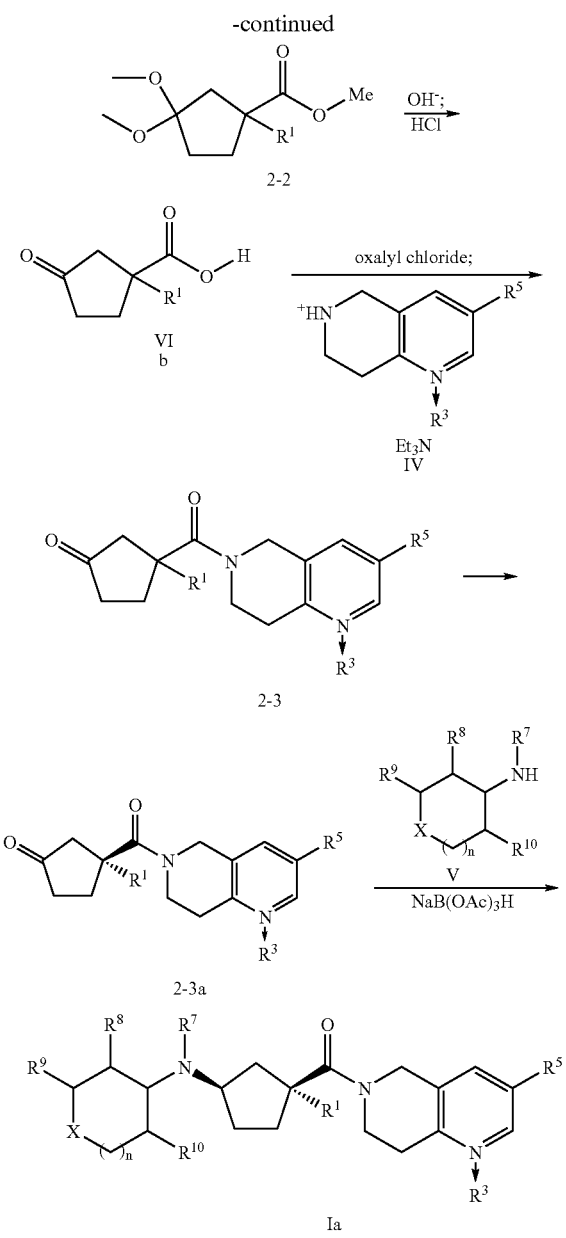

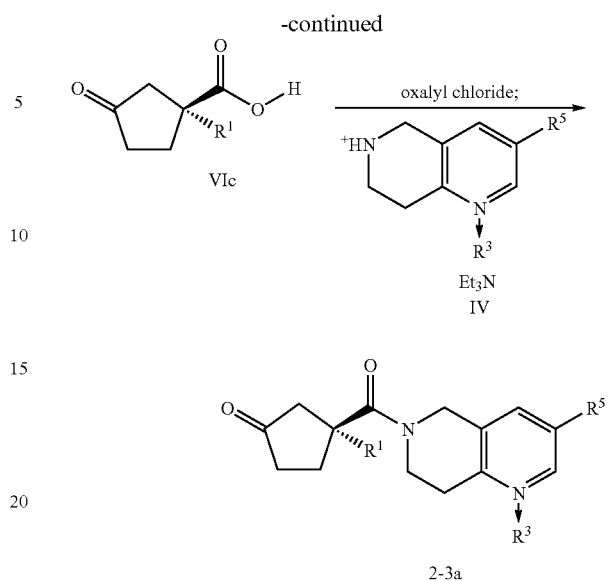

The cyclopentane core fragment m can be prepared in a number of ways. One of those is depicted in Scheme 3, 3a, and 3b. According to Scheme 3, the commercially available homochiral lactam 3-1 is hydrogenated and the saturated 3-2 is streated with di-tert-butyl dicarboante in the presence of a suitable catalyst, e.g. N,N-dimethylamino pyridine. A base catalyzed cleavage of the amide bond in the presence of a suitable alcohol $R^{10a}$—OH then provides the respective ester IIIe. The BOC-protecting group is removed, preferably with an acid such as HCl in a aprotic solvent, such as dioxane, to yield the amine IIIf in the form of a salt. When this amine is mixed with benzophenone imine, the respective Schiff base IIIg is formed, which can be obtained in pure form by simple filtration to remove ammonium chloride.

An alternate route to homochiral 2-3a involves oxidation of aminoacid IIId as shown in Scheme 2A. This transformation can be accomplished using NBS as the oxidant. The resulting keto acid VIc is obtained as a single enantiomer in this way, which can then be carried on to Intermediate 2-3a, and ultimately to compound Ia and I, as shown in Scheme 2.

SCHEME 3

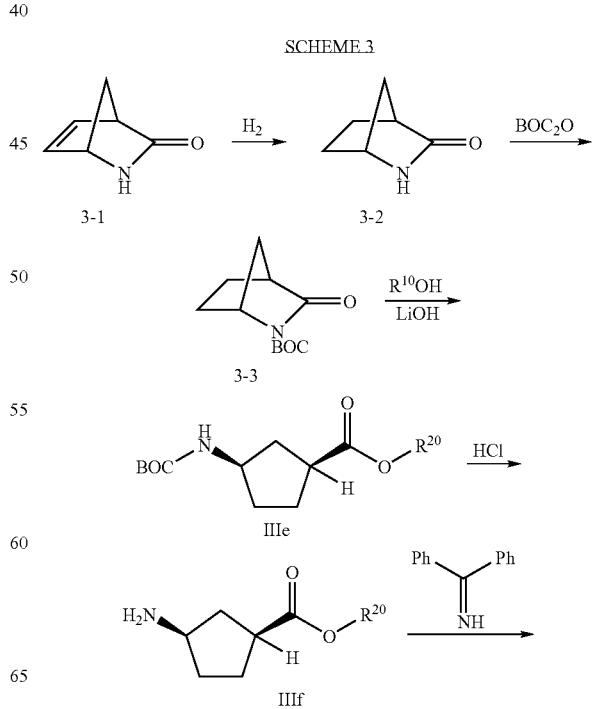

SCHEME 2A

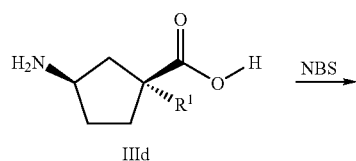

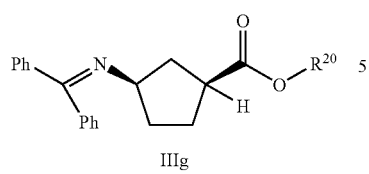

IIIg

The enolate formed from ester IIIg with a strong base, such as LDA can be reacted with alkyl halides $R^1$—X, as well as aldehydes $R^{1a}$CHO or ketones $R^{1a}R^{2a}$CO to obtain intermediates IIIh, 3-4 and IIIi, 3-5 respectively, Scheme 3A. These reactions produce a mixture of the respective cis- (IIIh and IIIi) and trans-(3-4 and 3-5) diastereoisomers, which can be separated by a suitable chromatography. In most cases, normal phase flash chromatography on deactivated silica gel can be applied with success.

SCHEME 3A

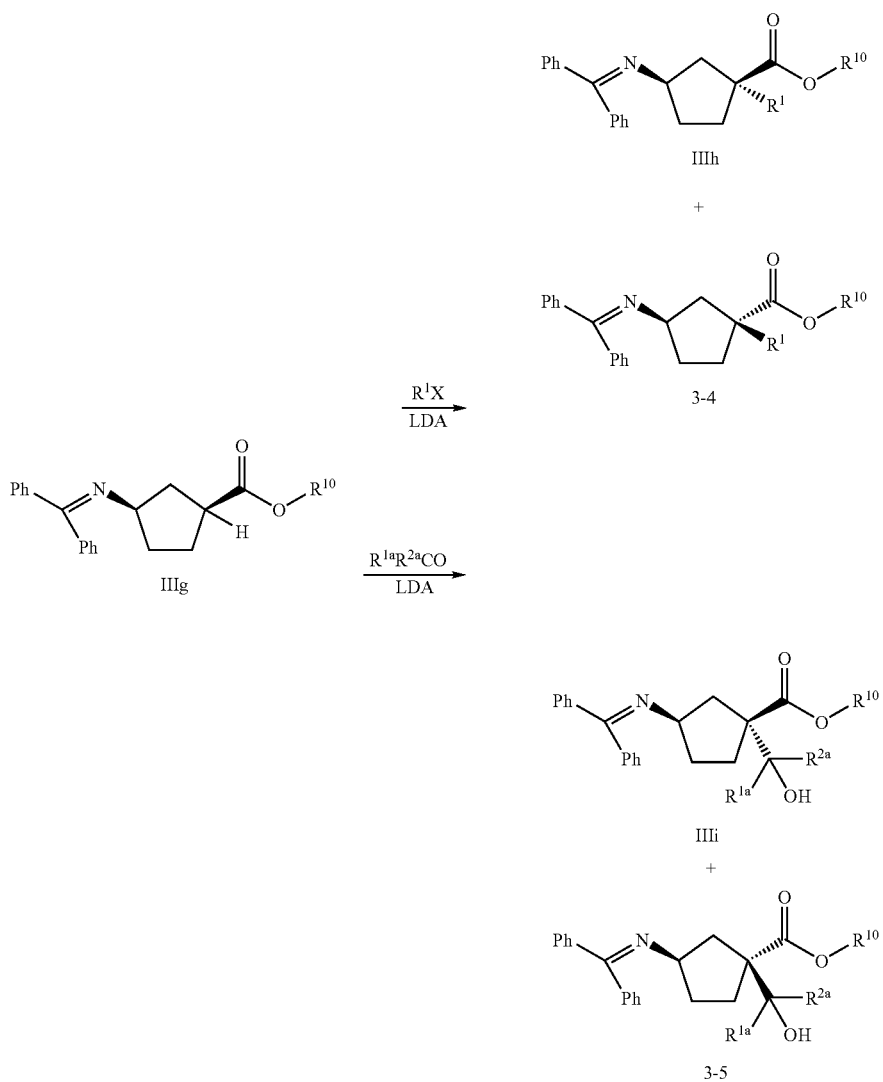

The desired cis diastereoisomers IIIh and IIIi are then treated with an acid such as HCl to aid hydrolysis of the imine group and the resulting amino group IIIj can be suitably protected e.g. in a form of a tert-butoxycarbonyl amide (Scheme 3B). The ester group present in intermediates IIIk can then be cleaved to give acid IIIl. The applied procedure depends on the nature of the ester: e.g. a benzyl ester can be cleaved by hydrogenolysis, a tert-butyl ester under acidic conditions and a alkyl ester can be hydrolyzed under either acidic or basic conditions.

SCHEME 3B

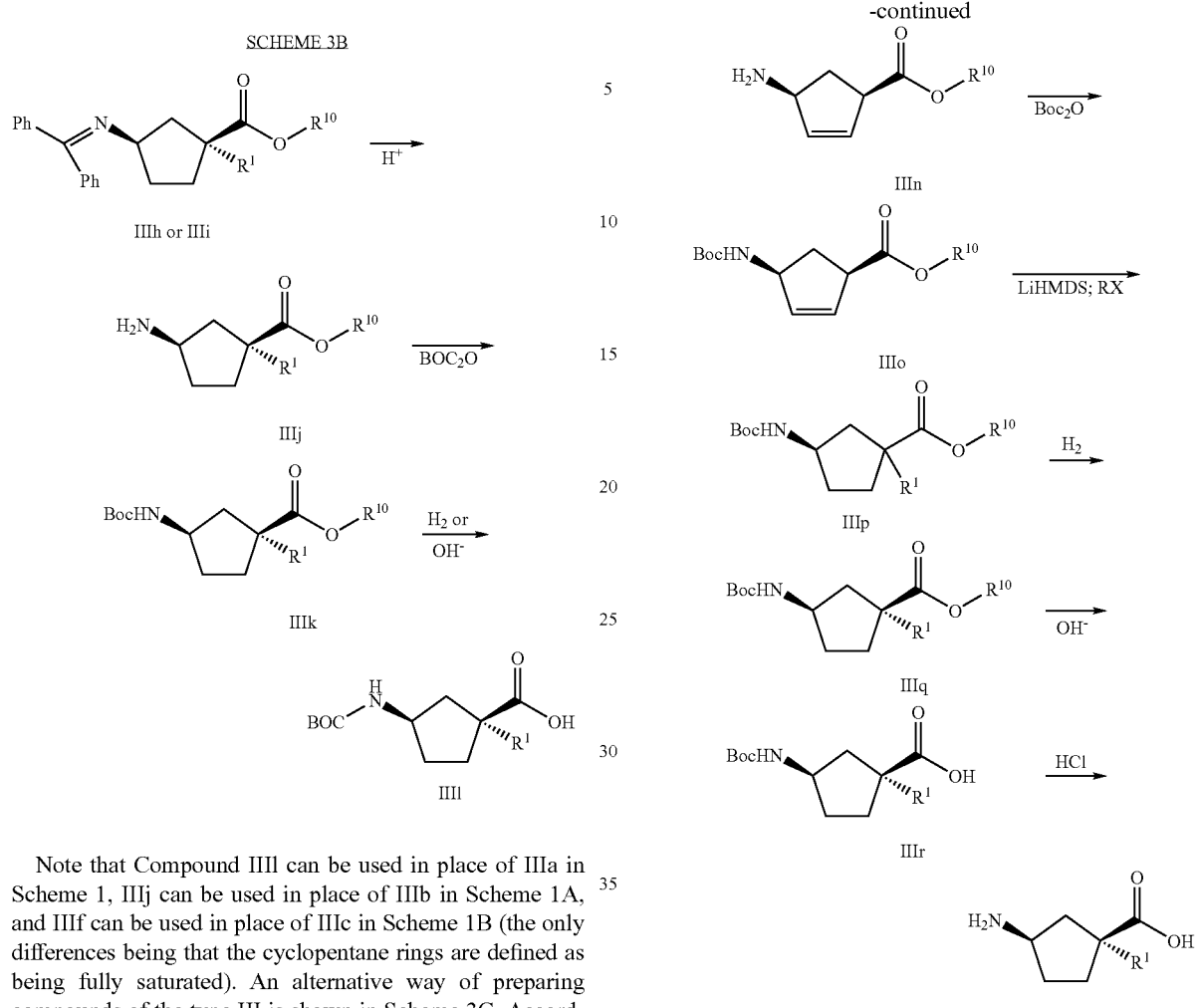

Note that Compound IIIl can be used in place of IIIa in Scheme 1, IIIj can be used in place of IIIb in Scheme 1A, and IIIf can be used in place of IIIc in Scheme 1B (the only differences being that the cyclopentane rings are defined as being fully saturated). An alternative way of preparing compounds of the type III is shown in Scheme 3C. According to this route, commercially available IIIm is converted to ester IIIn using an appropriate alcohol such as methyl or benzyl alcohol in the presence of an acid catalyst. Protection of the amine in IIIn by treatment with Boc₂O results in IIIo. Alkylation using a base such as lithium hexamethyldisilazide (LiHMDS) and an electrophile such as an alkyl halide gives IIIp, where the major diastereomer obtained is normally the cis-1,3-isomer. Separation of the cis/trans isomers can be carried out at this point or after the following step using column chromatography. If desired, hydrogenation using a catalyst such as Pd/C gives IIIq. If $R^{10}$ is benzyl hydrogenation of IIIp would directly furnish IIIr. Otherwise, IIIq can be hydrolyzed using various conditions such as treatment with NaOH to give IIIr. If desired IIIr can be treated with HCl or TFA to give IIId (used in Scheme 2a).

SCHEME 3C

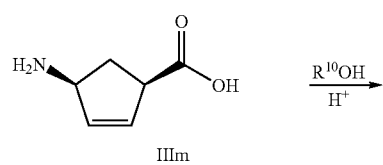

The 5-aza-tetrahydroisoquinoline fragment IV can be prepared in several ways, including in accordance to the literature methods of MarCoux, J-F. et al. (*J. Chem. Lett.*, 2000, 2 (15), 2339–2341). in accordance to the literature methods of MarCoux, J-F. et al. (*J. Chem. Lett.*, 2000, 2 (15), 2339–2341). from commercial sources, is brominated (Br₂, AcOH) to give 4-2. Metal halogen exchange (NaH, t-butyl lithium) followed by treatment with DMF provides aldehyde 4-3. Conversion of the aldehyde group to a nitrile can be achieved with sodium formate, hydroxylamine hydrochloride and formic acid. The resulting nitrile 4-4 can be treated with phosphorous oxychloride to give 2-chloropyridine 4-5. Displacement of the chloro group can be achieved with the sodium salt of a dialkylmalonate. Reduction of the nitrile group of 4-6 with hydrogen and Raney Ni catalyst is accompanied by cyclization to afford compound 4-7. Decarboxylation can be achieved in a variety of ways depending on the ester. In the case represented in Scheme 4, the t-butyl ester was decarboxylated with TFA to give 4-8. Reduction (BH₃), followed by protection of the resulting amine using Boc₂O, gives 4-9, which can be conveniently purified. Removal of the Boc protecting group to give IVa can be achieved in various ways, including by treatment with anhydrous HCl in dioxane or some other solvent.

SCHEME 4

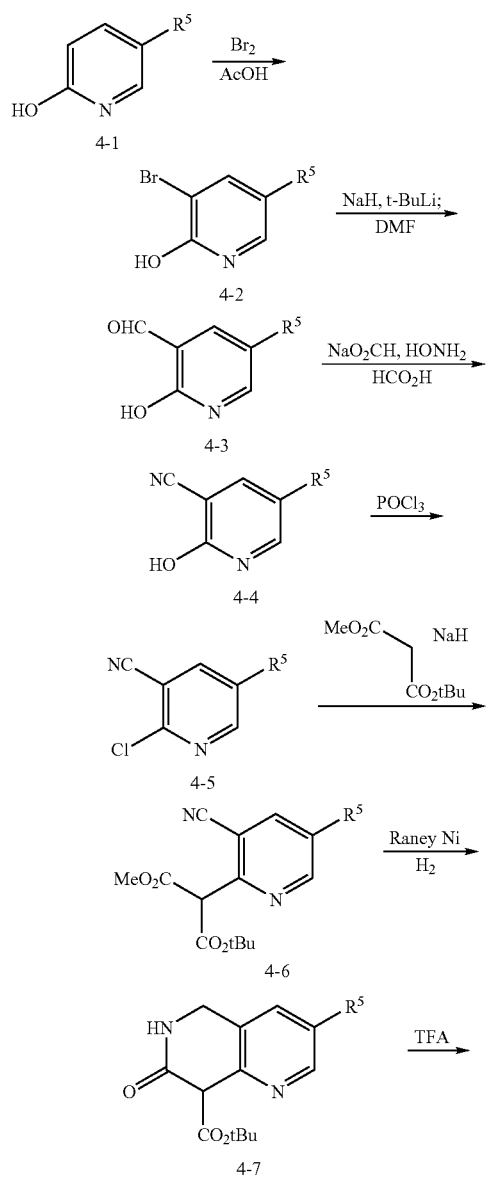

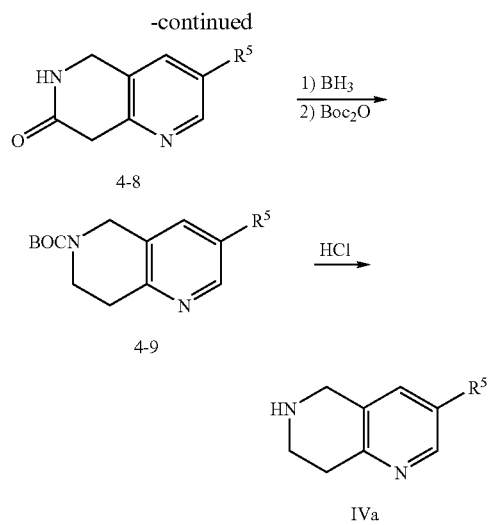

Compounds of the type IV could also be prepared according to Scheme 4A. Commercially available 4-10 can be methylated with methyl iodide in the presence of a base such as $K_2CO_3$ to give 4-11. Cycloaddition with a protected piperidinone in the presence of $NH_3$ in methanol furnishes 5-azatetrahydroiso-quinoline 4-12 ($R^{22}$ can be various protecting groups such as benzyl or benzoyl). Hydrogenation of the nitro group of compound 4-12 with hydrogen and a catalyst such as Pd/C gives 4-13. Diazonium salt formation followed by warming with sulfuric acid provides 5-aza-7-hydroxytetrahydroisoquinoline 4-14. Removal of the protecting group $R^{22}$ is achieved in different ways depending upon the nature of $R^{22}$. If $R^{22}$ is benzyl, hydrogenation in the presence of HCl and a catalyst such as Pd/C can be applied. If $R^{22}$ is benzoyl, hydrolysis can be achieved by heating in concentrated HCl solution. Installation of a Boc protecting group on 4-15 can be easily achieved with $Boc_2O$ to give 4-16. Various $R^{23}$ can then be incorporated generating ethers (see Scheme 4B). The Boc protecting group on the resulting compounds 4-17 can finally be removed with HCl or TFA to give IVb. Alternatively, Compound 4-14 itself can be converted to ethers (according to Scheme 4B). The resulting ether 4-18 can be converted to compound IVb by removal of $R^{22}$ as described above.

SCHEME 4A

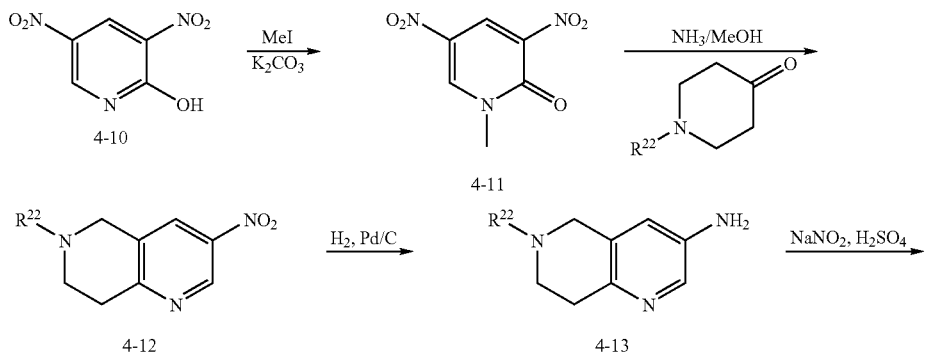

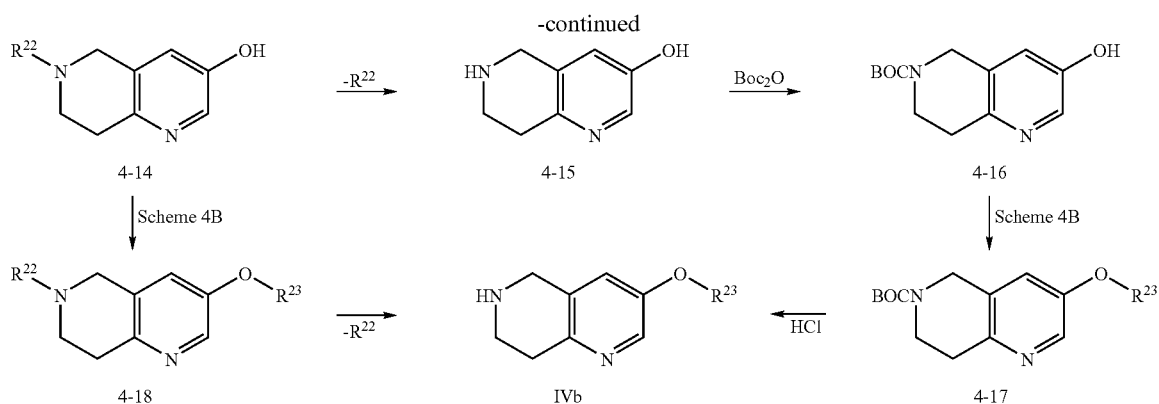

The 5-aza-7-hydroxytetrahydroisoquinolines 4-14 and 4-16 in Scheme 4A can be converted to various ethers (see Scheme 4B). Alkyl ethers can be generated from an alkyl halide and a base (such as $K_2CO_3$, NaOH, or NaH) giving compounds 4-19 and 4-22. A trifluoromethyl ether can be prepared by initial methyl xanthate formation (NaH, $CS_2$; MeI), followed by sequential treatment with 1,3-dibromo-5,5-dimethylhydantoin (or NBS) and HF/pyridine solution giving 4-20. Aryl ethers can be prepared by a number of methods, including reaction of arylboronic acids in the presence of copper (II) acetate and triethylamine, to give compounds 4-21.

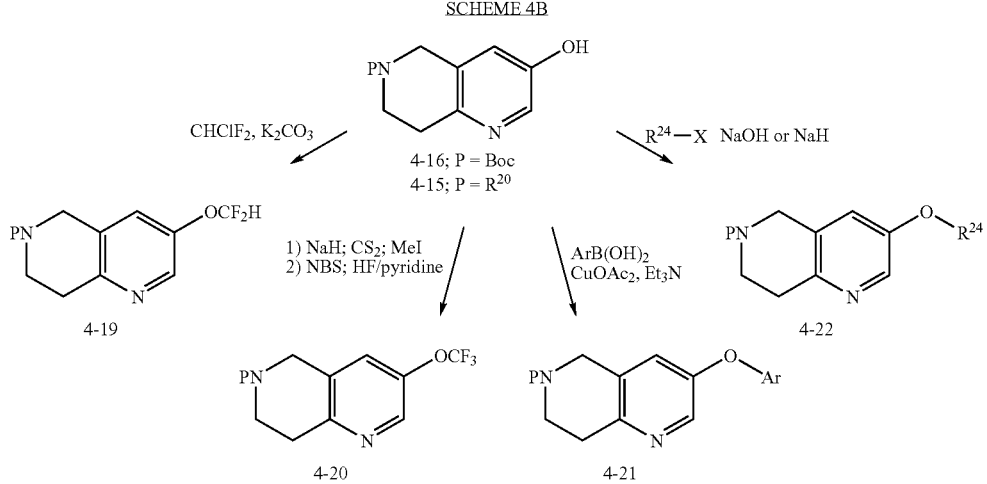

Compounds IV where $R^5$ is a halide (IVc) can be prepared according to Scheme 4C. Compound 4-13 can be converted to the halide 4-22 according to classical procedures via the diazonium salt. Alternatively the known cycloaddition reaction to a suitably protected piperidinone can be applied. Removal of the protecting group $R^{22}$ can be achieved as described previously.

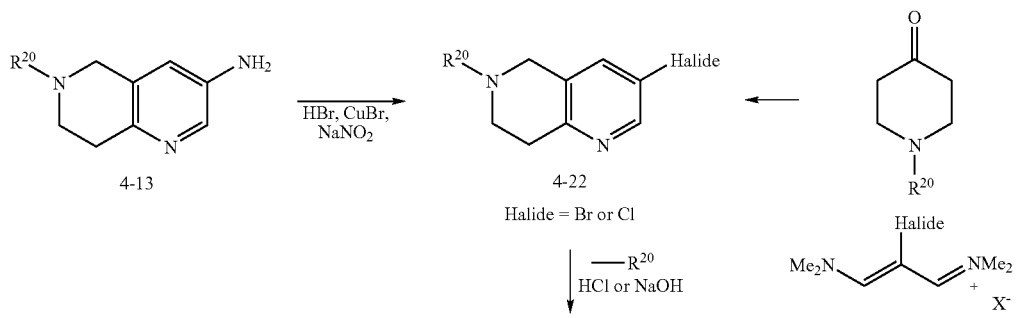

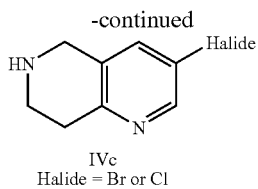

IVc
Halide = Br or Cl

After incorporation into advanced intermediates, fragments IVc can be further modified so as to prepared 7-aryl-5-azotetrahydroisoquinoline containing analogs (Scheme 4D). This can be accomplished by coupling of the 5-aza-7-halotetrahydroisoquinoline intermediates 1-5a to aryl boronic acids (or aryl stannanes), mediated by transition metal catalysts such as Pd(OAc)$_2$.

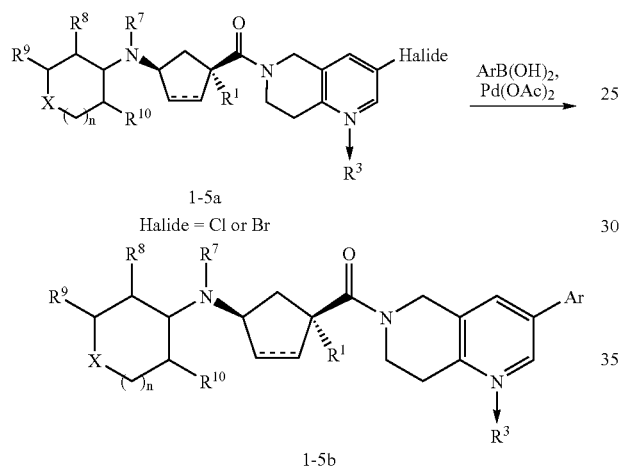

Compounds of the type represented by fragment II were often commercially available, but sometimes required preparation. For example, compounds IIa (Scheme 5) where X is either CH$_2$, S, O, or NP (P=protecting group) are commercially available. Compounds can be easily modified to IIb, having R$^8$ groups, where R$^8$ is an alkyl group, by deprotonation with a base such as LDA and alkylation with an alkyl halide (for a published procedure involving tetrahydropyran-4-one see *J. Am. Chem. Soc.*, 1991, 113, 2079–2089). Compounds IIb, can be incorporated into final target compounds as shown in the preceding Schemes. Sometimes further modification of R$^8$ can be carried out. For example, If R$^8$ is an allyl group, oxidative cleavage (O$_3$; DMS or another method) gives the dicarbonyl compound IIc, which can undergo a double reductive amination cyclization sequence as shown in Scheme 5A.

A synthesis of ketones IId where R$^8$ is an alkoxy group is detailed in Scheme 5B. According to this, commercially available 5,6-dihydro-4-methoxy-2H-pyran (5-1) is treated with m-chloroperbenzoic alcohol with an appropriate alkyl halide R$^{25}$X in a presence of a base such as sodium hydride affords the ether 5-3. Deprotection of the acetal under acidic conditions affords the desired ketones IId. In this manner, a number of 3-alkoxyderivatives can be synthesized. Alternatively, 5-2 can be itself deprotected to give 3-hydroxy-tetrahydropyran-4-one IIe. Further details, as well as examples are described in the Experimental section.

SCHEME 5

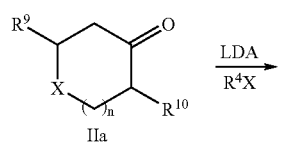

SCHEME 5B

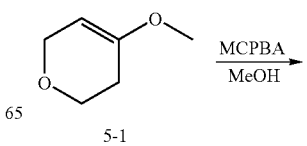

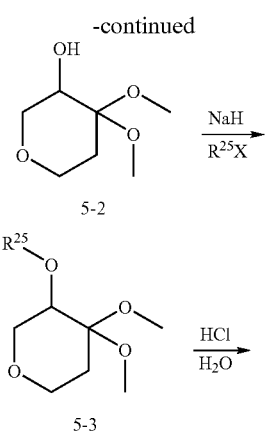

Alternatively, Intermediates 5-2 can be prepared in an asymmetric fashion according to Scheme 5C. Enol benzoate 5-4 can be prepared from ketone IIf by trapping the enolate generated upon treatment with a base such as KHMDS with benzoic anhydride. Asymmetric oxidation can be accomplished according to the conditions described by Yian Shi, et al. (J. Org. Chem., 2001, 66, 1818–1826) to give 5-6 as predominantly a single isomer. Ring opening of the epoxide and generation of the dimethyl acetal occurs in one pot by treatment with an acid such as CSA in methanol to give 5-2a. Either enantiomer of 5-2 could be obtained by appropriate choice of the sugar catalyst 5-5.

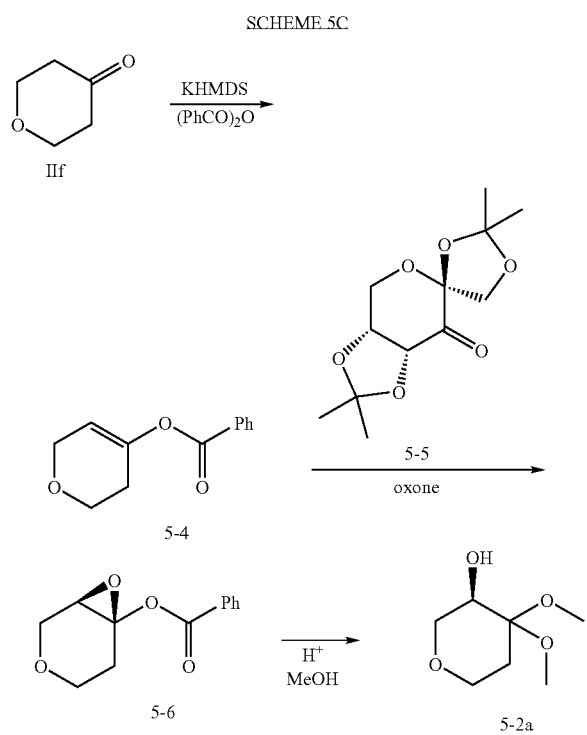

Compounds of the type V can often be obtained from commercial sources. Alternatively, compounds V can be prepared from Intermediates II according to Scheme 6. Reductive amination of II with an amine such as aminodiphenylmethane using a hydride source such as $NaB(OAc)_3$ H or $NaBH_3CN$ gives 6-1. Compounds 6-1, if warranted, can be resolved into individual isomers by various means, including crystallization with a chiral acid and chiral HPLC. Removal of the diphenylmethyl protecting group with hydrogen in the presence of a catalyst (such as Pd/C) affords subunit V.

SCHEME 6

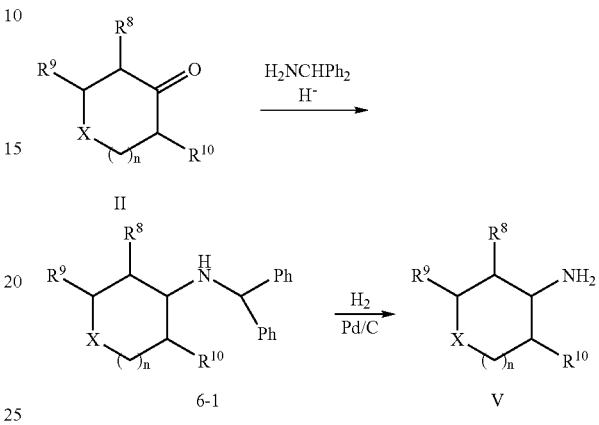

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230–400 mesh). MPLC refers to medium pressure liquid chromatography and was carried out on a silica gel stationary phase unless otherwise noted. NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative procedures for the preparation of the compounds used in the following Examples or which can be substituted for the compounds used in the following Examples which may not be commercially available.

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230–400 mesh). NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative Procedures for the preparation of the compounds used in the following Examples or which can be substituted for the compounds used in the following Examples which may not be commercially available.

Procedures for the preparation of non-carbamate piperidines.

INTERMEDIATE 1

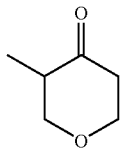

Intermediate 1 was prepared according to the procedure described in *J. Am. Chem. Soc.*, 1991, 113, 2079–2089.

INTERMEDIATE 2

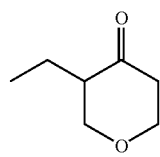

To a solution of terahydro-4H-pyran-4-one (5.0 g, 50 mmol) and hexamethylphosphoramide (8.70 mL) in tetrahydrofuran (150 mL) was added slowly a solution of lithium diisopropylamide (31.25 mL, 2 M solution) in 125 mL of tetrahydrofuran at −78° C. The reaction mixture was stirred for 5 min and then ethyl iodide was added (16.0 mL, 200 mmol). The mixture was gradually warmed to 0° C. over 2 h. The reaction mixture was quenched with a saturated solution of NH₄Cl and then extracted with ether (4×100 mL). The ether layer was washed with brine, dried (anhydrous magnesium sulfate), concentrated, and purified by flash column chromatography eluting with hexanes/ethyl acetate (4:1) to give Intermediate 2 (1.20 g, 20%).

INTERMEDIATE 3

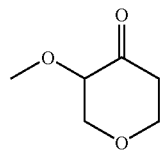

Step A:

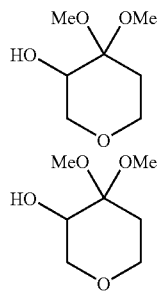

To a mixture of 5,6-dihydro-4-methoxy-2H-pyran (10.0 g, 87.5 mmol) in methanol (200 mL) at 0° C. was added dropwise a solution of 3-choloroperoxy-benzoic acid (30.2 g, 175 mmol) in methanol (50 mL) via an addition funnel. The resulting solution was stirred for 5 h allowing it to warm to room temperature. The methanol was removed under reduced pressure affording a white solid. The material was dissolved in 500 mL of dichloromethane and cooled to 0° C. To the mixture, while stirring vigorously, was added in portions an excess of solid calcium hydroxide (50–60 g). After stirring an additional 30 min, the mixture was filtered through a plug of celite and the filtrate was evaporated under reduced pressure to afford 11.62 g (82%) of the desired product as a clear oil. ¹H NMR (500 MHz, CDCl₃) δ 3.88–3.80 (m, 2H), 3.73–3.68 (m, 2H), 3.54–3.48 (m, 1H), 3.28 (s, 3H), 2.00–1.93 (m, 1H), 1.82–1.77 (m, 1H).

Step B:

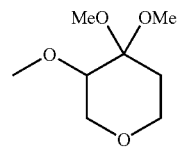

To a cooled (0° C.) solution of the product from Step A, Intermediate 3 (9.40 g, 58.0 mmol) in tetrahydrofuran (200 mL), under nitrogen, was slowly added NaH (2.32 g, 58.0 mmol) and the resulting slurry was stirred for 1 h at 0° C. Iodomethane (7.22 mL, 116 mmol) was then added via syringe to the slurry and the resulting mixture was stirred overnight allowing it to warm to room temperature. The reaction was quenched with a saturated solution of ammonium chloride (200 mL) and the organic layer was then removed using a separatory funnel. The aqueous layer was extracted with ether (3×150 mL) and all the organics were combined, dried over anhydrous sodium sulfate, filtered, and evaporated in vacuo. Purification was accomplished by flash column using a stepwise gradient eluant of 10–60% ether/hexanes to afford 8.46 g (83%) of the desired product as a clear oil. ¹H NMR (500 MHz, CDCl₃) δ 3.98 (dd, J=2.5, 12.4 Hz, 1H), 3.77 (ddd, J=3.5, 7.1, 10.8 Hz, 1H), 3.57 (dd, J=1.4, 12.4 Hz, 1H), 3.50 (dd, J=2.5, 11.7 Hz, 1H), 3.46 (s, 3H), 3.25 (s, 3H), 3.22 (s, 3H), 3.22–3.20 (m, 1H), 1.96 (ddd, J=4.7, 11.8, 16.5 Hz, 1H), 1.75 (br dd, J=1.7, 14.2 Hz, 1H).

Step C:

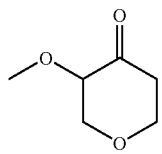

A solution of the product from Step B, Intermediate 3 (3.0 g, 17.04 mmol) in tetrahydrofuran/water (60 mL/10 mL) was treated with concentrated hydrochloric acid (6 mL) and the resulting solution was stirred at room temperature for 1 h. The mixture was concentrated in vacuo to remove the tetrahydrofuran and the aqueous layer then extracted with ether (6×50 mL). The organics were combined, dried over anhydrous sodium sulfate, filtered, and evaporated under reduced pressure to afford intermediate 24 (1.75 g, 79%) as a clear oil. ¹H NMR (500 MHz, CDCl₃) δ 4.23 (ddd, J=1.2, 11.4, 12.4 Hz, 1H), 4.15–4.09 (m, 1H), 3.82 (dd, J=5.95, 8.7 Hz, 1H), 3.74 (ddd, J=5.5, 8.5, 13.6 Hz, 1H), 3.56 (dd, J=8.8, 11.3 Hz, 1H), 3.50 (s, 3H), 2.61 (app dd, J=5.0, 8.9 Hz, 2H).

INTERMEDIATE 4

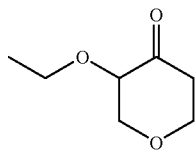

This intermediate was prepared in an analogous fashion to that of Intermediate 3, except iodomethane was replaced with iodoethane. Purification by MPLC (gradient elution from 0–40% ethyl acetate/hexanes) afforded 683 mg (66%) of the final compound as a clear oil.

INTERMEDIATE 5

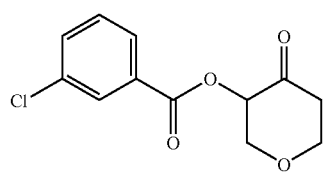

To a suspension of $Na_2HPO_4$ (24.85 g, 175.1 mmol) and 5,6-dihydro-4-methoxy-2H-pyran (10.0 g, 87.5 mmol) in dichloromethane (200 mL) at 0° C. was added dropwise a solution of 3-chloroperoxybenzoic acid (30.2 g, 175 mmol) in dichloromethane (50 mL) via addition funnel. The resulting solution was stirred for 5 h allowing it to warm to room temperature. The reaction was quenched with water (200 mL) and the organics were separated. The aqueous layer was extracted with dichloromethane (200 mL) and the organics combined, dried over anhydrous sodium sulfate, filtered, and evaporated in vacuo to afford Intermediate 5 (19.12 g, 86%) as a white solid.

INTERMEDIATE 6

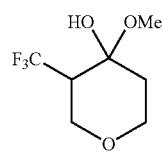

To a mixture of 5,6-dihydro-4-methoxy-2H-pyran (0.5 g, 4 mmol) in acetonitrile/water (15 mL, 1:1) at room temperature was added 1-(chloromethyl)-4-fluoro-1,4-diazoniabicyclo[2.2.2.]octane bis(tetrafluoroborate) (1.5 g, 4.4 mmol, SELECTFLUOR™) in one lot and the resulting reaction mixture was stirred at room temperature until completion. Solid NaCl was then added and the reaction mixture was then extracted with ether (4×50 mL). The ether layer was dried (anhydrous magnesium sulfate) and concentrated to yield 0.34 g (65%) of the title compound that required no further purification. $^1$H NMR (500 MHz, $CDCl_3$): d 4.95 (m, 1H), 4.4–4.21 (m, 2H), 3.72–3.65 (m, 2H), 2.75 (m, 2H).

INTERMEDIATE 7

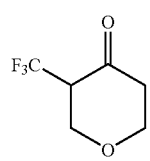 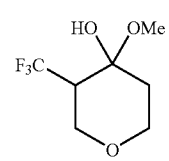

Step A:

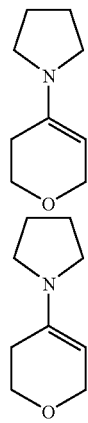

A mixture of tetrahydro-4H-pyran-4-one (10.0 g, 100 mmol) and pyrrolidine (11 g, 150 mmol) was stirred at room temperature for 1 h. The excess pyrrolidine was removed in vacuo and the residue was dried overnight under high vacuum. The enamine was obtained as a yellow liquid (14.7 g) which was used in the next step without further purification.

Step B:

The enamine, prepared in Step A, Intermediate 7 (1.54 g, 10 mmol) and 4-N,N-dimethylpyridine (1.22 g) were treated with N,N-dimethylformamide (25 mL). The mixture was cooled to 0° C. and solid 5-(trifluoromethyl)dibenzothiophenium trifluoromethanesulfonate (4.0 g, 10 mmol) was added. The resulting mixture was stirred at 0° C. for 1 h, then quenched with 30 mL of concentrated aqueous HCl. The resulting mixture was stirred for 2 h and then extracted with ether (4×70 mL). The combined ether layers were washed with water (50 mL) and brine (50 mL), dried over $Na_2SO_4$, filtered, and evaporated. The residue was purified on silica gel (eluant: 10% ether/hexanes) to yield two components. The more polar component (200 mg) was the desired product. $^1$H-NMR showed that it might exist in a semi-ketal form. $^1$H NMR (500 MHz, $CDCl_3$) δ 4.43–3.38 (m, 5H), 3.24, 3.18 (ss, 3H) 2.52 (m, 1H), 1.82 (m, 1H). The less polar product (100 mg) was confirmed as alpha-alpha' di-trifluoromethyl tetrahydro-4H-pyran-4-one. $^1$H NMR (500 MHz, $CDCl_3$) δ 4.59 (dd, 2H), 3.24, 3.80 (t, J=

INTERMEDIATE 8

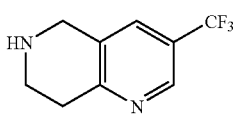

Step A:

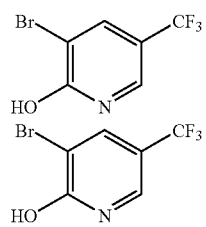

To a solution of 5-trifluoromethyl-2-pyridinal (51 g, 310 mmol) and sodium acetate (26.2 g, 319 mmol) in glacial acetic acid (200 mL) was added bromine (16.7 mL, 325 mmol) and the resulting mixture was heated at 80° C. for 2.5 h. The reaction was allowed to cool to room temperature and then was evaporated under reduced pressure. The residue was neutralized with saturated NaHCO$_3$ solution and extracted with ethyl acetate (3×200 mL). The organics were combined, dried over MgSO$_4$ CDCl$_3$) δ 8.04 (d, J=2.6 Hz, 1H), 7.89 (m, 1H).

Step B:

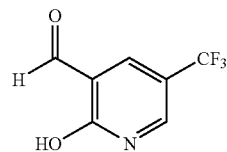

Under nitrogen, the substituted pyridine described in Step A, Intermediate 8 (48.8 g, 202 mmol) was added in small portions to a suspension of NaH (8.9 g, 220 mmol) in anhydrous tetrahydrofuran (500 mL). After complete addition of the intermediate, the reaction mixture was cooled to −78° C. and treated with tert-butyllithium (260 mL, 444 mmol) added dropwise via syringe. After stirring for 5 min, N,N-dimethylformamide (50 mL, 707 mmol) was added slowly to maintain the temperature below −50° C. The resulting mixture was then stirred for 10 h allowing it to warm to room temperature. The mixture was quenched with 2 N HCl and then diluted with ethyl acetate (1000 mL). The organic layer was separated, washed with brine, dried over MgSO4, and evaporated in vacuo. The desired product was precipitated out of ethyl acetate and hexanes and filtered to yield a light brown solid (28.55 g, 74%). $^1$H NMR (500 MHz, CD$_3$OD) δ 10.13 (s, 1H), 8.21 (s, 2H).

Step C:

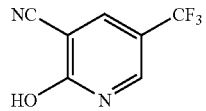

A mixture of the intermediate from Step B, Intermediate 8 (18 g, 95 mmol), sodium formate (7.1 g, 110 mmol), hydroxylamine hydrochloride (7.3 g, 110 mmol), and formic acid (150 mL) was stirred at room temperature for 2 h and then heated to reflux overnight. The reaction mixture was cooled and allowed to stand at room temperature for 7 days. The reaction was poured into water and extracted with ethyl acetate (3×). The combined organic layers were washed with water (2×), saturated NaHCO$_3$ and brine, dried over Na$_2$SO$_4$, filtered, and concentrated in vacuo to yield the desired product as a brown powder (17.84 g, 90%) $^1$H NMR (400 MHz CD$_3$OD) δ 8.37 (d, J=2.7 Hz, 1H), 8.19 (q, J=0.7 Hz, 0.3 Hz, 1H).

Step D:

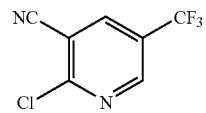

To a mixture of phosphorous oxychloride (13.4 mL, 144 mmol) and quinoline (8.7 mL, 73 mmol) was added the product from Step C, Intermediate 8, (24.6 g, 131 mmol) and the resulting mixture was heated to reflux for 3 h. The reaction was cooled to 100° C. before water (70 mL) was slowly added. The mixture was further cooled to room temperature and neutralized carefully with saturated NaHCO$_3$ solution. The aqueous layer was extracted with ethyl acetate (3×) and the organic layers were combined, dried over MgSO$_4$, filtered, and evaporated in vacuo. The crude product was purified by flash chromatography to afford (23.5 g, 87%) of the desired compound. $^1$H NMR (500 MHz, CDCl$_3$) δ 8.88 (d, J=2.0 Hz, 1H), 8.26 (d, J=2.5 Hz, 1H).

Step E:

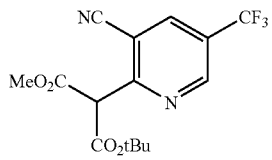

To a suspension of NaH (7.8 g, 200 mmol) in tetrahydrofuran (100 mL) under nitrogen was added dropwise a solution of tert-butyl methyl malonate (20 mL, 120 mmol) in anhydrous tetrahydrofuran (100 mL) via syringe. The reaction mixture was stirred for 0.5 h before a solution of the intermediate prepared in Step D, Intermediate 8 (20.1 g, 97.6 mmol) in tetrahydrofuran (200 mL) was added slowly via syringe. The reaction was stirred at room temperature overnight, then quenched with a saturated solution of NH$_4$Cl. The organic layer was separated and the aqueous layer was extracted with ethyl acetate (3×). The combined organic layers were washed with water (3×), dried over Na$_2$SO$_4$, filtered, and evaporated in vacuo. Flash chromatography afforded 31.76 g (95%) of the pure desired product. $^1$H NMR (500 MHz, CDCl$_3$) δ 9.03 (d, J=1.5 Hz, 1H), 8.25 (d, J=2.0 Hz, 1H), 5.2 (s, 1H), 3.86 (s, 3H), 1.52 (s, 9H).

Step F

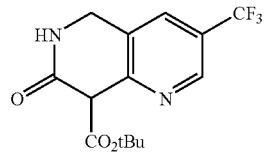

A suspension of Raney Ni (1 g) and the product from Step E, Intermediate 8 (18.2 g, 52.9 mmol) in ethanol (130 mL) was placed on a Parr apparatus and hydrogenated at 40 psi H$_2$ overnight. The suspension was filtered through celite and the filtrate was evaporated in vacuo to afford 16.35 g (98%) of the crude product. $^1$H NMR (500 MHz, CDCl$_3$) δ 8.83 (s, 1H), 7.89 (s, 1H), 7.82 (s, 1H), 4.83 (d, J=16 Hz, 1H), 4.72 (s, 1H), 4.49 (d, J=16 Hz, 1H), 1.45 (s, 9H).

Step G

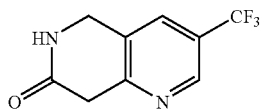

To the mixture of the product from Step F, Intermediate 8 (16 g, 51 mmol) in dichloromethane (60 mL) was added TFA (30 mL) and the resulting mixture was stirred at room temperature for 0.5 h. The solution was evaporated under reduced pressure and the residue was dissolved in dichloromethane. The mixture was neutralized by the slow addition of a solution of saturated sodium bicarbonate and the organic layer was removed. The aqueous layer was extracted with dichloromethane (4×) and the combined organic layers were dried over Na$_2$SO$_4$, filtered, and evaporated in vacuo to afford 10.42 g (95%) of the desired product. $^1$H NMR (400 MHz, CDCl$_3$) δ 8.81 (s, 1H), 7.78 (s, 1H), 7.30 (s, 1H), 4.63 (s, 2H), 3.90 (s, 2H).

Step H

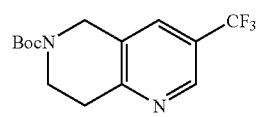

To a solution of the product from Step G, Intermediate 8 (18.0 g, 83.3 mmol) in tetrahydrofuran (50 mL) was added 1.0 M borane in tetrahydrofuran (417 mL, 420 mmol) and the resulting solution was stirred at room temperature overnight. The solution was evaporated under reduced pressure and the residue was treated with 1% HCl/methanol solution. The resutling mixture was heated at 50° C. overnight to breakdown the borane complex. Treatment with acidic methanol was repeated twice to insure that the borane complex was removed. A solution of this crude product (83.3 mmol, assuming 100% conversion) and diisopropylethylamine (43 mL, 250 mmol) in dichloromethane was treated with di-tert-butyl dicarbonate (36.4 g, 167 mmol) and the resulting mixture was stirred at room temperature overnight. The solution was washed with saturated sodium bicarbonate solution, water, and brine. The aqueous layers were combined and back-washed with dichloromethane (2×). The combined organic layers were then dried over Na$_2$SO$_4$, filtered, and evaporated to dryness. The crude product was purified by flash chromatography and MPLC to afford (11.89 g, 47%) as a yellow solid. $^1$H NMR (500 MHz, CDCl$_3$) δ 8.69 (s, 1H), 7.66 (s, 1H), 4.67 (s, 2H), 3.79 (t, J=6.0 Hz, 2H), 3.08 (t, J=5.5 Hz, 2H), 1.51 (s, 9H)

Step I

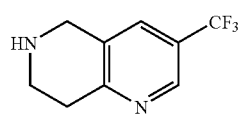

The product described in Step H, Intermediate 8 (11.89 g) was treated with a solution of 4 N HCl in dioxane. The solution was stirred at room temperature for 2 h and then evaporated in vacuo to afford Intermediate 8 (10.85 g, 99%) as a yellow powder. LC-MS for C$_9$H$_{10}$F$_3$N$_2$ calculated 202.07, found [M+H]$^+$ 203.0.

INTERMEDIATE 9

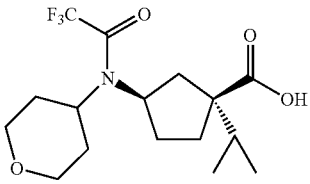

A mixture of (1R,4S)-4-amino-cyclopen-2-ene carboxylic acid (130 g, 1.0 mol), water (250 mL), sodium bicarbonate (170 g, 2.0 mol) and tetrahydrofuran (750 mL) was stirred for 30 min, then solid di-tert-butyl dicarbonate (230 g, 1.05 mol) was added. The mixture was stirred over the weekend, filtered to remove the insoluble material, evaporated to remove the tetrahydrofuran, and cooled to 0° C. To the residue was added 2 N aqueous HCl until the pH reached 3 (~500 mL). The resulting precipitate was collected by filtration and washed with water and dried under vacuum overnight. The desired acid was obtained as a white solid (230 g, 100%). $^1$H NMR (400 MHz, CD$_3$OD): δ 5.95 (m, 1H), 5.79 (m, 1H), 4.80 (br s, 1H), 3.45 (m, 1H), 2.50 (m, 1H), 1.79 (m, 1H), 1.44 (s, 9H).

Step B:

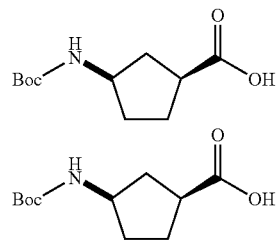

The acid prepared in Step A (230 g, 1.0 mol) and 10% Pd/C (5.0 g) in 500 mL of methanol was placed on a Parr apparatus and hydrogenated under 50 psi of hydrogen for 1 h. The catalyst was removed by filtration and the filtrate was evaporated. The residue was dissolved in dichloromethane and dried over anhydrous sodium sulfate. After filtration, the filtrate was evaporated and dried under vacuum. The title compound was obtained as a light yellow solid (230 g, 99%). LC-MS for C$_{11}$H$_{19}$NO$_4$ calculated 229, found [M+H]$^+$ 230.

Step C:

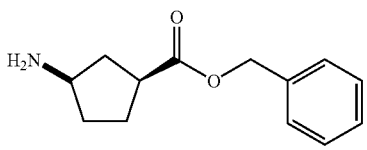

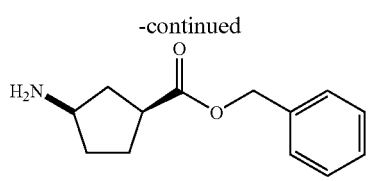

To a mechanically stirred solution of the acid prepared in Step B, Procedure A, Intermediate 9 (230 g, 1.00 mol) in 500 mL of N,N-dimethylformamide was added solid potassium carbonate (210 g, 1.5 mol). The resulting mixture was stirred for 20 min and neat benzyl bromide (120 mL, 1.0 mol) was added in one portion. An exothermic reaction was observed. After being stirred for 3 h at room temperature, the entire mixture was poured into an ice-water mixture (1000 mL). The crude product was extracted out with ether (2×800 mL). The combined ether layers were washed with water, dried over sodium sulfate, filtered and evaporated to offer a yellow solid. This solid was mixed with 4 N HCl in dioxane (400 mL), stirred overnight and condensed. The resulting solid was collected by filtration, washed with ether and dried under vacuum. The title product was obtained as a hydrochloride salt (140 g, 55%). $^1$H NMR (400 MHz, CD$_3$OD): δ 5.15 (s, 2H), 3.65 (m, 1H), 3.02 (q, J=8 Hz, 1H), 2.50 (m, 1H), 2.15 (m, 1H), 2.05 (m, 2H), 1.90 (m, 1H), 1.75 (m, 1H).

Step D:

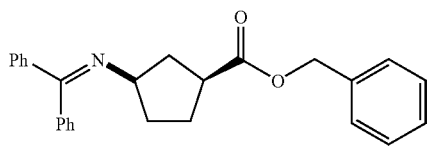

The amino benzyl ester HCl salt prepared in Step C, Procedure A, Intermediate 9 (130 g, 0.50 mol) was suspended in 500 mL of dichloromethane. Benzophenone imine (91 g, 0.50 mol) was added. The resulting mixture was stirred overnight, and filtered to remove the inorganic salt. The filtrate was washed with water and brine, dried over sodium sulfate, and evaporated. The residue was dissolved in 200 mL of toluene, and evaporated. This procedure was repeated once more. The title compound (178 g) was obtained as a brown oil which was used in the next step without further purification. $^1$H NMR (400 MHz, CDCl$_3$): δ 1.80 (m, 1H), 1.95 (m, 2H), 2.15 (m, 2H), 2.50 (m, 1H), 2.89 (m, 1H), 3.61 (m, 1H), 5.20 (s, 2H), 7.18 (d, 2H), 7.38 (m, 8H), 7.47 (m, 3H), 7.64 (d, 2H).

Step E:

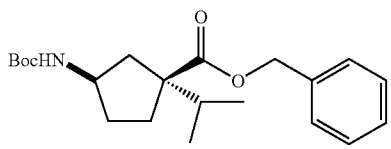

The starting Schiff base benzyl ester from Step D, Procedure A, Intermediate 9 (76.6 g, 200 mmol) in 300 mL of tetrahydrofuran was cooled to −78° C. under nitrogen. While stirring, a solution of lithium diisopropylamide (2.0 M, 110 mL, 220 mmol) in heptane was added over 20 min. The mixture was stirred for 30 min at −78° C., then a solution of 68 mL of isopropyl iodide (440 mmol) in 50 mL of tetrahydrofuran was added, and the mixture was allowed to stir for 30 min. The reaction temperature was raised to 0° C. by removing the cooling bath. After being stirred for 2 h, the entire mixture was evaporated to remove the tetrahydrofuran. The residue was dissolved in ether (1000 mL), washed with water and brine, dried over sodium sulfate, and evaporated. The crude product was dissolved in 500 mL of tetrahydrofuran, mixed with 400 mL of aqueous 1 N HCl, stirred for 1 h, and evaporated to remove tetrahydrofuran at 50° C. The aqueous solution was extracted with hexanes (3×), made alkaline with saturated aqueous sodium carbonate (pH>9) and treated with a solution of di-tert-butyl dicarbonate (53 g) in 500 mL of dichloromethane. The resulting reaction mixture was stirred for 30 min. The organic phase was separated and the aqueous phase was extracted with dichloromethane (3×). The combined organic phases were dried over sodium sulfate and evaporated. The residue was purified by flash chromatography (silica gel, 10% ethyl acetate/hexanes) to yield a mixture of the title compound as a mixture of cis and trans isomers (~1:1, 24 g). Further purification by MPLC (8% ethyl acetate/hexanes) afforded the single desired cis isomer (fast-eluted, 7.3 g) and the undesired trans isomer (slow-eluted). ESI-MS calculated for C$_{21}$H$_{31}$NO$_4$: 361; Found: [M+H]$^+$ 362. $^1$H NMR (500 MHz, CDCl$_3$): δ 7.36 (m, 5H), 5.14 (s, 2H), 4.77 (m, 1H), 4.01 (d, J=5.0 Hz, 1H), 2.17 (m, 1H), 1.99–1.53 (m, 5H), 1.42 (m, 9H), 0.85 (d, J=7.0 Hz 6H)

Step F:

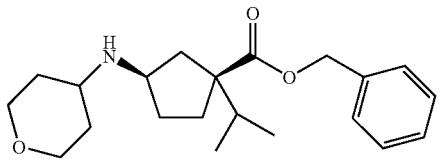

The BOC-amine from Step E (7.3 g, 21 mmol) was treated with hydrogen chloride (4 N solution in dioxane). The reaction was allowed to stir for 1.5 h at room temperature before being concentrated to remove the dioxane. The resultant solid was dissolved in dichloromethane (150 mL) and treated with tetrahydropyranone (2.4 g, 24 mmol) and triethylamine (2.8 mL, 20 mmol). The resulting solution was stirred at room temperature for 5 min before 4 Å powdered molecular sieves (~5 g) and sodium triacetoxyborohydride (17 g, 80 mmol) where added. The mixture was stirred for 2 h at room temperature. The reaction was filtered through celite and washed with a saturated aqueous sodium bicarbonate solution then brine. The organic layer was dried over MgSO$_4$, filtered, and concentrated under reduced pressure. To give 6.7 g of a colorless oil (97%). ESI-MS calculated for C$_{21}$H$_{31}$NO$_3$: 345; Found: 346 (M+H).

Step G:

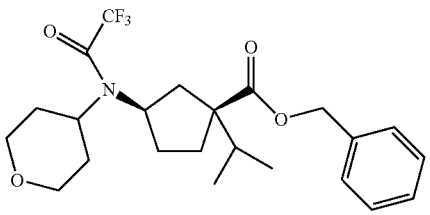

The amine from Step F (6.6 g, 19 mmol) was added to a solution of dichloromethane (100 mL) and triethylamine (2.9 mL, 21 mmol). Trifluoroacetic anhydride (3.0 mL, 21 mmol) was added to the solution dropwise at room temperature and the resulting solution was allowed to stir at room temperature for 2.5 h. The reaction was diluted with dichloromethane (100 mL) and washed with hydrochloric acid (1 N aqueous solution) followed by brine. The organic layer was dried over MgSO$_4$, filtered and concentrated under reduced pressure. The crude yellow oil was purified by MPLC (silica gel, 0–30% ethyl acetate/hexanes) to give 4.9 g of a colorless oil (58%). $^1$H NMR (CDCl$_3$, 500 MHz): δ 7.37 (m, 5H), 5.18 (m, 2H), 4.20–3.88 (m, 4H), 3.64 (m, 1H), 3.42 (t, J=12.0 Hz, 3.26 (t, J=11.5 Hz, 1H), 3.18 (t, J=11.5 Hz, 1H), 2.81–2.65 (m, 2H), 2.26 (m, 1H), 1.89–1.80 (m, 3H) 1.64–1.40 (m, 3H), 0.874 (m, 6H).

Step H:

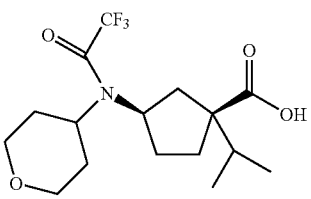

The product from Step G (3.5 g, 7.9 mmol) was dissolved in methanol (60 mL) and treated with 20% palladium hydroxide on activated carbon (350 mg). This mixture was placed under a hydrogen atmosphere (1 atm) and allowed to stir at room temperature for 1.2 h. The reaction was filtered through celite and concentrated under reduced pressure to give 2.63 g of a white solid (95%).

Procedure B:

Step A:

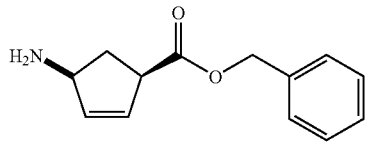

To a magnetically stirred solution of the acid from Step A, Procedure A, Intermediate 9 (159 g, 700 mmol) in 500 mL of N,N-dimethylformamide was added solid potassium carbonate (138 g, 1.00 mol). The resulting mixture was stirred for 20 min before neat benzyl bromide (84 mL, 0.7 mol) was added in one portion. An exothermic reaction was observed. After stirred overnight at room temperature, the entire mixture was poured into an ice-water mixture (1000 mL). The crude product was extracted out with ethyl acetate (2×800 mL). The combined organic layers were washed with water, dried over sodium sulfate, filtered and evaporated to offer a brown oil. This material was mixed with 4 N HCl in dioxane (350 mL) and stirred until gas evolution was observed. 500 mL of ether was added and the precipitate was collected by filtration and washed with ether and hexanes. The desired product was obtained as a hydrochloride salt (164 g, 93% ). $^1$H NMR (400 MHz, CD$_3$OD): δ 7.38 (m, 5H), 6.25 (m, 1H), 5.94 (m, 1H), 5.20 (s, 2H), 4.32 (br s, 1H), 3.80 (br s, 1H), 2.67 (m, 1H), 2.14 (m, 1H).

Step B:

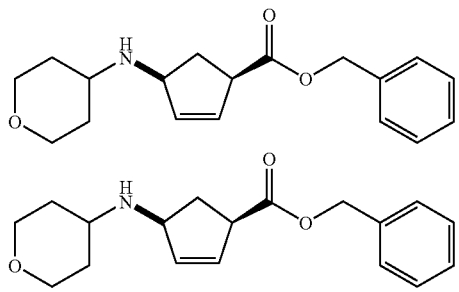

To a mixture of the amino ester HCl salt from Step A, Procedure B, Intermediate 9 (38 g, 150 mmol), tetrahydro-4-H-pyran-4-one (15 g, 150 mmol), diisopropylethylamine (20.6 g, 160 mmol) and 4 Å powdered molecular sieves (~20 g) in 200 mL of dichloromethane was added sodium triacetoxyborohydride (42.4 g, 200 mmol) in multiple portions. After complete addition, the mixture was stirred at room temperature overnight, quenched with saturated aqueous sodium carbonate, and filtered through celite. The crude product was extracted into dichloromethane (3×), dried over sodium sulfate and evaporated. The residue was purified by flash chromatography (silica gel, 10% [aqueous NH$_4$OH/methanol 1/9]/dichloromethane). The desired fractions were combined and evaporated. The resulting residue was mixed with tetrahydrofuran and evaporated, redissolved in toluene and evaporated, and dried under vacuum to yield a light brown oil (38 g, 84%). $^1$H NMR (400 MHz, CDCl$_3$): δ 7.38 (m, 5H), 5.98 (m, 1H), 5.85 (m, 1H), 3.98 (m, 3H), 3.54 (m, 1H), 3.40 (m, 2H), 2.82 (m, 1H), 2.44 (m, 1H), 1.90 (m, 1H), 1.79 (m, 2H), 1.70 (m, 1H), 1.44 (m, 2H).

Step C:

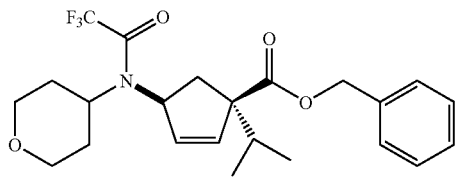

To a round bottom flask containing solid potassium bis(trimethylsilyl)amide (30 g, 150 mmol) under nitrogen was added 500 mL of anhydrous tetrahydrofuran, and the resulting solution was cooled to −78° C. A solution of the amino ester from Step B, Procedure B, Intermediate 9 (38 g, 130 mmol) in 100 mL of tetrahydrofuran was added over 20 min. The reaction mixture was warmed to −15° C. The mixture was stirred at −15° C. for 1 h and then recooled to −78° C. A neat solution of isopropyl iodide (65 mL, 380 mmol) was added. The flask was placed into a −15° C. bath again. After a few min, a large amount of white precipitate was formed. The reaction mixture was stirred for an additional 1 h, poured into a mixture of ice and water, and extracted with ethyl ether (3×). The ether layers were washed with water and brine, dried over sodium sulfate and evaporated. The resulting residue was dissolved in dichloromethane, dried over sodium sulfate again and evaporated. The residue was dried under vacuum, mixed with dichloromethane (200 mL) and cooled to 0° C. under nitrogen. To the solution was added pyridine (33 mL, 400 mmol) and trifluoroacetic anhydride (27 mL, 190 mmol) dropwise. After 1 h, the reaction was quenched with water. The organic phase was separated and washed with 2 N aqueous HCl, water and then brine. After being dried over sodium sulfate and evaporated, the residue was purified by flash chromatography (silica gel, 20% ethyl acetate/hexanes) to yield a light brown oil (41 g, 74%). $^1$H-NMR showed a 5:1 mixture of cis/trans isomers). $^1$H NMR (400 MHz, CDCl$_3$): δ CH=CH: Cis: 6.06 (m, 1H), 5.68 (m, 1H). Trans: 5.92 (m, 0.2H), 5.79 (m, 0.2H). LC-MS for C$_{23}$H$_{27}$F$_3$NO$_4$ calculated 439, found [M+H]$^+$ 440.

Step D:

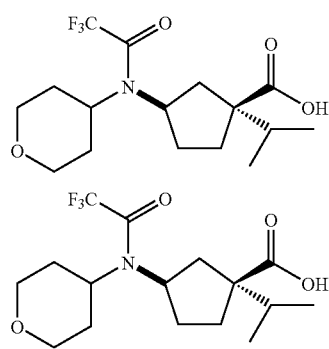

The unsaturated benzyl ester from Step C, Procedure B, Intermediate 9 (41 g) and 10% Pd/C (2.0 g) in ethyl acetate (100 mL) was hydrogenated on a Parr apparatus under 50 psi of hydrogen overnight. The catalyst was removed by filtration through a pad of celite. The filtrate was evaporated and dissolved in dichloromethane, evaporated and dried under vacuum overnight. The desired acid was obtained as a gummy white solid (32.5 g, 100%). LC-MS for C$_{16}$H$_{23}$F$_3$NO$_4$ calculated 351, found [M+H]$^+$ 352.

INTERMEDIATE 10

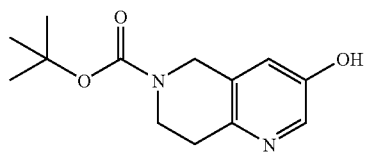

-continued

Step A:

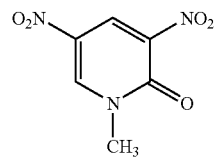

To a solution of 2-hydroxy-3,5-dinitropyridine (5.0 g, 27 mmol) in N,N-dimethylformamide (15 mL) was added powdered potassium carbonate (54 mmol) and the resulting mixture was stirred at 0° C. for 2 min. Methyl Iodide (27 mol) was then added slowly and the mixture was warmed up to room temperature. After stirring for an additional 1 h, the reddish orange mixture was filtered and the filtrate was concentrated. Purification by column chromatography and eluting with hexanes/ethyl acetate (0–50%) afforded 5.07 g (96%) of the desired product. $^1$H NMR (500 MHz, DMSO): δ 9.59 (d, J=2.9 Hz, 1H), 9.00 (d, J=2.9 Hz, 1H), 3.67 (m, 3H).

Step B

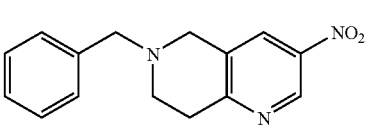

To the intermediate from Step A (4.0 g, 20 mmol) in 200 mL of 2 M methanol/ammonia was added 1-benzyl-4-piperdone (4.5 g, 24 mmol) and the resulting mixture was heated at 60° C. for 24 h. The solvent was evaporated and the crude mixture was purified by flash column chromatography. Eluting with hexanes/ethyl acetate (15–20%) gave 4.0 g (72%) of the title product. $^1$H NMR (500 MHz, CD$_3$OD): δ 9.14 (d, J=2.5 Hz, 1H), 8.30 (d, J=2.3 Hz, 1H), 7.40–7.28 (m, 5H), 3.76 (s, 4H), 3.10 (t, J=6.0 Hz, 2H), 2.91 (t, J=.0 Hz, 2H).

Step C

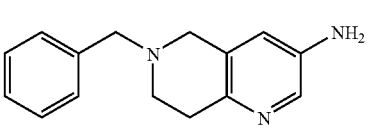

A mixture of the intermediate from Step B (4 g) and Pd/C (250 mg, 5%) in methanol (125 mL) was hydrogenated at room temperature for 3.5 h. The mixture was filtered through celite and concentrated. Purification by column chromatography and eluting with hexanes/ethyl acetate (1:1) and methanol (5%) afforded 2.52 g (71%) of the title product. $^1$H NMR (500 MHz, CD$_3$OD): δ 7.79 (d, J=2.5 Hz, 1H), 7.39–7.28 (m, 5H), 6.76 (d, J=2.5 Hz, 1H), 3.69 (s, 2H), 3.53 (s, 2H), 2.84–2.81 (m, 4H).

Step D

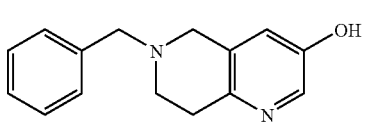

To a mixture of the intermediate from Step C (2.4 g, 10 mmol) and 10 mL of 20% sulfuric acid at 0° C. was added a solution of sodium nitrite (0.76 g, 11 mmol) in water (5 mL). After stirring at 0° C. for 15 min, a small crystal of urea was added and the resulting mixture was added slowly to 20% sulfuric acid (85 mL) at 90° C. Heating was continued for an additional 30 min, the mixture was cooled, and the pH was adjusted to 7 with potassium carbonate (solid). The mixture was extracted with dichloromethane (2×100 mL) and the organic layer was washed with brine, dried (MgSO$_4$) and concentrated in vacuo. Purification by column chromatography and eluting with hexanes/ethyl acetate (1:1)+3% methanol, afforded 1.44 g (60%) of the title product. $^1$H NMR (500 MHz, CD$_3$OD): δ 7.88 (d, J=2.5 Hz, 1H), 7.39–7.28 (m, 5H), 6.89 (d, J=2.5 Hz, 1H), 3.70 (s, 2H), 3.58 (s, 2H), 2.89–2.81 (m, 4H).

Step E

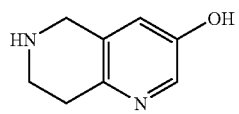

A mixture of the intermediate from Step D (1.45 g), ethanol (25 mL), 2 N HCl (5.0 mL) and Pd/C (100 mg, 10%) was hydrogenated at room temperature for 24 h and the resulting mixture was filtered through celite. The catalyst was washed thoroughly with hot ethanol and the filtrate was concentrated in vacuo to yield 1.2 g of the desired product as the HCl salt. $^1$H NMR (500 MHz, CD$_3$OD): δ 8.29 (d, J=2.6 Hz, 1H), 7.87 (d, J=2.3 Hz, 1H), 4.57 (s, 2H) 3.68 (t, J=6.5 Hz, 2H), 3.37 (t, J=6.2 Hz, 2H).

Step F

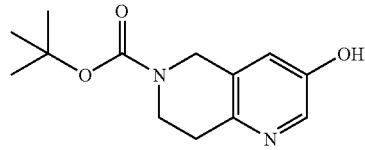

To a solution of the amine intermediate from Step E (1.20 g, 5.3 mmol) in 40 mL of water/dichloromethane (1:1) was added di-tert-butyl dicarbonate (1.40 g) followed by sodium bicarbonate (2.25 g). The mixture was stirred vigorously at room temperature for 4 h. The layers were separated and the aqueous layer was washed with dichloromethane (×2). The combined dichloromethane layers were dried (MgSO$_4$), concentrated and chromatographed. Eluting with hexanes/ethyl acetate (1:1)+5% methanol gave 0.91 g (68%) of the title product $^1$H NMR (500 MHz, CD$_3$OD): δ 7.91 (d, J=2.5 Hz, 1H), 7.01 (d, J=2.9 Hz, 1H), 4.53 (s, 2H), 3.72 (t, J=5.5 Hz, 2H), 2.83 (t, J=6.0 Hz, 2H), 1.48 (s, 9H).

INTERMEDIATE 11

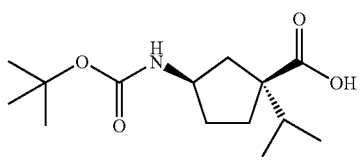

A mixture of (1S)-(+)-2-azabicyclo[2.2.1]hept-5-en-3-one (10.3 g, 94.4 mmol) in ethyl acetate (200 mL) and 10% Pd/C (0.5 g), was hydrogenated at room temperature. After 24 h the reaction mixture was filtered and evaporated leaving behind 10.4 g (100%) of the product that was taken in 250 mL methanol and HCl (12 M, 6 mL). The resultant mixture was stirred at room temperature, until the reaction was complete (72 h). Evaporation of methanol followed by drying under high vacuum, yielded title compound as an off white solid (16.0 g, 96%). $^1$H NMR (500 MHz, D$_2$O): δ 3.70 (s, 3H), 3.01 (m, 1H), 2.38 (m, 1H), 2.16–1.73 (m, 6H).

Step B

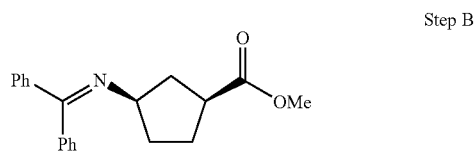

To a suspension of the intermediate from Step A (10.2 g, 56.8 mmol) in dry dichloromethane (200 mL) was added benzophenone imine (10.2 g, 56.8 mmol) at room temperature and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under vacuum to yield the title compound (18.03 g, >100%) and required no further purification. 1H NMR (500 MHz, CDCl3): δ 7.5–7.18 (m, 10H), 3.75 (m, 1H), 3.7 (s, 3H), 2.78 (m, 1H), 2.26–1.71 (m, 6H).

Step C

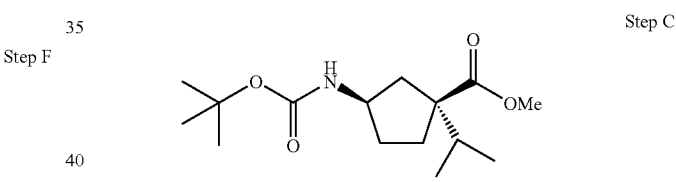

To a solution of lithium diisopropylamide (prepared from diisopropylamine (7.7 g, 76 mmol) and n-butyllithium (30.4 mL, 2.5 M in hexanes, 76 mmol) in tetrahydrofuran (120 mL) at −78° C. was added the ester from step B (18.0 g, 58.6 mmol). The resultant burgundy colored solution was stirred for 20 min after which it was quenched with 2-iodopropane (14.9 gm, 88 mmol). The reaction mixture was gradually warmed over 3 h to 0° C. and this temperature was maintained for an additional 3 h. Reaction was quenched with water and extracted with ethyl acetate. The organic layer was washed with water, brine, dried (anhydrous magnesium sulfate) and concentrated to yield an oil. To the solution of the crude Schiff base (20.0 g) in tetrahydrofuran (100 mL) was added HCl (5.0 mL, 12 M). The resulting reaction mixture was allowed to stir at room temperature for 3 h. After the removal of all volatiles, the hydrochloride salt was taken up into dichloromethane (250 mL), saturated solution of sodium bicarbonate (250 mL) and di-tert-butyl dicarbonate (26.0 g, 1.4 Eq.) were added. The resultant mixture was vigorously stirred overnight at room temperature. The organic layer was separated and washed with water, brine, dried (anhydrous magnesium sulfate) and concentrated to yield an oil. Purification by flash column chromatography (eluent: hexanes/ethyl acetate 19:1) gave the desired product (4.91 g, 30%). 1H NMR (500 MHz, CDCl3): 4.79 (br, 1H), 4.01 (m, 1H), 3.71 (s, 3H), 2.18–1.60 (m, 6H), 1.44 (s, 9H), 0.87 (d, J=6.9 Hz, 3H), 0.86 (d, J=6.9 Hz, 3H).

Step D

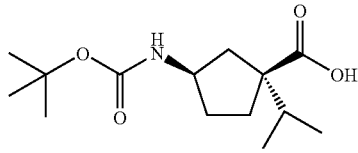

To a solution of the ester from Step C (4.91 g, 17.2 mmol) in methanol (100 mL) was added a solution of LiOH (3.6 g, 85 mmol) in water (20 mL) and tetrahydrofuran (10 mL). The resultant mixture was heated at 80° C. until the reaction was complete (18 h). The methanol was removed in vacuo and the crude product was taken up with water/ethyl acetate (200 mL, 1:4) and cooled to 0° C. The acidity of the mixture was adjusted to pH 6. The ethyl acetate layer was separated, washed with water, brine, dried (anhydrous magnesium sulfate) and concentrated to yield an oil. Purification by flash column chromatography (eluent: hexanes/ethyl acetate 1:1+ 2% AcOH) gave Intermediate 11 (3.9 g, 84%). 1H NMR (500 MHz, CDCl3): 11.36 (br, 1H), 6.49 (br, 1H), 4.83 (m, 1H), 3.71 (s, 3H), 2.30–1.55 (m, 6H), 1.46 (s, 9H), 0.94 (d, J=6.9 Hz, 3H), 0.933 (d, J=6.9 Hz, 3H).

Procedure B:

Step A:

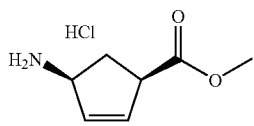

Commercially available (1R,4S)-4-aminocyclopent-2-ene-1-carboxylic acid was converted to its methyl ester hydrochloride salt via classical procedures.

Step B:

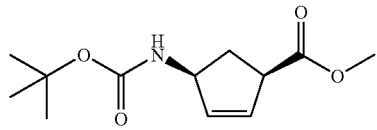

To a suspension of amine from Step A (6.31 g, 35.5 mmol) in acetone (40 mL) and water (20 mL) was added solid NaHCO$_3$ (6.6 g, 78 mmol) in portions. After 5 min, a solution of di-tert-butyl dicarbonate (8.5 g, 39 mmol) in acetone (60 mL) was added and the reaction mixture was stirred at room temperature. After 3 h, acetone was removed in vacuo and the residue was partitioned between ether (500 mL) and saturated aqueous NaHCO$_3$ solution (120 mL). The ether layer was further washed with aqueous NaHCO$_3$ solution (1×100 mL), brine (1×100 mL), dried over anhydrous Na$_2$SO$_4$, concentrated and purified by flash chromatography (15% ethyl acetate/hexanes) to afford the product (7.25 g, 85%).

Step C:

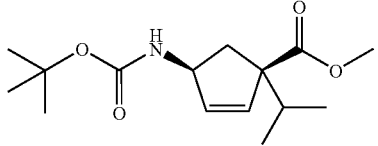

To a solution of lithium bis(trimethylsilyl)amide (10.4 g, 62.1 mmol) in tetrahydrofuran (100 mL) was added a solution of the intermediate from Step B (6.71 g, 27.8 mmol) in tetrahydrofuran (10 mL) over 10 min at −78° C. The resulted solution was stirred at −78° C. for 30 min before isopropyl iodide (3.3 mL, 33 mmol) was added in one portion. The reaction was allowed to warm up to −25° C. and this temperature was maintained overnight. The reaction was then quenched with an aqueous saturated NH$_4$Cl solution (250 mL). The organic layer was separated and the aqueous layer was further extracted with diethyl ether (3×100 mL). The combined organic layers were then washed with brine (1×100 mL), dried over anhydrous Na$_2$SO$_4$, filtered, concentrated and purified by flash chromatography (5–10% ethyl acetate/hexanes) to give the product (5.66 g, 72%) as a clear oil (cis/trans=4.3/1). $^1$H NMR (500 MHz, CDCl$_3$) cis-isomer: δ 5.79 (s, 2H), 4.75 (m, 1H), 3.72 (s, 3H), 2.28–2.20 (m, 2H), 2.0 (dd, J=15.4 Hz, 1H), 1.45 (s, 9H), 0.85 (d, J=6.6 Hz, 3H), 0.81 (d, J=7 Hz, 3H).

Step D:

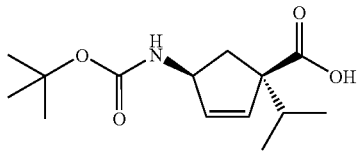

To a solution of the product from step C (1.6 g, 5.7 mmol) in tetrahydrofuran (50 mL), methanol (50 mL) and water (10 mL) was added LiOH monohydrate (400 mg) and the reaction was heated to reflux overnight until the TLC indicated that the reaction was complete. The organic solvents were removed in vacuo and the aqueous layer was washed with ether (1×) and then acidified slowly with concentrated HCl until the pH reached 4. The resulting suspension was extracted with CH$_2$Cl$_2$ (3×). The combined organic layers were dried over anhydrous MgSO$_4$, filtered and concentrated to give the product as a mixture of two cis/trans isomers (1.5 g) as a foaming yellow solid. This solid was dissolved in ethyl acetate (2 mL) with heating and diluted with hexanes (50 mL) to give a clear solution. This solution was allowed to cool to room temperate slowly over 1 h and then maintained at −25° C. in a freezer overnight. The trans-isomer was crystalized out along with some of the desired cis-isomer (500 mg total). The mother solution was collected and concentrated to give the title compound (1 g, 66%, cis-isomer only). $^1$H NMR (500 MHz, CDCl$_3$) cis-isomer: δ 5.80 (m, 2H), 4.80 (m, 1H), 2.40–2.20 (m, 2H), 2.15–2.0 (m, 1H), 1.5 (m, 9H), 1.0–0.8 (m, 3H).

Step E:

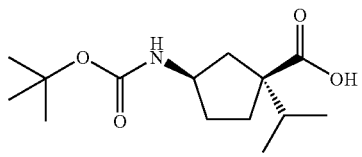

To a solution of the product from Step D (1 g) in ethanol (30 mL) was added 10% Pd/C (100 mg) and the resulting mixture was agitated on a Parr apparatus at 50 lb pressure of H2 overnight. The mixture was filtered through celite and concentrated in vacuo to afford the title compound (1 g, 99%). 1H NMR (500 MHz, CDCl3): 11.36 (br, 1H), 6.49 (br, 1H), 4.83 (m, 1H), 3.71 (s, 3H), 2.30–1.55 (m, 6H), 1.46 (s, 9H), 0.94 (d, J=6.9 Hz, 3H), 0.933 (d, J=6.9 Hz, 3H).

INTERMEDIATE 12

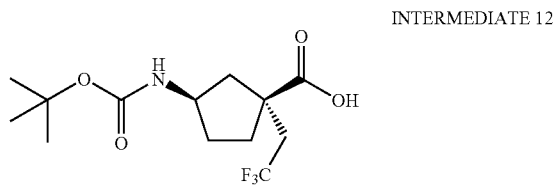

Step A:

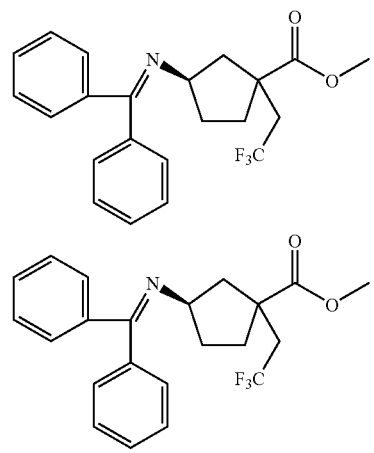

A flame dried 1000 mL round bottom flask was charged with 400 mL of dry tetrahydrofuran, and then, set under nitrogen and cooled to –78° C. using an acetone/dry ice bath. Diisopropylamine (27.4 mL, 195 mmol) was added to the cooled solvent via a syringe. The resulting solution was slowly treated with 2.5 M n-butyllithium in hexanes (55 mL, 140 mmol). After 5 min stirring, the product described in Step B, Intermediate 11 (40 g, 130 mmol) in 100 mL of tetrahydrofuran was added dropwise via syringe and the resulting mixture was stirred at –78° C. for 2 h. 2-iodo-1, 1,1-trifluoroethane (47 mL, 480 mmol) was then added dropwise via syringe and the resulting mixture was stirred overnight allowing it to warm slowly to room temperature. The reaction was quenched with a saturated solution of ammonium chloride (400 mL) and the organics were separated. The aqueous layer was extracted with ethyl acetate (3×150 mL) and all the organics were combined, dried over anhydrous sodium sulfate, filtered, and evaporated under reduced pressure. The crude product was used in the next step without further purification. LC-MS for $C_{22}H_{22}F_3NO_2$ calculated 389.26, found [M+H$^+$] 390.4

Step B

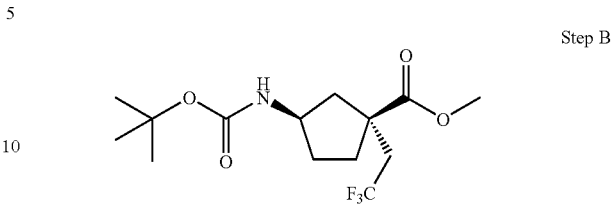

To a solution of the product from Step A, Intermediate 12 (130 mmol, assuming 100% conversion) in 200 mL of tetrahydrofuran was added 200 mL of 2 N hydrochloric acid and the resulting mixture was stirred overnight at room temperature. The solution was concentrate in vacuo to remove the tetrahydrofuran and the aqueous layer was then diluted with dichloromethane (300 mL). The pH of the aqueous layer was adjusted to a pH of 10 by the slow addition of 5 N sodium hydroxide with vigorous stirring. The organic layer was removed using a separatory funnel and the aqueous layer was extracted with dichloromethane (2×150 mL). The organic layers were combined, dried over anhydrous sodium sulfate, and filtered. To the filtrate was added diisopropylethylamine (22.7 mL, 130 mmol) and di-tert-butyl dicarbonate (32.7 g, 150 mmol) and the resulting solution was stirred at room temperature overnight. The mixture was washed with 1 N hydrochloric acid, followed by a saturated solution of sodium bicarbonate, and brine. The organic layer was dried over anhydrous sodium sulfate, filtered, and evaporated under reduced pressure. Purification by MPLC (5 g per run) afforded 5.87 g (14%) of the desired cis (R, S) isomer and 12.31 g (29%) of the undesired trans (S, S) isomer. Also, 5.22 g (12%)was recovered as a 1:1 mixture of the 2 diastereomers. $^1$H NMR (500 MHz, CDCl$_3$) δ (1$^{st}$ desired isomer) 5.05 and 4.40 (singlets, 1H), 3.76 (s, 3H), 2.73 (ddd, J=11.0, 12.8, 14.8 Hz, 1H), 2.38 (ddd, J=10.7, 12.8, 15.0 Hz, 1H) 2.32–2.26 (m, 1H), 2.21 (br dd, J=3.6, 14.5 Hz, 1H), 2.18–2.11 (m, 1H), 2.02 (d, J=8.8, 14.4 Hz, 1H), 1.61 (dd, J=7.8, 13.2 Hz, 1H) 1.52 (br s, 10H). $^1$H NMR (500 MHz, CDCl$_3$) δ (2$^{nd}$ undesired isomer) 4.52 and 4.06 (singlets, 1H), 3.72 (s, 3H), 2.72 (dd, J=7.1, 13.5 Hz, 1H), 2.66 (ddd, J=10.6, 12.8, 15.0 Hz, 1H), 2.53 (ddd, J=11.0, 12.8, 14.9 Hz, 1H) 2.26 (app dd, J=7.1, 13.5 Hz, 1H), 2.18–2.07 (m, 1H), 1.78 (dd, J=8.6, 13.5 Hz, 1H), 1.57–1.48 (m, 2H) 1.46 (s, 9H).

Step C

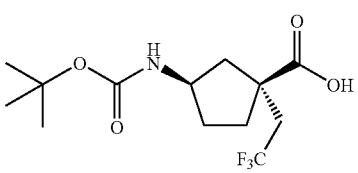

To a mixture of the desired cis (R,S) product described in Step B, Intermediate 12 (4.0 g, 12 mmol) in a 1:1:1 solution of tetrahydrofuran/methanol/water (84 mL) was added solid LiOH (2.60 g, 62.0 mmol) and the resulting solution was heated to 60° C. and stirred for 18 h. The mixture was left standing to cool to room temperature and then concentrated to remove the organic solvent. The aqueous layer was acidified by the slow addition of 6 N hydrochloric acid to pH 4-5. The acidic aqueous layer was extracted with dichloromethane (3×100 mL) and the organics were combined, dried over anhydrous sodium sulfate, filtered, and evaporated under reduced pressure to afford Intermediate 12 (3.86 g, 99%) as a yellow oil. After two days standing at 5° C. in the refrigerator, the material crystallized.

INTERMEDIATE 13

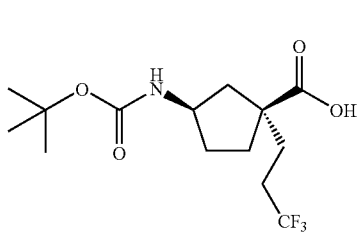

This intermediate was prepared in an analogous fashion to Intermediate 12, except 2-iodo-1,1,1-trifluoroethane was replaced with 3-iodo-1,1,1-trifluoropropane. Purification by MPLC (gradient eluant 0–40% ethyl acetate/hexanes) afforded 612 mg (11%) of the desired cis (R, S) isomer (Intermediate 13) and 905 g (17%) of the undesired trans (S, S) isomer.

INTERMEDIATE 14

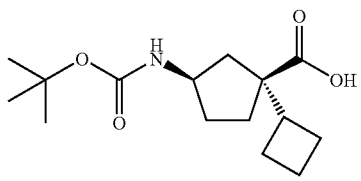

This intermediate was prepared in an analogous fashion to Intermediate 12, except 2-iodo-1,1,1-trifluoroethane was replaced with cyclobutyl bromide. Purification by MPLC (gradient eluant 0–30% ethyl acetate/hexanes) afforded 103 mg (5%) of the desired cis (R, S) isomer (Intermediate 14). The more polar trans isomer was not collected. $^1$H NMR (500 MHz, CDCl$_3$) δ 4.85 and 4.10 (singlets, 1H), 2.28–2.21 (m, 1H), 2.13 (dd, J=5.0, 14.0 Hz, 1H) 2.10–2.04 (m, 1H), 1.99 (dd, J=8.0, 13.7 Hz, 1H), 1.68–1.56 (m, 2H), 1.53 (dd, J=7.2, 13.6 Hz, 1H), 1.46 (br s, 10H), 0.64–0.56 (m, 1H), 0.46–0.37 (m, 2H), 0.08–0.01 (m, 2H).

INTERMEDIATE 15

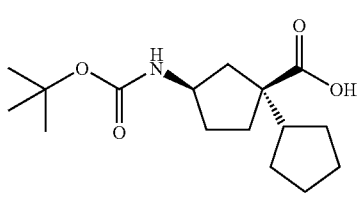

This intermediate was prepared in an analogous fashion to Intermediate 12, except 2-iodo-1,1,1-trifluoroethane was replaced with iodocyclopropane. Purification by MPLC (gradient eluant of 0–25% ethyl acetate/hexanes) afforded 506 mg (20%) of the desired cis (R, S) isomer (Intermediate 15) and 803 g (32%) of the undesired trans (S, S) isomer. $^1$H NMR (500 MHz, CDCL3) δ $^1$H NMR (500 MHz, CDCL3) δ (1$^{st}$ desired isomer) 4.80 and 4.02 (singlets, 1H), 2.27 (ddd, J=8.0, 9.7, 17.8 Hz, 1H), 2.19 (ddd, J=4.4, 7.4, 12.4 Hz, 1H) 2.07–1.96 (m, 3H), 1.95 (br dd, J=8.2, 14.0 Hz, 1H) 1.68–1.50 (m, 8H), 1.45 (br s, 10H), 1.25–1.17 (m, 1H). $^1$H NMR (500 MHz, CDCl$_3$) δ (2$^{nd}$ undesired isomer) 4.56 and 3.90 (singlets, 1H), 2.58 (dd, J=7.1, 13.0 Hz, 1H), 2.22 (ddd, J=8.0, 9.6, 17.7 Hz, 1H) 2.11 (ddd, J=7.5, 7.6, 13.3 Hz, 1H) 2.04–1.93 (m, 1H), 1.68–1.45 (m, 7H), 1.44 (br s, 10H), 1.38–1.15 (m, 4H).

INTERMEDIATE 16

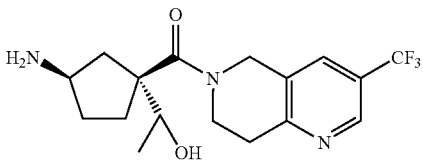

Step A:

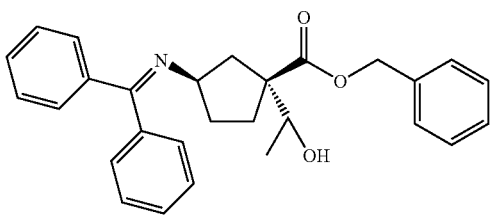

A solution of diisopropylamine (2.70 mL, 19.3 mmol) in tetrahydrofuran (20 mL) was cooled to −78° C. and a solution of n-butyllithium in hexanes (7.70 mL, 2.5 M, 19.3 mmol) was added via syringe, followed by a solution of the Schiff base, from Step C, Intermediate 9 (5.685 g, 14.82 mmol) in tetrahydrofuran (10 mL). The enolate was allowed to form for 3 h at −78° C., after which time the neat acetaldehyde (1.00 mL, 29.7 mmol) was added. The reaction was quenched with the addition of aqueous citric acid (200 mL, 10%) and the crude product was extracted into diethyl ether. Drying (anhydrous magnesium sulfate) and evaporation of the solvent gave the crude desired product (6.16 g). This was further purified by flash chromatography (deactivated silica gel, ethyl acetate/hexanes 3:7) to yield the desired cis-isomer (2.32 g, 54%). This Schiff base was found to be unstable, and was used in the next step without delay. LC-MS for C$_{28}$H$_{29}$NO$_3$ calculated: 427.21, found [M+H]$^+$ 428.20.

Step B:

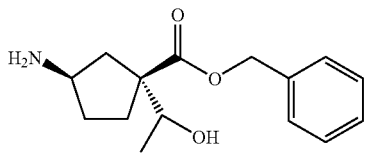

The Schiff base from Step A (2.323 g, 5.433 mmol) was dissolved in tetrahydrofuran (20 mL) and 2 N HCl was added. The reaction mixture was stirred at room temperature for 2 h, after which time the volatiles were removed in vacuo. The resulting mixture of the desired amine hydrochloride and benzophenone was used in the next step without further purification.

Step C:

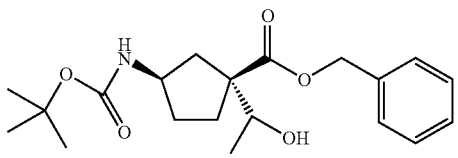

The crude product from the previous step (max 5.433 mmol) was dissolved in dichloromethane (50 mL), di-tert-butyl dicarbonate (2.371 g, 10.87 mmol) was added followed by 50 mL of a saturated solution of sodium bicarbonate. The reaction mixture was vigorously stirred at room temperature for 1 h. The layers were separated and the aqueous phase was washed with dichloromethane. The combined organic extracts were dried (anhydrous magnesium sulfate) and the solvent was evaporated in vacuo. Final purification by gradient flash chromatography (ethyl acetate/hexanes 0–40%) gave the desired BOC-protected amine (619 mg, 32%, two steps) as a mixture (3:2) of two diasteromers. LC-MS for $C_{20}H_{29}NO_5$ calculated: 363.20, found 264.20 ([M+H]$^+$—loss of the BOC group).

Step D:

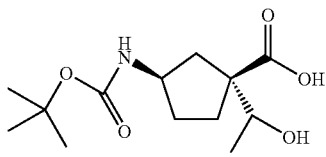

This acid was prepared following the procedure described in Intermediate 12, Step C, and was used in the next step without further purification.

Step E:

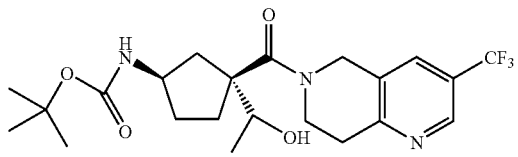

A solution of the acid from the previous step (809 mg, 2.96 mmol), Intermediate 8 (1.63 g, 5.92 mmol), 1-hydroxy-7-azobenzotriazole (402 mg, 2.96 mmol), and diisopropylethylamine (1.0 mL, 5.9 mmol) in dichloromethane (25 mL) was treated with 1-(-3-dimethylaminopropyl)-3-ethylcarbodiimide hydrochloride (1.70 g, 8.88 mmol) and the resulting mixture was stirred at room temperature overnight. The reaction was quenched with water, and the product was extracted into dichloromethane. The combined organic extracts were dried (anhydrous magnesium sulfate) and the solvent was removed in vacuo. The residue (679 mg) was separated by MPLC (eluant gradient 40–100% ethyl acetate/hexanes) to yield a single isomers (the hydroxyethyl side-chain) of unknown absolute stereochemistry. $^1$H NMR (CDCl$_3$, 500 MHz) indicated a mixture of isomeric alcohols in a ratio of about 2 to 3. LC-MS for $C_{22}H_{30}F_3N_3O_4$ calculated: 457.22, found 358.20 ([M+H]$^+$–loss of the BOC group).

Step F:

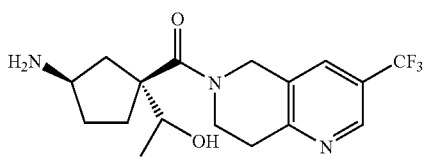

The solution of the of the higher eluting diastereoisomer from the previous step (282 mg, 0.618 mmol) in dichloromethane (6 mL) was treated with TFA (4 mL) and the resulting mixture was stirred at room temperature for 2 h. The volatiles were removed in vacuo to yield 218 mg (99%) of the crude product. LC-MS for $C_{17}H_{22}F_3N_3O_2$ calculated: 357.17, found [M+H]$^+$ 358.10.

INTERMEDIATE 17

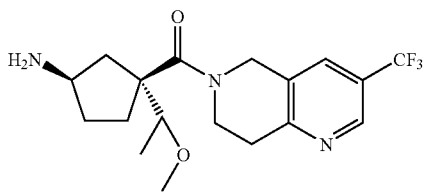

Step A:

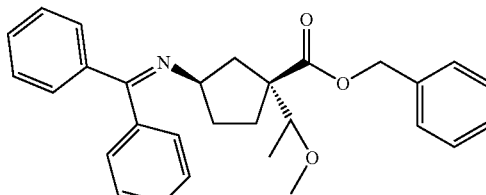

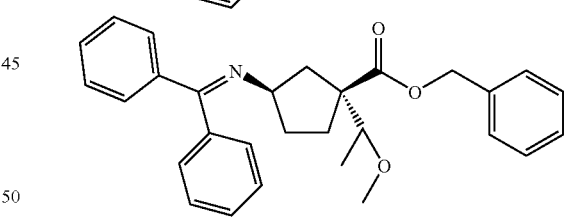

A flame dried round bottom flask was charged with NaH (15 mg, 60% suspension, 0.4 mmol) and set under static nitrogen. N,N-dimethylformamide (2.0 mL) was added via syringe, and the mixture was cooled to 0° C. While stirring, a solution of the benzyl ester from Step A, Intermediate 16 (higher eluting (1,3-cis-) diastereoisomeric pair, 142 mg, 0.332 mmol) and methyl iodide (142 μL, 1.00 mmol) were added via syringe. The cooling bath was removed and the mixture was stirred at room temperature for 3 h. The reaction was quenched by pouring onto water and the crude product was extracted with a mixture of hexanes and ether (1:1). The combined organic extracts were backwashed with water, dried (anhydrous sodium sulfate) and the solvent was evaporated in vacuo to leave 106.3 mg (73%) of crude product. The two respective diastereoisomers were separated by gradient flash chromatography (eluent: 0–40% of ethyl acetate/hexanes). LC-MS for $C_{29}H_{31}NO_3$ calculated 441.23, found $[M+H]^+$ 442.30.

Step B

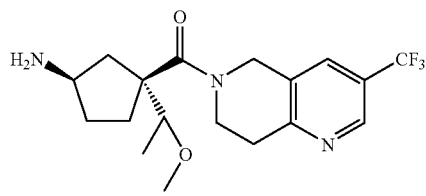

This amine was synthesized starting from the product of Step A in a series of reactions analogous to those described in Intermediate 16, Steps B–F.

INTERMEDIATE 18

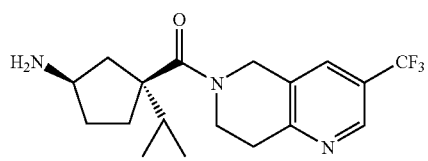

This intermediate was prepared in an analogous fashion to Intermediate 16, except acetaldehyde was replaced with propionaldehyde. Purification by MPLC (gradient eluant 40–100% ethyl acetate/hexanes) afforded single isomers (the hydroxypropyl side-chain) of unknown absolute stereochemistry (total yield of all 312 mg, 41%). Isomer 1: $^1$H NMR (500 MHz, CDCl$_3$) δ 5.0 (br s, 1H), 4.08 (br. S, 1H), 3.60 (ddd, J=2.0, 7.9, 9.8 Hz, 1H), 2.50–2.42 (m, 2H), 2.10–1.88 (m, 4H), 1.64–1.52 (m, 2H), 1.45 (s overlapped, 9H), 1.65 (s, 1H) 1.48–1.36 (m, 1H), 1.29–1.22 (m, 1H), 0.98 (t, J=7.3 Hz, 3H). Isomer 2: $^1$H NMR (500 MHz, CDCl$_3$) δ 4.76 (br s, 1H), 4.08 (br s, 1H), 3.63–3.55 (m, 1H), 2.26 (dd, J=7.8, 14.0 Hz, 1H), 2.22–2.15 (m, 1H), 2.06–1.94 (m, 2H), 1.91 (dd, J=5.4, 14.1 Hz, 1H), 1.76–1.68 (m, 1H), 1.60 (s, overlapped, 1H)1.60–1.50 (m, 2H), 1.45 (s, overlapped, 9H), 1.48–1.38 (m, 1H), 1.30–1.20 (m, 1H), 0.98 (t, J=7.2 Hz, 3H). Isomer 3: $^1$H NMR (500 MHz, CDCl$_3$) δ 4.82 (br s, 1H), 4.09 (br s, 1H), 3.43 (d, J=9.8 Hz, 1H), 2.19 (s, 1H), 2.11 (ddd, J=4.8, 7.2, 12.7 Hz, 1H), 2.06–1.90 (m, 6H), 1.45 (s, overlapped, 9H), 1.54–1.40 (m, 1H), 1.28–1.18 (m, 1H), 0.99 (t, J=7.1 Hz, 3H). Isomer 4: $^1$H NMR (500 MHz, CDCl$_3$) δ 4.83 (br s, 1H), 4.04 (br s, 1H), 3.59 (app br t, J=8.1 Hz, 1H), 2.55 (br dd, J=7.1, 13.7 Hz, 1H), 2.39 (br d, J=7.1 Hz, 1H), 2.18 (s, 1H), 2.14–2.06 (m, 1H), 2.02–1.91 (m, 2H), 1.90–1.82 (m, 1H), 1.72–1.65 (m, 1H), 1.59–1.50 (m, 1H), 1.44 (s, overlapped, 9H), 1.47–1.37 (m, 1H), 1.26–1.17 (m, 1H), 0.96 (t, J=7.3 Hz, 3H).

INTERMEDIATE 19

-continued

Step A

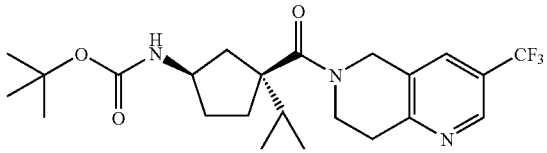

Intermediate 8 (4.6 g, 16 mmol) and Intermediate 11 (4.0 g, 14 mmol) were first dried by azeotropic distillation with toluene (3×50 mL) and placed under high vacuum for 30 min. Under nitrogen, 4-dimethylaminopyridine (1.08 g, 8.60 mmol), anhydrous dichloromethane (40 mL), and diisopropylethylamine (7.0 mL, 40 mmol) were added sequentially. After Intermediate 8 was in solution, bromo-tris-pyrrolidino-phosphonium hexafluorophosphate (6.80 g, 14.3 mmol) was added, immediately followed by additional diisopropylethylamine (7.0 mL, 40 mmol). The reaction mixture was stirred at room temperature overnight and then quenched with saturated NaHCO$_3$. The aqueous layer was back washed with dichloromethane (3×50 mL) and the organic layers were combined, dried over Na$_2$SO$_4$, filtered, and evaporated in vacuo. The crude product was purified by flash chromatography (stepwise gradient 0–60%, ethyl acetate/hexanes) to afford the product (4.80 g, 74%) as a yellow foam. $^1$H NMR (500 MHz, CDCL$_3$) δ 8.72 (s, 1H), 7.70 (s, 1H), 4.88 (br d, J=17.0 Hz, 1H), 4.78 (d, J=17.6 Hz, 1H), 4.04–3.84 (m, 2H), 3.52 (br s, 1H), 3.12 (br t, J=5.6 Hz, 1H), 2.32–2.06 (m, 3H), 1.98–1.70 (m, 4H), 1.64–1.54 (m, 1H), 1.44 (s, 9H), 0.92–0.82 (m, 6H). LC-MS for $C_{23}H_{32}F_3N_3O_3$ calculated 455.24, found $[M+H]^+$ 456.2.

Step B:

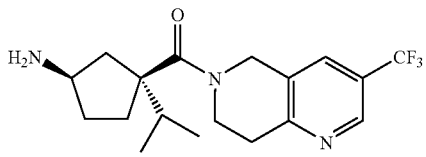

The from Step B, Intermediate 19 (1.2 g, 2.6 mmol) was dissolved with 4 N HCl in dioxane (50 mL) and the resulting solution was stirred at room temperature for 1 h. The reaction was evaporated under vacuum to afford the product (904 mg, 97%) as a white powder. LC-MS calculated for $C_{18}H_{24}F_3N_3O$ is 355.20, found $[M+H]^+$ 356.2.

INTERMEDIATE 20

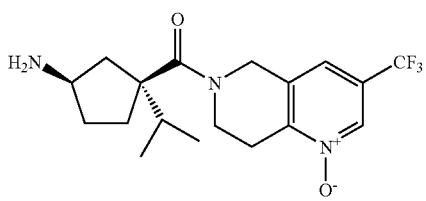

Step A:

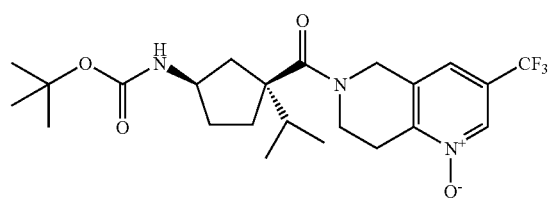

To a solution of the product described in Step A, Intermediate 19 (2.0 g, 4.4 mmol) in dichloromethane (80 mL) was added 3-chloroperoxybenzoic acid (2.11 g, 8.83 mmol) and the resulting solution was stirred overnight at room temperature. The mixture was cooled to 0° C. and while stirring vigorously, solid calcium hydroxide was added in portions (about 6 g). The suspension was stirred for an additional 30 min, then filtered through celite to remove all solids. The filtrate was evaporated in vacuo and the residue was purified by MPLC (gradient eluant 40–100% ethyl acetate/hexanes) to afford 1.32 g (64%) of the desired compound. $^1$H NMR (500 MHz, CDCL$_3$) δ 8.46 (s, 1H), 7.28 (s, 1H), 4.88 (br d, J=17.2 Hz, 1H), 4.78 (d, J=17.7 Hz, 1H), 4.05–3.84 (m, 2H), 3.12 (br s, 1H), 2.34–2.06 (m, 3H), 1.88–1.70 (m, 4H), 1.62–1.54 (m, 1H), 1.43 (s, 9H), 0.90–0.85 (m, 6H). LC-MS for $C_{23}H_{32}F_3N_3O_5$ calculated 471.20, found [M+H]$^+$ 472.2.

Step B:

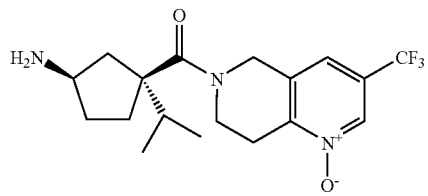

The product from Step B, Intermediate 20 (1.32 g, 2.82 mmol) was dissolved in 4 N HCl in dioxane (50 mL) and the resulting solution was stirred at room temperature for 1 h. The reaction was evaporated under vacuum to afford the product (1.10 g, 98%) as a white powder. LC-MS for $C_{18}H_{24}F_3N_3O_2$ calculated 371.20, found [M+H]$^+$ 372.2.

INTERMEDIATE 21

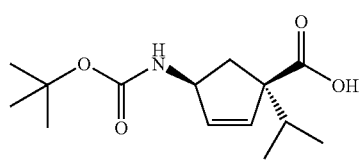

Step A:

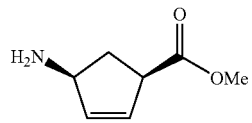

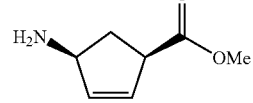

Thionyl chloride (20.1 mL, 275 mmol) was slowly introduced to 175 mL of methanol and the resulting solution was allowed to stir for 10 min. To this solution, (1R,4S)-4-amino-cyclopent-2-ene (10 g, 79 mmol) was added and the mixture was heated to reflux for 15 h. After allowing to cool to room temperature, the solution was evaporated in vacuo to afford the crude product (13.95 g, 99%) which was used in the next step without further purification.

Step B:

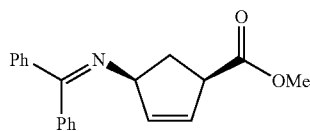

To a suspension of the intermediate from Step A (13.9 g, 78.8 mmol) in dry dichloromethane (100 mL) was added benzophenone imine (13.5 g, 78.5 mmol) at room temperature and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under high vacuum to yield the title compound (18.03 g, >100%) and required no further purification. $^1$H NMR (500 MHz, CDCl$_3$): δ 7.64 (d, J=7.1 Hz, 2H), 7.52–7.44 (m, 3H), 7.38 (t, J=7.1 Hz, 1H), 7.33 (t, J=7.1 Hz, 2H), 7.20 (d, J=7.1 Hz, 2H), 5.97 (ddd, J=2.1, 4.1, 5.7 Hz, 1H), 5.78 (ddd, J=2.3, 4.8, 5.5 Hz, 1H), 4.52 (br ddd, J=2.1, 5.3, 7.3 Hz, 1H), 3.74 (s, 3H), 3.52 (ddd, J=2.2, 5.95, 8.4 Hz, 1H), 2.40–2.33 (m, 1H), 2.29–2.22 (m, 1H).

Step C

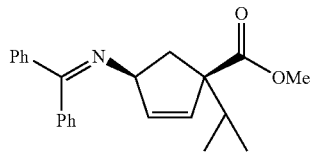

A flame dried 500 mL round bottom flask was charged with 100 mL of dry tetrahydrofuran, and then, set under nitrogen and cooled to −78° C. using an acetone/dry ice bath. Diisopropylamine (2.74 mL, 19.5 mmol) was added to the cooled solvent via syringe. 2.5 M n-butyllithium in hexanes (7.80 mL, 19.50 mmol) was then added slowly to the solution. After 5 min stirring, the product described in Step B, Intermediate 21 (5.0 g, 16 mmol) in 30 mL of tetrahydrofuran was added dropwise via syringe and the resulting mixture was stirred at −78° C. for 2 h. 2-iodopropane (2.26 mL, 22.8 mmol) was then added dropwise via syringe and the resulting mixture was stirred overnight allowing it to warm slowly to room temperature. The reaction was quenched with a saturated solution of ammonium chloride (100 mL) and the organic layer was separated. The aqueous layer was extracted with ethyl acetate (3×100 mL) and all the organics were combined, dried over anhydrous sodium sulfate, filtered, and evaporated under reduced pressure. The crude product was used in the next step without further purification. LC-MS for $C_{23}H_{25}NO_2$ calculated 347.19, found $[M+H]^+$ 348.2.

Step D:

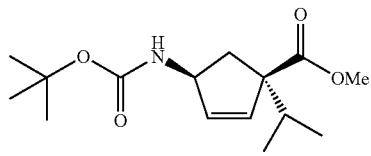

To a solution of the product from Step C, Intermediate 21 (16.25 mmol, assuming 100% conversion) in 100 mL tetrahydrofuran was added 100 mL of 2 N hydrochloric acid and the resulting mixture was stirred overnight at room temperature. The solution was concentrate in vacuo to remove the tetrahydrofuran and the aqueous layer was then diluted with dichloromethane (300 mL). The pH of the aqueous layer was adjusted to 10 by the slow addition of 5 N sodium hydroxide with vigorous stirring. The organic layer was removed using a separatory funnel and the aqueous layer was extracted with dichloromethane (2×150 mL). The organics were combined, dried over anhydrous sodium sulfate, and filtered. To the filtrate was added diisopropylethylamine (2.83 mL, 16.25 mmol) and di-tert-butyl dicarbonate (4.26 g, 19.5 mmol) and the resulting solution was stirred at room temperature overnight. The mixture was washed with 1 N hydrochloric acid, followed by a saturated solution of sodium bicarbonate, and brine. The organic layer was dried over anhydrous sodium sulfate, filtered, and evaporated under reduced pressure. Purification by MPLC (gradient eluant: 0–25% ethyl acetate/hexanes) afforded 1.58 g (34%) of the desired cis (R, S) isomer and 1.37 g (30%) of the undesired trans (S, S) isomer.

Step E:

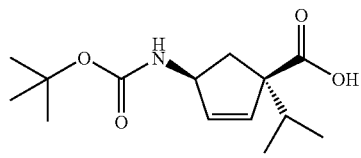

To a mixture the desired cis (R, S) product described in Step D, Intermediate 21 (1.51 g, 5.33 mmol) in a 1:1:1 solution of tetrahydrofuran/methanol/water (60 mL) was added solid LiOH (1.12 g, 26.7 mmol) and the resulting solution was heated to 60° C. and stirred for 18 h. The mixture was left standing to cool to room temperature and then concentrated to remove the organic solvent. The aqueous layer was acidified by the slow addition of 6 N hydrochloric acid to adjust the pH to 4 or 5. The acidic aqueous layer was extracted with dichloromethane (3×100 mL) and the organics were combined, dried over anhydrous sodium sulfate, filtered, and evaporated under reduced pressure to afford Intermediate 21 (1.30 g, 91%) as a yellow oil. After two weeks standing at room temperature, the material solidified.

INTERMEDIATE 22

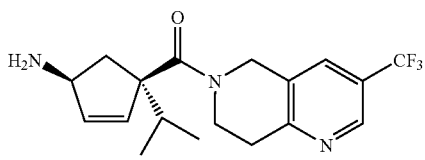

This intermediate was prepared in an analogous fashion to Intermediate 19, except Intermediate 11 was replaced with Intermediate 21. LC-MS for $C_{18}H_{22}F_3N_3O$ calculated 353.17, found $[M+H]^+$ 354.2.

INTERMEDIATE 23

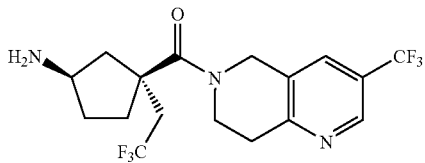

This intermediate was prepared in an analogous fashion to Intermediate 19, except Intermediate 11 was replaced with Intermediate 12. LC-MS for $C_{17}H_{19}F_6N_3O$ calculated 395.17, found $[M+H]^+$ 396.2.

INTERMEDIATE 24

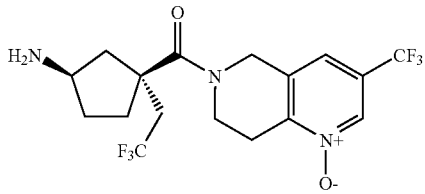

This intermediate was prepared in an analogous fashion to Intermediate 20, except Intermediate 11 was replaced with Intermediate 12. LC-MS for $C_{17}H_{19}F_6N_3O_2$ calculated 411.17, found $[M+H]^+$ 412.2.

INTERMEDIATE 23

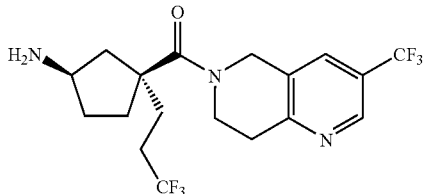

This intermediate was prepared in an analogous fashion to Intermediate 19, except Intermediate 11 was replaced with Intermediate 13. LC-MS for $C_{18}H_{21}F_6N_3O$ calculated 409.17, found $[M+H]^+$ 410.2.

INTERMEDIATE 26

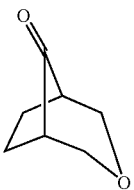

Step A:

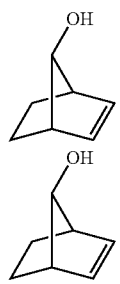

To a stirred solution of phenyl magnesium bromide (3 M solution in ether, 680 mL, 2 mol) in ethyl ether (500 mL) was added exo-epoxynorbornane (150 g, 1.36 mol) in ethyl ether (250 mL) slowly. After the initial exotherm, the reaction was heated to reflux for 3 h, after which time it was cooled in an ice bath and quenched with water (25 mL). The resulting solution was diluted with ethyl ether and washed with aqueous 3 N HCl twice. The combined aqueous layers where back extracted with ethyl ether twice and the combined organic layers where washed with brine, dried over MgSO$_4$, filtered, and concentrate under reduced pressure (100 mmHg, 30° C.) to give 230 g of a crude orange oil. This material was subject to flash chromatography (silica gel, 40% ethyl ether/hexanes) to give 67 g of pure product (45%). $^1$H NMR (500 MHz, CDCl$_3$): □ 6.06 (d, J=1.0 Hz, 2H), 3.76 (s, 1H), 2.75 (d, J=2.0 Hz, 2H), 1.86 (br s, 2H), 1.71–1.68 (m, 2H).

Step B

To a cooled (−78° C.) solution of oxalyl chloride (83 g, 660 mmol) in dichloromethane (500 mL) was added DMSO (78 mL, 1.1 mol) in dichloromethane (200 mL) rapidly but keeping the temperature below −50° C. To this solution was immediately added the product from Step A (67 g, 610 mmol) in dichloromethane (600 mL) rapidly, but keeping the temperature below −50° C. After stirring for 15 min at −78° C. this solution was treated with triethylamine (310 mL, 2.1 mol) and allowed to warm to room temperature. After 1 h at room temperature, the reaction was quenched with water and concentrated under reduced pressure. The crude residue was dissolved in a 3:1 solution of ethyl ether and petroleum ether and washed 3 times with aqueous 1 N HCl then with brine. The organic layer was dried over Na$_2$SO$_4$, filtered, and concentrated under reduced pressure. The resulting residue was quickly chromatographed (short column—silica gel, 15% ethyl ether/hexanes) and concentrated under reduced pressure. Final purification was achieved by distillation (collecting the 60° C. to 70° C. fractions at 30 mm Hg) to give 18.5 g of pure product as a colorless liquid (28%). $^1$H NMR (500 MHz, CDCl$_3$): □ 6.53 (br s, 2H), 2.82 (br s, 2H), 1.97 (d, J=7.0 Hz, 2H), 1.21 (dd, J=4.5, 6.5 Hz, 2H).

Step C

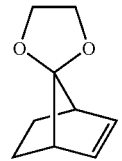

The product from Step B (17.5 g, 162 mmol) was combined with p-toluenesulfonic acid (4.9 g, 26 mmol) and ethylene glycol (13.1 mL, 243 mmol) in benzene (200 mL) and heated to reflux. After 5 h, the solution was allowed to cool to room temperature and stir overnight, after which time it was partitioned between ethyl ether and aqueous saturated NaHCO$_3$. The organic phase was washed with brine, dried over MgSO$_4$, filtered and concentrated. The product was purified by flash chromatography (silica gel, 10% ethyl ether/hexanes) to give 19.0 g of a colorless oil (83%). $^1$H NMR (500 MHz, CDCl$_3$): □ 6.18 (br s, 2H), 3.92 (t, J=6.0 Hz, 2H), 3.85 (t, J=6.0 Hz, 2H), 2.53 (br s, 2H), 1.92 (d, J 7.5 Hz, 2H), 0.97 (dd, J 3.5, 10.5 Hz, 2H).

Step D

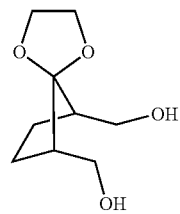

A solution of the product from Step C (2.0 g, 13 mmol) in a mixture of methanol (30 mL) and dichloromethane (24 mL) was cooled to −78° C. and treated with ozone gas (7.5 psi, 2 L/min) until a blue tint to the solution was apparent. At this time, the reaction was purged with nitrogen gas to remove the excess ozone and sodium borohydride (600 mg, 16 mmol) was added to the reaction. The reaction was allowed to warm to 0° C. on an ice bath before acetone was added to quench the excess reducing agent. The resulting solution was concentrated under reduced pressure and the product was purified by flash chromatography (silica gel, eluting with ethyl acetate) to give 1.9 g of a colorless oil which upon cooling to −20° C. became a colorless solid (78%). $^1$H NMR (500 MHz, CDCl$_3$): d 4.02 (m, 4H), 3.67 (m, 4H), 2.22 (t, J=6.0 Hz, 2H), 1.83 (m, 2H), 1.63 (m, 2H).

Step E

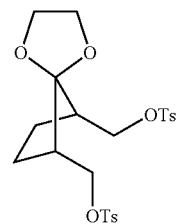

To a cooled (−15° C.) solution of the product from Step D (1.26 g, 6.71 mmol) in tetrahydrofuran (21 mL) was added n-butyllithium (2.5 M in hexanes, 2.8 mL, 7.0 mmol). After the reaction was stirred for 30 min at −15° C., tosyl chloride (1.28 g, 6.71 mmol) in tetrahydrofuran (10 mL) was added dropwise and the reaction was warmed to room temperature and stirred for an additional 30 min before being concentrated under reduced pressure. The mono-tosylate product was separated from small amounts of starting material and di-tosylation product by medium pressure liquid chromatography (silica gel, 40–100% ethyl acetate/hexanes) to give 900 mg of a colorless oil (39%) which was used directly in the next step.

Step F

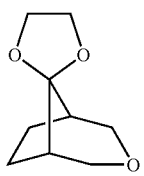

The product from Step E (707 mg, 2.07 mmol) was combined with sodium hydride (60% dispersion in mineral oil, 250 mg) in tetrahydrofuran and stirred at room temperature. After 2 h the reaction was quenched with hydrogen chloride (2 N solution in ethyl ether, 4 mL) and the resulting precipitate was filtered off. The filtrate was concentrated and purified by flash chromatography (silica gel, 20% ethyl ether/hexanes) to give 320 mg of product (91%). $^1$H NMR (500 MHz, CDCl$_3$): d 3.97 (m, 4H), 3.93 (d, J=10.5 Hz, 2H), 3.57 (dd, J=2.5, 11.0 Hz, 2H), 1.84–1.81 (m, 2H), 1.75 (m, 4H).

Step G

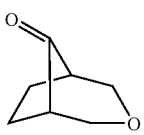

The product from Step F (250 mg, 1.47 mmol) was dissolved in a mixture of tetrahydrofuran (4 mL) and aqueous 5% HCl (2 mL) and stirred at room temperature. After 18 h the reaction was diluted with ethyl ether, washed with brine, and dried over MgSO$_4$, filtered and concentrated under reduced pressure. The product was purified by flash chromatography (silica gel, 30% ethyl ether/hexanes) to give 51 mg of a volatile liquid (28%). $^1$H NMR (500 MHz, CDCl$_3$): d 3.99 (dd, J=2.5, 11.0 Hz, 2H), 3.87 (d, J=11 Hz, 2H), 2.28 (br s, 2H), 2.03 (m, 2H), 1.99 (m, 2H).

INTERMEDIATE 27

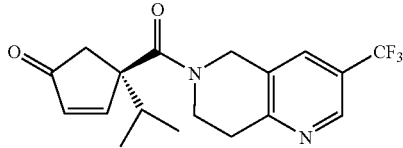

Step A:

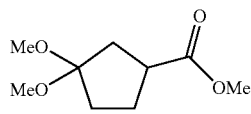

A solution of methyl-3-oxocyclopentane-carboxylate (20 g, 160 mmol) and trimethyl orthoformate (85 mL, 780 mmol) in methanol was treated with a catalytic amount of p-toluenesulfonic acid (3 g, 15.6 mmol) and the resulting solution was stirred for 4 h at room temperature. The solvent was evaporated under reduced pressure and the residue was then dissolved in ether (600 mL). The solution was washed with saturated sodium bicarbonate (2×200 mL), water (150 mL), brine (200 mL), dried over anhydrous sodium sulfate, filtered, and the solvent evaporated as before. Purification by flash column (eluant: 25% ether/pentane) afforded 21.52 g (73%) of the desired product as a clear oil. $^1$H NMR (500 MHz, CDCl$_3$) δ 3.68 (s, 3H), 3.21 (d, J=9.9 Hz, 6H), 2.89 (p, J=8.5 Hz, 1H), 2.14–2.05 (m, 2H), 2.02–1.80 (m, 4H).

Step B:

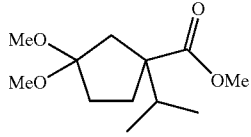

A flame dried 500 mL round bottom flask was charged with 150 mL of dry tetrahydrofuran, and then, set under nitrogen and cooled to −78° C. using an acetone/dry ice bath. Diisopropylamine (19.2 mL, 137 mmol) was added to the cooled solvent via syringe. 2.5 M n-butyllithium in hexanes (55 mL, 140 mmol) was slowly added to the solution. After 5 min stirring, the methyl ketal described in Step A, Intermediate 3 (21.52 g, 114.4 mmol) in 50 mL of tetrahydrofuran was added dropwise via syringe and the resulting mixture was stirred at −78° C. for 2 h. 2-iodopropane (34.3 mL, 343 mmol) was then added dropwise via syringe and the resulting mixture was stirred overnight allowing it to warm slowly to room temperature. The reaction was quenched with a solution of 10% citric acid and the organics were separated. The aqueous layer was extracted with ether (3×150 mL) and all the organics were combined, dried over anhydrous sodium sulfate, filtered, and evaporated under reduced pressure. The crude product was purified by flash column using an eluant of 20% ether/pentane to afford 16.74 g (64%) of the desired product. $^1$H NMR (400 MHz, CDCl$_3$) d 3.69 (s, 3H), 3.18 (d, J=20.5 Hz, 6H), 2.57 (d, J=13.9 Hz, 1H), 2.29–2.20 (m, 1H), 1.90 (p, J 6.8 Hz, 1H), 1.88–1.80 (m, 2H), 1.69–1.61 (m, 2H), 0.89 (dd, J=11.9 Hz, 6.8 Hz, 6H).

Step C:

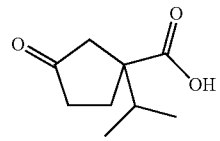

A solution of the ester from Step B, Intermediate 3 (16.74 g, 72.7 mmol) in ethanol (30 mL) was treated with 5 M aqueous NaOH (55 mL) and the resulting mixture was heated to reflux for 3 days. The mixture was then cooled to room temperature and acidified with concentrated hydrochloric acid. The organic solvent was evaporated under reduced pressure and the aqueous layer was then extracted with dichloromethane (5×100 mL). The organic extracts were combined, dried over anhydrous magnesium sulfate, filtered, and evaporated in vacuo to yield the crude 3-oxocyclopentane carboxylic acid (11.07 g, 90%) as a yellow oil. Purification was not attempted because of the compounds polarity and lack of a chromophore. ¹H NMR (500 MHz, CDCl₃) d 2.70 (d, J=18.1 Hz, 1H), 2.44–2.39 (m, 1H), 2.30–2.15 (m, 2H), 2.14 (dd, J=18.1, 1.0 Hz, 11H), 2.06 (p, J=6.9 Hz, 1H), 1.98 (m, 1H), 0.98 (dd, J=11.4, 6.9 Hz, 6H).

Step D

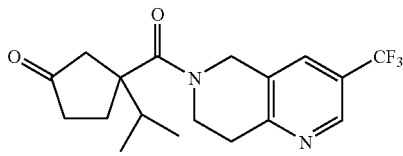

To a solution of the acid from Step C (540 mg, 3.20 mmol) in dichloromethane (50 mL) was added oxalyl chloride (0.834 mL, 9.60 mmol) followed by 2 drops of N,N-dimethylformamide. The solution was stirred at room temperature for 80 min and then evaporated under reduced pressure. The residue was dissolved in dichloromethane (2 mL) and added via syringe to a prepared solution of Intermediate 2 (880 mg, 3.20 mmol) and triethylamine (0.820 mL, 6.50 mmol) in dichloromethane (20 mL). The resulting mixture was stirred at room temperature for 18 h and then quenched with water (25 mL). The organics were separated, washed with saturated sodium bicarbonate and brine, dried over anhydrous sodium sulfate, filtered, and evaporated. The crude product was purified by MPLC using a step-wise gradient eluant of 0–70% ethyl acetate:hexanes to afford Intermediate 2 (720 mg, 64%). ¹H NMR (500 MHz, CDCl₃).

Step E:

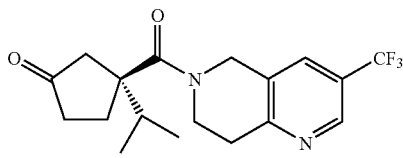

Resolution of product from Step D, Intermediate 27 was accomplished by chiral separation using an HPLC equipped with a preparative ChiralPak AD column. The separation was accomplished by injecting 100 mg/run and using an eluant of 25% isopropanol and 75% heptane with a flow rate of 9 mL/min.

INTERMEDIATE 28

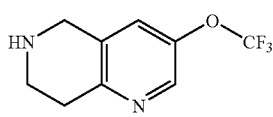

Step A:

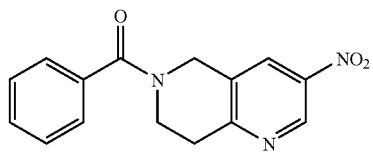

-continued

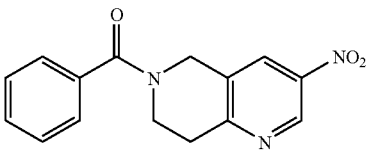

To a solution of the pyridone from Step A, Intermediate 10 (7.50 g, 37.6 mmol) in 200 mL of 2 M methanol/ammonia was added 1-benzoyl-4-piperdone (8.42 g, 41.4 mmol) and the mixture was heated at 60° C. for 18 h. The solvent was evaporated and the crude mixture was subject to chromatography, eluting with hexanes/ethyl acetate (50–70%). 10.2 g (96%) of the title product was collected. LC-MS for C₁₅H₁₃N₃O₃ calculated 283.10 found 284.15 [M+H]⁺.

Step B:

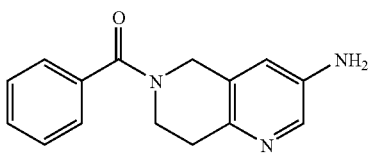

A mixture of the product from Step A (10.2 g, 36.0 mmol) and Pd/C (1.1 g) in methanol (400 mL) was stirred overnight under a hydrogen atmosphere and then filtered through celite. Purification by column chromatography eluting with hexanes/ethyl acetate (1:1) and methanol (5%) afforded 6.53 g (72%) of the title product. ¹H NMR (CD₃OD, 500 MHz) d7.98 (s, 1H), 7.46 (b, 6H), 6.83 (b, 2H), 4.84–4.44 (b, 2H), 3.72–3.67 (b, 2H), 3.09–2.94 (b, 2H). LC-MS for C₁₅H₁₅N₃O calculated 253.12 found 254.15 [M+H]⁺.

Step C:

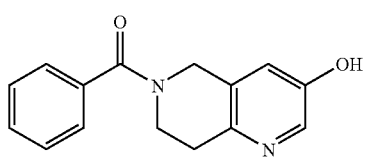

A mixture of the amine from step B (6.50 g, 25.6 mmol) and 30 mL of 20% sulfuric acid at 0° C. was treated with a solution of sodium nitrite (1.86 g, 28.2 mmol) in water (15 mL) via a syringe. After stirring vigorously at 0° C. for 25 min a small crystal of urea was added. The resulting deep red mixture was added slowly, via a cannula, to 150 mL of 20% sulfuric acid at 90° C. The flask was removed from the oil bath immediately upon completion of addition (10 min) and the mixture was cooled to room temperature. The pH was adjusted to 7 with potassium carbonate and the resulting precipitate was filtered off. The filtrate was the extracted with dichloromethane and the combined organic layers were washed with brine, dried (MgSO₄) and concentrated in vacuo. Purification by column chromatography eluting with hexanes/ethyl acetate (1:1) and 4% methanol afforded 4.68 g (72%) of the title product. LC-MS for C₁₅H₁₄N₂O₂ calculated 254.11 found 255.1 [M+H]⁺. The aqueous layer contained the deprotected amine.

Step D

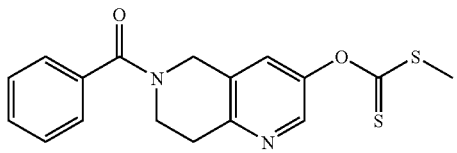

A flame dried, 3-neck round bottom flask containing a suspension of 0.71 g (18 mmol) sodium hydride (60% dispersion in mineral oil) and anhydrous N,N-dimethylformamide (30 mL) under $N_2$ was stirred for 10 min. The product from Step C (3.0 g, 12 mmol) in N,N-dimethylformamide (30 mL) was then added slowly via a cannula and the resulting creamish brown mixture was stirred at room temperature for 45 min then at 50° C. for 30 min. After cooling to room temperature carbon disulfide (3.5 mL, 59 mmol) was added slowly and the resulting dark brown mixture was stirred at room temperature for 2 h. Iodomethane (3.07 mL, 47.2 mmol) was then added slowly via a syringe and after stirring for 30 min, the reaction was quenched with water. The suspension was diluted with ethyl acetate, extracted and the combined organic layers were dried ($MgSO_4$) and concentrated in vacuo. The resulting brown oil was chromatographed eluting with hexanes/ethyl acetate (40–60%) to afford 3.52 g (87%) of the title product. LC-MS for $C_{17}H_{16}N_2O_2S_2$ calculated 344.07 found 345.1 $[M+H]^+$.

Step E:

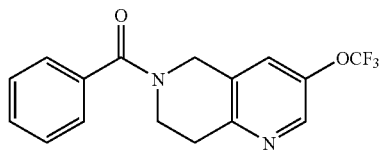

A flame dried, 3-neck 500 mL round bottom flask containing a suspension of 13.8 g (45.9 mmol) 1,3-dibromo-5,5-dimethylhydantoin in dichloromethane (200 mL) was stirred at room temperature for 10 min and then cold to –78° C. 100 g (80 eq) of hydrogen fluoridelpyridine (70%) solution was then added slowly via a syringe and the resulting clear solution was stirred at –78° C. for 30 min. 3.5 g, (10.2 mmol) of the product from Step C in dichloromethane (60 mL) was then added via a cannula and the resulting creamish/yellow mixture was stirred at –5° C. for 2 h. The mixture was diluted with ether at –5° C. and quenched with a cold solution of sodium bicarbonate and sodium bisulfate until the red color disappeared. The pH was adjusted to 7–8 with 5.0 N NaOH and the layers were separated. The organic layer was dried ($MgSO_4$) and concentrated in vacuo. Flash chromatography, eluting with hexanes/ethyl acetate (40–50%) afforded 2.47 g (75%) of the title product. LC-MS for $C_{16}H_{13}F_3N_2O_2$ calculated 322.09 found 323.2 $[M+H]^+$.

Step F

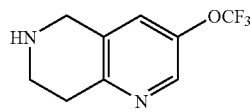

A solution of the product from Step E (2.45 g, 7.60 mmol) in 20 mL concentrated HCl was stirred at 75° C. for 18 h and concentrated. The resulting oil was dissolved in dichloromethane (200 mL) and stirred with $Ca(OH)_2$ (2.0 g) for 30 min. The white precipitate was filtered through celite, and the filtrate was concentrate to afford 1.52 g (92%) of the product, Intermediate 28. $^1H$ NMR ($CD_3OD$, 500 MHz) d8.34 (s, 1H), 7.22 (s, 1H), 4.04 (s, 2H), 3.25–3.22 (t, 2H), 2.97–2.95 (t, 2H). LC-MS for $C_9H_9F_3N_2O$ calculated 218.07 found 219.05 $[M+H]^+$.

INTERMEDIATE 29

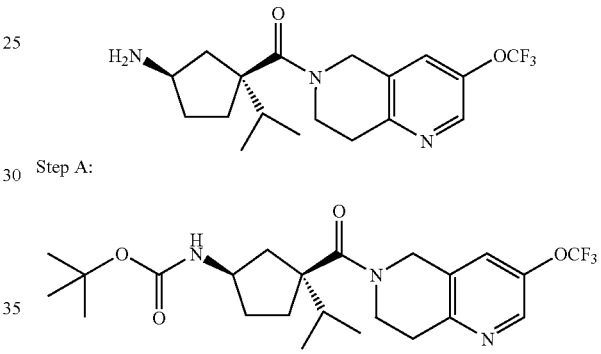

Step A:

The procedure described in Step A, Intermediate 19 were followed but using intermediate 28 instead of intermediate 8. LC-MS for $C_{23}H_{32}F_3N_3O_4$ calculated 471.23 found 372.25 $[M+H-Boc]^+$.

Step B:

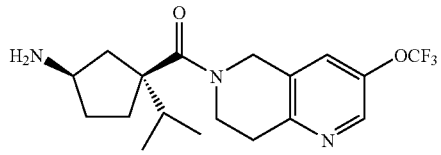

A solution of the product from Step A in ethyl acetate at 0° C. was treated with a saturated solution of HCl in ethyl acetate and the mixture was stirred for 2 h. The volatiles were evaporated in vacuo to afford a white foam, Intermediate 29 LC-MS for $C_{18}H_{24}F_3N_3O_2$ calculated 371.18 found 372.25 $[M+H]^+$.

INTERMEDIATE 30

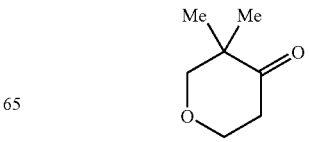

Step A:

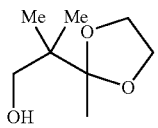

A mixture of ethyl 2,2-dimethyl-methylacetoacetate (3.0 g, 21 mmol), ethylene glycol (3.8 g, 62 mmol), camphorsulfonic acid (50 mg) and benzene (50 mL) was refluxed in a Dean-Stark apparatus, with continues removal of water. After ensuring the completion of the reaction (by TLC) it was diluted with water and extracted with ether (100 mL). The ether layer was washed with brine, dried (anhydrous magnesium sulfate) and concentrated to afford the desired compound (4.1 g). This was taken in ether (50 mL) and was slowly added to lithium aluminum hydride (1.2 g, 32 mmol) at 0° C. The reaction was warmed to room temperature and stirred for 12 h. The reaction mixture was then quenched sequentially with water (1.5 mL), 15% NaOH (1.5 mL) and water (4.5 mL). The resultant heterogeneous mixture was vigorously stirred and filtered. Evaporation of the filtrate followed by flash column chromatography eluting with hexanes/ethyl acetate (4:1) gave 2.2 g of the title compound.

Step B

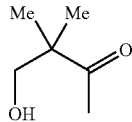

To a stirring slurry of silica (12 g, 230–400 mesh) in methylene chloride (100 mL) was added a 10% aqueous solution of oxalic acid followed by the product from step A (2.0 g, 13 mmol) in methylene chloride (5 mL). The resultant mixture was stirred at room temperature until the reaction was complete. Upon the completion of the reaction, NaHCO$_3$ (1.0 g) was added. The reaction was stirred for 10 min and then filtered. The filtrate was evaporated to give the 1.5 g of the title compound that required no purification.

Step C

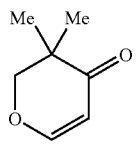

To a premixed solution of triethyl orthoformate (1.3 g, 8.6 mmol), tin (IV) chloride (8.6 mL 1.0 M solution in dichloromethane, 8.6 mmol) at −40° C. was added the ketone from Step B (0.5 g, 4.3 mmol) in dichloromethane (3 mL). The reaction mixture was warmed to −5° C. over 1.5 h before being quenched with saturated NaHCO$_3$ solution and extracted with ether (2×50 mL). The ether layer was washed with brine, dried (anhydrous magnesium sulfate), concentrated and purified by flash column chromatography. Eluting with hexanes/ether (9:1) gave the title compound (0.23 g, 43%).

Step D

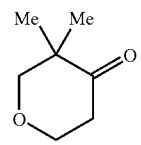

The intermediate from Step C (0.23 g) in hexanes (5 mL) and Pd/C (5%, 10 mg) was hydrogenated at room temperature using a hydrogen filled balloon until TLC indicated the completion of reaction. The reaction mixture was filtered and the filtrate was carefully evaporated (volatile product!) to yield the mixtures of the desired Intermediate 30 and the over reduction product. The recovery of Intermediate 30 was further facilitated by a subsequent TPAP/NMMO/dichloromethane oxidation of the mixture, which after 1 h was filtered to yield 221 mg of the title compound that required no further purification. $^1$H NMR (CDCl$_3$, 500 MHz): d 3.98 (t, 2H), 3.58 (s, 2H), 2.56 (t, 2H), 1.15 (s, 6H).

INTERMEDIATE 31

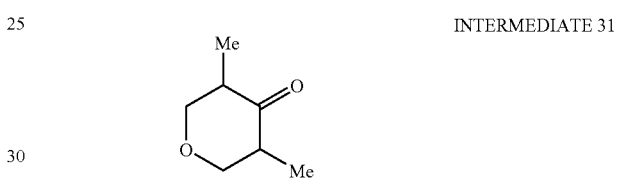

Following Steps A–D given for the preparation of intermediate 30 and starting from methyl 2,4-dimethyl-3-oxobutyrate, gave the title compound. $^1$H NMR (CDCl$_3$, 500 MHz): d 4.22 (m, 1H), 3.99 (m, 1H), 3.62 (m, 1H), 3.28 (m, 1H), 2.72 (m, 1H), 1.16 (d, J=6.8 Hz, 3H), 0.97 (d, J=6.8 Hz, 3H).

INTERMEDIATE 32

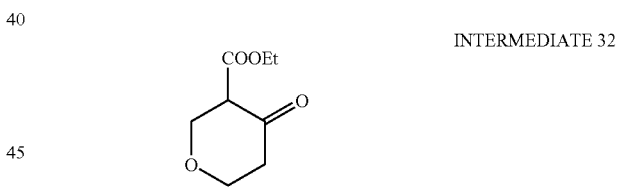

Prepared according to *J. Am. Chem. Soc.*, 1997, 119, 4285, except that the reaction was performed on the ethyl ester.

INTERMEDIATE 33

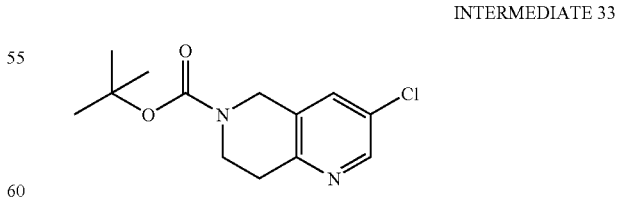

To a solution of t-butyl 4-oxo-1-piperidinecarboxylate (5.0 g, 25 mmol) in tetrahydrofuran (50 mL) at −10° C. was added a solution of lithium bis(trimethylsilyl)amide (25 mmol, 1 M solution in tetrahydrofuran) and the resultant solution was stirred for 1 h while the temperature was raised to 0° C. 2-chloro-1,3-bis(dimethylamino)trimethinium hexafluorophosphate (11.5 gm, 37.6 mmol) was added in one lot and the stirring was continued for an additional 20 min at 0° C. and then at room temperature for 2 h. Ammonium acetate (4.83 gm, 63.0 mmol) was added to the above and the resultant reddish brown mixture was stirred for 4 h at 60° C. The reaction mixture was cooled and extracted with ether (2×100 mL). The organic layer was dried (MgSO$_4$) and concentrated in vacuo. Flash chromatography eluting with hexanes/ethyl acetate (10–20%) afforded 3.97 g (60%) of the title product. $^1$H NMR (CDCl$_3$, 500 MHz): d 8.39 (s, 1H), 7.43 (s, 1H), 4.59 (s, 2H), 3.75 (t, J=5.7 Hz, 2H), 2.98 (t, J=5.7 Hz, 2H), 1.50 (s, 9H).

INTERMEDIATE 34

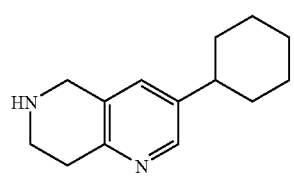

Step A:

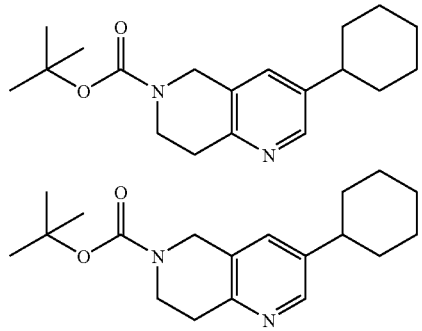

A 3-neck, flame dried, round bottom flask containing Intermediate 33 (500 mg, 1.86 mmol), Iron (III) acetylacetonate (0.032 g, 0.090 mmol) and 10 mL tetrahydrofuran/N-methyl-2-pyrrolidone (9:1) at 0° C. was treated with 2.21 mL (1.0 M) of cyclohexyl magnesium bromide. The orange/red color immediately disappear and the resulting dark brown mixture was stirred over the weekend. The reaction was quenched with saturated aqueous ammonium hydroxide and extracted with ether. Flash chromatography eluting with hexanes/ethyl acetate (15%) afforded 0.295 g of the title product. $^1$H NMR (CD$_3$OD, 500 MHz) d8.29 (s, 1H), 7.24 (s, 1H), 4.59 (s, 2H), 3.78–3.74 (t, 2H), 2.98 (t, 2H), 2.52 (b, 1H), 1.88–1.86 (b, 2H), 1.79–1.77 (b, 1H), 1.51–1.49 (b, 13H), 1.45–1.40 (t, 2H), 1.3–1.28 (b, 1H). LC-MS for C$_{19}$H$_{28}$N$_2$O$_2$ calculated 316.22 found 317.15 [M+H]$^+$.

Step B

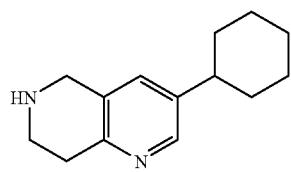

A solution of the product from Step A in ethyl acetate at 0° C. was treated with a saturated solution of HCl in ethyl acetate and the resulting mixture was stirred for 2 h. The volatiles were evaporated in vacuo to afford a white foam, Intermediate 34. LC-MS for C$_{14}$H$_{20}$N$_3$ calculated 216.32 found 217.32 [M+H]$^+$.

INTERMEDIATE 35

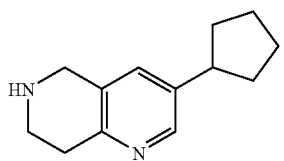

Step A:

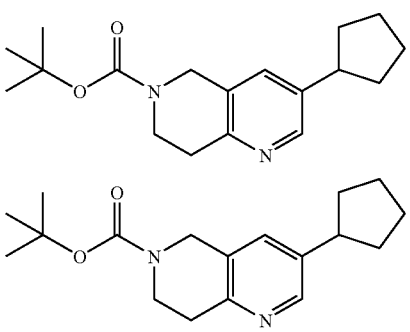

Starting from Intermediate 33 (0.8 g, 3 mmol) and cyclopentylmagnesium bromide (1.5 mL, 2 M solution in ether) using a procedure analogous to intermediate 34, Step A yielded 0.245 g of the title compound. $^1$H NMR (CD$_3$OD, 500 MHz) d8.32 (s, 1H), 7.27 (s, 1H), 4.58 (s, 2H), 3.75 (t, 2H), 2.98 (t, 2H), 2.51–1.58 (m, 11H), 1.51 (s, 9H).

Step B

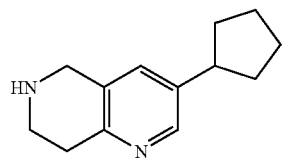

A solution of the product from Step A in ethyl acetate at 0° C. was treated with a saturated solution of HCl in ethyl acetate and the resulting mixture was stirred for 2 h. The volatiles were evaporated in vacuo to afford 0.230 g of Intermediate 35. LC-MS for C$_{13}$H$_{18}$N$_3$ calculated 202.15, found 203.4 [M+H]$^+$.

INTERMEDIATE 36

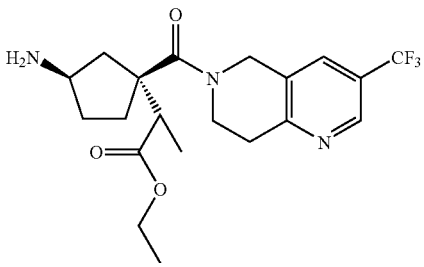

This intermediate was synthesized in a series of steps analogous to those described for Intermediate 16, except that in Step A acetaldehyde was replaced with ethyl 2-bromopropionate.

EXAMPLE 1

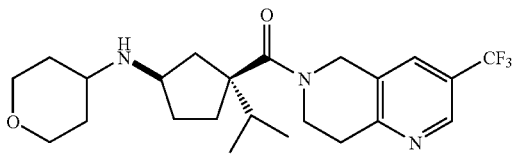

A solution of intermediate 19 (890 mg, 2.08 mmol), tetrahydro-4H-pyran-4-one (320 mg, 3.13 mmol), diisopropylethylamine (1.10 mL, 6.24 mmol) and crushed molecular sieves (4 Å, 500 mg) in dichloromethane (50 mL) was treated with sodium triacetoxyborohydride (2.20 g, 10.4 mmol) and stirred at room temperature overnight. The reaction was quenched with saturated sodium bicarbonate solution (50 mL) and diluted with an additional 25 mL of dichloromethane. The organic layer was separated and the aqueous layer was washed with dichloromethane (2×25 mL). The organics were combined, dried over anhydrous sodium sulfate, filtered and evaporated under reduced pressure. The crude product was purified by reverse phase HPLC to yield Example 1 (915 mg, 86.0%). LC-MS for $C_{23}H_{31}F_3N_3O_2$ calculated 439.24, found $[M+H]^+$ 440.2.

EXAMPLE 2

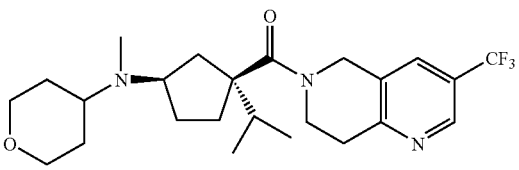

To a solution of product described in Example 1 (136 mg 0.265 mmol) and crushed 4 Å molecular sieves (100 mg) in dichloromethane (20 mL) was added formalin (0.2 mL) and the resulting suspension was stirred for 30 min at room temperature. This mixture was then treated with sodium triacetoxyborohydride (280 mg, 1.33 mmol) and stirred an addition 15 h at room temperature. The reaction was quenched with saturated sodium bicarbonate solution (20 mL) and diluted with an additional 10 mL of dichloromethane. The organic layer was separated and the aqueous layer was extracted with dichloromethane (2×20 mL). The organics were combined, dried over anhydrous sodium sulfate, filtered and evaporated under reduced pressure. The crude product was purified by reverse phase HPLC to yield Example 5 (80 mg, 57.6%). LC-MS for $C_{24}H_{35}F_3N_3O_2$ calculated 453.26, found $[M+H]^+$ 454.3.

EXAMPLE 3

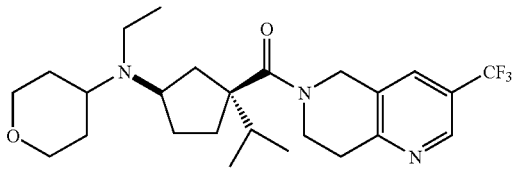

Example 3 was prepared as detailed in Example 2 using acetaldehyde instead of formaldehyde. LC-MS for $C_{25}H_{37}F_3N_3O_2$ $[M^+H^+]$ calculated 468.28, found 468.25.

EXAMPLE 4

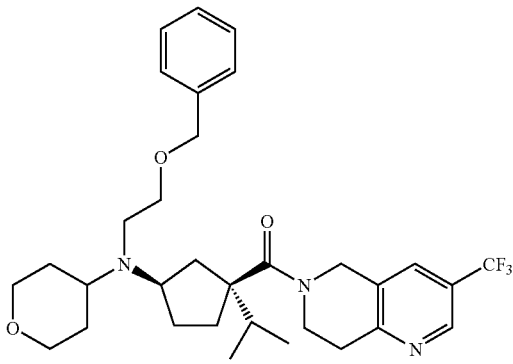

Example 4 was prepared as detailed in Example 2 using benzyloxyacetaldehyde instead of formaldehyde. LC-MS for $C_{32}H_{43}F_3N_3O_2$ $[M^+H^+]$ calculated 574.32, found 574.35.

EXAMPLE 5

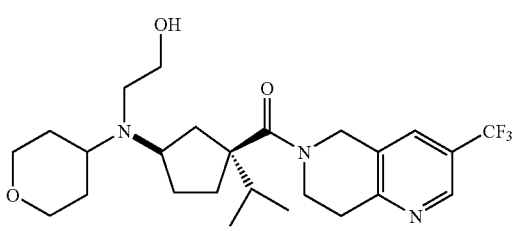

A mixture of Example 4 (43 mg, 0.075 mmol), 10% Pd/C (10 mg), and ethanol (5 mL) was stirred at room temperature under a hydrogen balloon for 18 h before being filtered and concentrated to dryness. The crude product was purified by reverse phase HPLC to yield Example 5 (13.3 mg, 36.9%). LC-MS for $C_{25}H_{37}F_3N_3O_3$ $[M^+H^+]$ calculated 484.27, found 484.3.

EXAMPLE 6

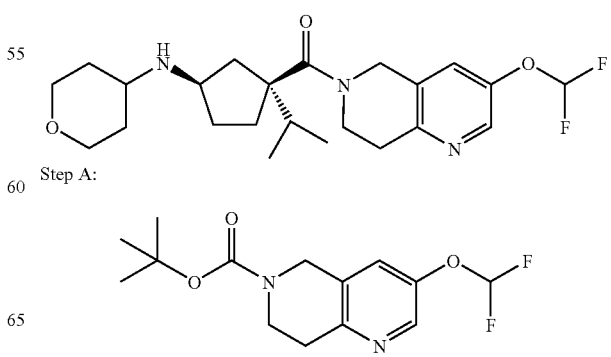

Step A:

-continued

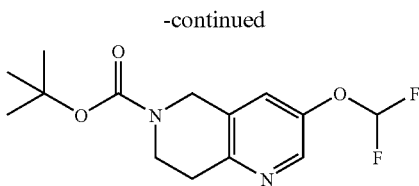

To Intermediate 10 (0.25 g, 1 mmol) and $K_2CO_3$ (0.5 g, 3.6 mmol) in dry N,N-dimethylformamide (5.0 mL) at 75° C. was bubbled $CHClF_2$ through the reaction vessel attached to a cold finger (at −78° C.) for 20 min. The mixture was stirred for an additional 2 h at 75° C., then allowed to cool to room temperature and stir overnight. The reaction mixture was diluted with water and extracted with ethyl acetate (2×25 mL). The solvent layer was washed with brine, dried ($MgSO_4$), and concentrated in vacuo. Purification was carried out by flash column chromatography (eluant: 95% hexanes/ethyl acetate) to afford 0.06 g (20%) of the title product. $^1H$ NMR (500 MHz, $CDCl_3$): 8.32 (d, J=2.1 Hz, 1H), 7.25 (d, J=2.1 Hz, 1H), 6.54 (t, J=72.7 Hz, 1H), 4.62 (s, 2H), 3.77 (t, J=6.0 Hz, 2H), 3.01 (t, J=5.7 Hz, 2H), 1.52 (s, 9H).

Step B

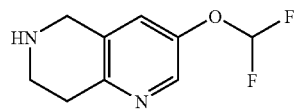

To a solution of the intermediate from Step A (0.06 g) in ethyl acetate (1.0 mL) was added a solution of HCl in ethyl acetate. The resulting solution was stirred for 30 min. Volatiles were removed under vacuum to give the desired product (0.054 g) as the HCl salt. LC-MS for $C_9H_{10}F_2N_2O$ calculated 200.19, found [M+H]$^+$ 201.05.

Step C

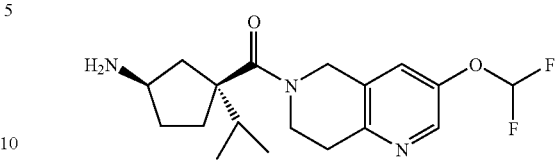

A mixture of Intermediate 11 (107 mg, 0.400 mmol), the intermediate from Step B, Example 6 (0.053 g, 0.27 mmol), 4-dimethylaminopyridine (2 mg) and bromo-tris-pyrrolidino-phosphonium hexafluorophosphate (0.247 g, 0.53 mmol) in dichloromethane (5.0 mL) was treated with diisopropylethylamine (0.27 mL, 1.6 mmol) and the resulting mixture was stirred overnight. The reaction was quenched with water and extracted with ethyl acetate. The organic layer was washed with brine, dried (anhydrous $MgSO_4$)) and concentrated in vacuo. Purification was carried out by preparative TLC (eluant: hexanes/ethyl acetate (1:1)) to afford 65.5 mg (55%) of the title product. LC-MS for $C_{23}H_{33}F_2N_3O_4$ calculated 453.25 found [M+H]$^+$ 454.2.

Step D

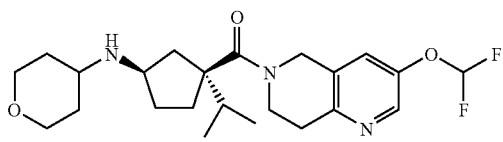

To a solution of the intermediate from Step D (0.065 g) in ethyl acetate (2.0 mL) was added a solution of HCl in ethyl acetate. The resulting solution was stirred for 30 min. Removal of the volatiles under reduced pressure gave the desired product (0.06 g) as the HCl salt. LC-MS for $C_{18}H_{25}F_2N_3O_2$ calculated 353.20, found [M+H]$^+$ 354.2.

Step E

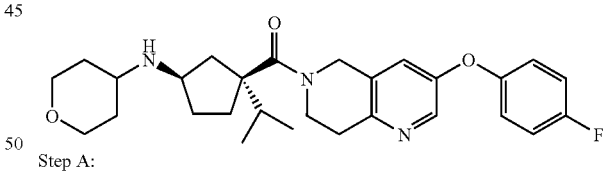

A solution of the intermediate from Step D (0.025 g, 0.070 mmol) in dichloromethane (2.5 mL) and diisopropylethylamine (0.042 mL) was treated with tetrahydro-4H-pyran 4-one (0.035 g, 0.35 mmol) and 4 Å molecular sieve. After stirring the mixture for 45 min, sodium triacetoxyborohydride (0.074 g, 0.35 mmol) was added. After 18 h the mixture was filtered and the filtrate was concentrated in vacuo. Reverse phase HPLC purification of the crude gave the title product, which was subsequently transformed to the HCl salt (0.018 g). LC-MS for $C_{23}H_{33}F_2N_3O_3$ calculated 437.26, found [M+H]$^+$ 438.25.

EXAMPLE 7

Step A:

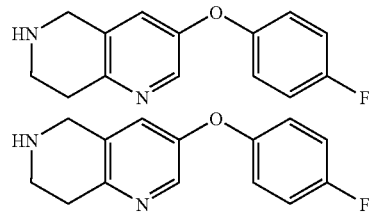

To a solution Intermediate 10 (0.098 g, 0.40 mmol) in dichloromethane (4.0 mL) was added p-fluorophenyl boronic acid (0.112 g, 0.800 mmol), copper (II) acetate (160 mg, 0.800 mmol), triethylamine (0.54 mL, 2.0 mmol) and 4 Å (500 mg) molecular sieves. The resultant mixture was stirred 48 h and filtered. The filtrate was concentrated and purified by preparative TLC (eluant: 1:1 hexanes/ethyl acetate) to afford 0.05 g of the N-Boc intermediate. This intermediate was subsequently transformed to the title compound by treating with 20% sulfuric acid to afford 0.094 g of the product. LC-MS for $C_{14}H_{13}FN_2O$ calculated 244.11, found $[M+H]^+$ 245.15.

Step B

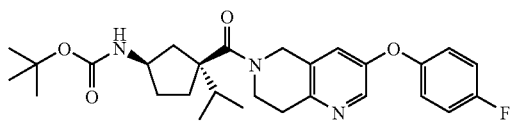

A mixture of Intermediate 11 (0.11 g, 0.41 mmol), the intermediate from Step A, Example 7 (0.09 g, 0.2 mmol), 4-dimethylaminopyridine (2 mg) and bromo-tris-pyrrolidino-phosphonium hexafluorophosphate (0.233 g, 0.5 mmol) in dichloromethane (5.0 mL) was treated with diisopropylethylamine (0.21 mL, 1.2 mmol) and the mixture was stirred overnight. The reaction was quenched with water and extracted with ethyl acetate. The organic layer was washed with brine, dried (anhydrous $MgSO_4$)) and evaporated in vacuo. Purification was carried out by preparative TLC (eluant: hexanes/ethyl acetate (1:1)) to afford 14.7 mg (32%) of the title product. LC-MS for $C_{28}H_{36}FN_3O_4$ calculated 497.28 found $[M+H]^+$ 498.4.

Step C

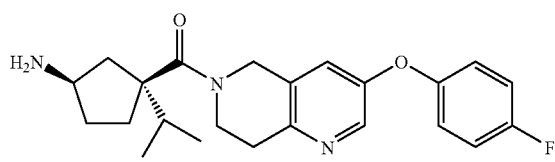

To a solution of the intermediate from Step B, Example 7 (0.014 g) in ethyl acetate (1.0 mL) was added a solution of HCl in ethyl acetate. The resulting solution was stirred for 30 min. Removal of the volatiles under reduced pressure gave the desired product (0.013 g) as the HCl salt. LC-MS for $C_{23}H_{28}FN_3O_2$ calculated 397.22, found $[M+H]^+$ 398.4.

Step D:

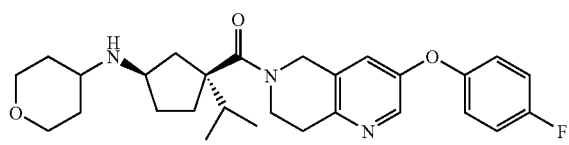

A solution of the intermediate from Step C, Example 7 (0.013 g, 0.070 mmol) in dichloromethane (2.0 mL) and diisopropylethylamine (0.042 mL) was treated with tetrahydro-4H-pyran 4-one (0.035 g, 0.35 mmol) and 4 Å molecular sieve. After stirring the mixture for 45 min, sodium triacetoxyborohydride (0.074 g, 0.35 mmol) was added. After 18 h, the mixture was filtered and the filtrate was evaporated in vacuo. Reverse phase HPLC purification of the crude afforded the title product, which was subsequently transformed to the HCl salt (0.007 g). LC-MS for $C_{28}H_{36}FN_3O_3$ calculated 481.28, found $[M+H]^+$ 482.2.

EXAMPLE 8

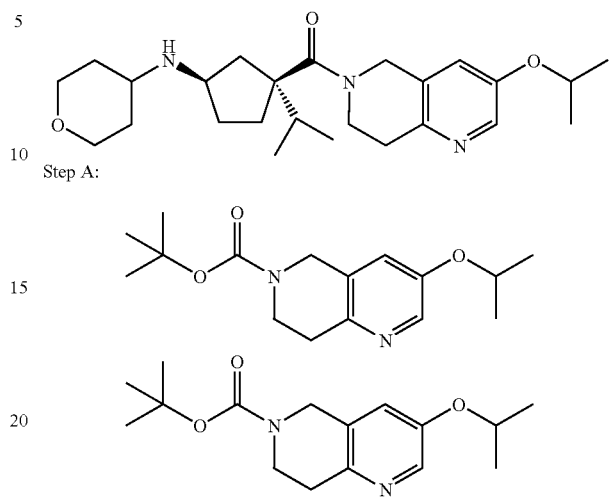

Step A:

To a solution of Intermediate 10 (100 mg, 0.40 mmol) in hexamethylphosphoramide (3.0 mL) at room temperature was added a solution of sodium hydroxide (32 mg, 0.80 mmol) in water (0.5 mL). After stirring for 5 min, 2-Iodopropane (0.079 mL, 0.80 mmol) was added to the mixture and the resultant reddish brown mixture was stirred overnight. The mixture was extracted with ethyl acetate and washed with water, brine, dried ($MgSO_4$) and concentrated in vacuo. Column chromatography eluting with hexanes/ethyl acetate (20–30%) afforded 0.075 g (70%) of the title product. $^1H$ NMR (500 MHz, $CDCl_3$):8.120 (s, 1H), 6.92 (s, 1H), 4.57 (s, 2H), 4.54 (m, J=2.4 Hz, 1H), 3.74 (t, 2H), 2.94 (t, 2H), 1.50 (s, 9H), 1.36 (d, J=2.4 Hz, 6H).

Step B

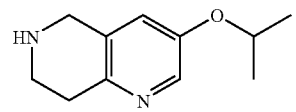

To the intermediate from Step A, Example 8 (75 mg, 0.28 mmol) was added a solution 4 N HCl in dioxane (2.0 mL) and the resulting mixture was stirred for 30 min. Evaporation of the volatiles in vacuo, afforded 0.070 g of the title compound. LC-MS for $C_{11}H_{16}N_2O$ calculated 192.13, found $[M+H]^+$ 193.1.

Step C

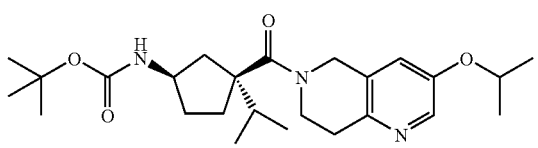

Starting from the intermediate prepared in Step B, Example 8 (0.070 g, 0.26 mmol) and Intermediate 11 (80 mg, 0.31 mmol) and following the procedure described in Step C, Example 3 gave 0.087 g of the title compound. LC-MS for $C_{25}H_{39}N_3O_4$ calculated 445.29, found $[M+H]^+$ 446.3.

Step D

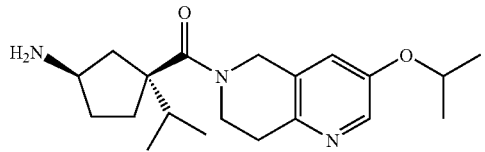

To a solution of the product described in Step C, Example 8 (0.087 g) in ethyl acetate (2.0 mL) was added a saturated solution of HCl in ethyl acetate (2.0 mL). the resulting solution was stirred for 30 min. Evaporation of the volatiles in vacuo, afforded 0.08 g of the amine HCl salt. LC-MS for $C_{20}H_{31}N_3O_2$ calculated 345.24, found $[M+H]^+$ 346.25

Step E

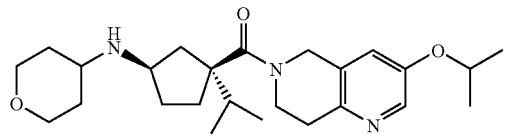

A solution of the product described in Step D, Example 8 (0.040 g, 0.095 mmol) in dichloromethane (2.0 mL) and diisopropylethylamine (0.042 mL) was treated with tetrahydro-4H-pyran 4-one (0.013 mL, 0.14 mmol) and 4 Å molecular sieve. After stirring the mixture for 45 min, excess sodium triacetoxyborohydride was added. Stirring was continued for another 18 h. The mixture was filtered and the filtrate was concentrated in vacuo. Reverse phase purification of the crude afforded 27.4 mg of the title product. LC-MS for $C_{25}H_{39}N_3O_3$ calculated 429.30, found $[M+H]^+$ 430.3.

EXAMPLE 9

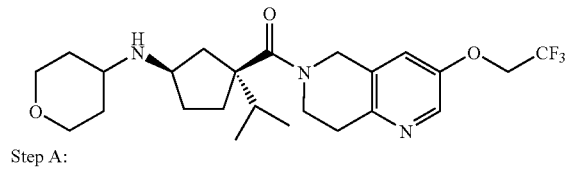

Step A:

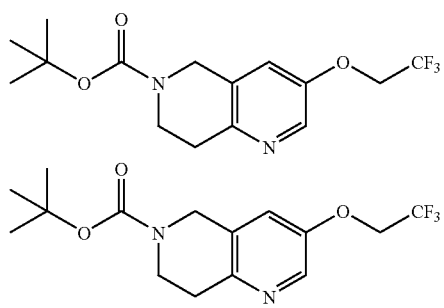

To a solution of Intermediate 10 (0.1 g, 0.399 mmol) in hexamethylphosphoramide (3.0 mL) at room temperature was added 0.048 g sodium hydride (60% dispersion in mineral oil) and the resulting brownish red mixture was stirred for 5 min. 2-Iodo-1,1,1-trifluoro ethane (0.12 mL) was then added to the mixture via a syringe and the mixture was stirred overnight. The reaction was quenched with water, extracted with ethyl acetate, dried (MgSO$_4$) and concentrated in vacuo. Column chromatography eluting with hexanes/ethyl acetate (20–30%) afforded 0.015 g (16%) of the title product $^1$H NMR (CDCl$_3$, 500 MHz) d8.20 (s, 1H), 7.02 (s, 1H), 4.59 (s, 2H), 4.39 (q, 2H), 3.75 (t, J=3.5 Hz, 2H), 1.50 (s, 9H).

Step B

To the intermediate from Step A, Example 9 (0.015 g) was added a saturated solution of HCl in ethyl acetate (2.0 mL). The resulting mixture was stirred for 30 min. Evaporation of the volatiles in vacuo, afforded 0.015 g of the title compound. LC-MS for $C_{10}H_{11}F_3N_2O$ calculated 232.08, found $[M+H]^+$ 233.2.

Step C

Starting from the intermediate prepared in Step B, Example 9 (0.015 g, 0.049 mmol) with Intermediate 11 (0.020 g, 0.073 mmol) and following the procedure described in Step C, Example 3 gave 0.013 g of the title compound. LC-MS for $C_{24}H_{34}F_3N_3O_4$ $[M+H]^+$ calculated 486.25, found 386.2 [M+H−100(Boc)].

Step D

To a solution of the product described in Step C, Example 9 (0.013 g) in ethyl acetate (2.0 mL) was added a 4 N solution of dioxane/HCl (2.0 mL). the resulting solution was stirred for 30 min. Evaporation of the volatiles in vacuo, afforded 0.015 g of the amine HCl salt. LC-MS for $C_{19}H_{26}F_3N_3O_2$ calculated 385.20, found $[M+H]^+$ 386.2.

Step E

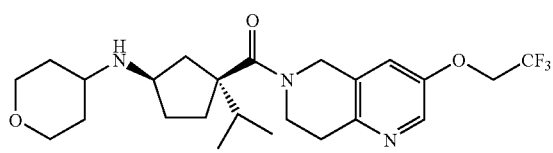

To a solution of the intermediate from Step D, Example 9 (0.015 g, 0.033 mmol) in dichloromethane (2.0 mL) and diisopropylethylamine (0.013 mL) was treated with tetrahydro-4H-pyran 4-one (0.006 mL) and 4 Å molecular sieve. The mixture was stirred for 45 min and sodium triacetoxyborohydride was added. After 18 h, the mixture was filtered and the filtrate concentrated in vacuo. Reverse phase purification afforded 4.2 mg of the title product. LC-MS for $C_{24}H_{34}F_3N_3O_3$ calculated 469.26, found $[M+H]^+$ 470.2.

EXAMPLE 10

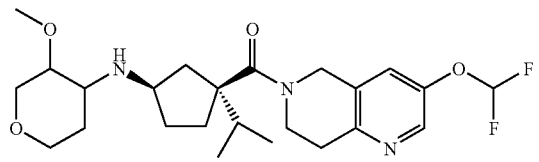

To a solution of the intermediate from Step D, Example 6 (0.035 g, 0.086 mmol) in dichloromethane (2.0 mL) and diisopropylethylamine (0.038 mL) was treated with 3-methoxy-pyran-4-one (0.056 g) and 4 Å molecular sieve. The mixture was stirred for 45 min and sodium triacetoxyborohydride was added. After 18 h, the mixture was filtered and the filtrate was concentrated in vacuo. Reverse phase purification (ChiralCel OD column) afforded 4.7 mg of the less polar and 7.2 mg of the more polar title products. LC-MS for (less polar isomer) $C_{24}H_{35}F_3N_3O_4$ calculated 467.26, found $[M+H]^+$ 468.25. LC-MS for (more polar isomer) $C_{24}H_{35}F_3N_3O_4$ calculated 467.26, found $[M+H]^+$ 468.25

EXAMPLE 11

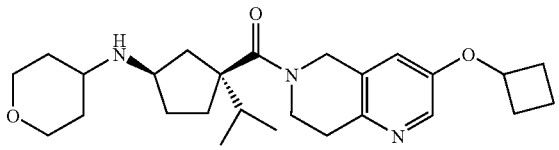

Step A:

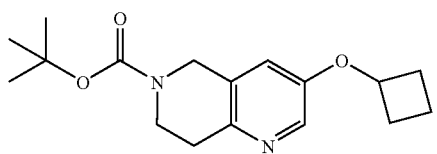

-continued

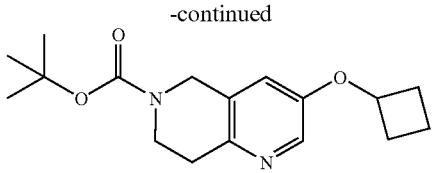

To a solution of Intermediate 10 (100 mg, 0.399 mmol) in hexamethylphosphoramide (3.0 mL) at room temperature was added 0.024 g sodium hydride (60% dispersion in mineral oil). The resulting brownish red mixture was stirred for 5 min. Bromocyclobutane (0.162 g) in hexamethylphosphoramide was then added to the mixture via a syringe and the mixture was stirred overnight. The reaction was quenched with water, extracted with ethyl acetate, dried (MgSO$_4$) and concentrated in vacuo. Column chromatography eluting with hexanes/ethyl acetate (20–30%) afforded 0.007 g (6%) of the title product. $^1$H NMR (400 MHz, CDCl$_3$) d8.06 (s, 1H), 6.86 (s, 1H), 4.64–4.67 (m, 1H), 4.57 (s, 2H), 3.72–3.75 (t, J=3.75 Hz, 2H), 2.94–2.96 (t, J=3.75 Hz, 2H), 2.44–2.50 (m, 2H), 2.15–2.21 (m, 2H), 1.88–1.91 (m, 1H), 1.70–1.76 (m, 1H), 1.51 (s, 9H).

Step B

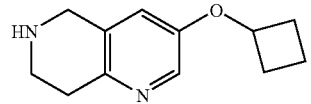

To a solution of the intermediate from Step A, Example 11 (0.007 g) was added a saturated solution of HCl in ethyl acetate (2.0 mL). The resulting solution was stirred for 30 min. Evaporation of the volatiles in vacuo, afforded 0.007 g of the title compound. LC-MS for $C_{12}H_{16}N_2O$ calculated 204.13, found $[M+H]^+$ 205.1.

Step C

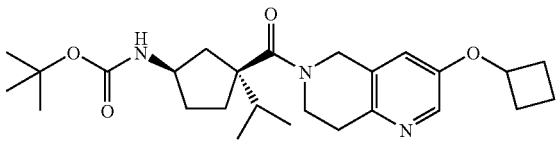

Starting from the product from Step B, Example 11 (0.007 g, 0.03 mmol) with Intermediate 11 (0.010 g, 0.035 mmol) and following the procedure described in Step C, Example 3 gave 0.005 g of the title compound. LC-MS for $C_{26}H_{39}N_3O_4$ calculated 457.25, found 358.2 [M+H−100 (Boc)].

Step D

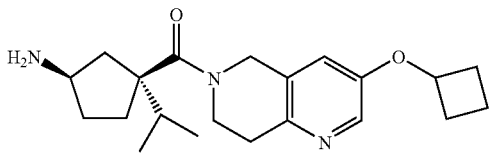

To a solution of product described in Step C, Example 11 (0.005 g) in ethyl acetate (2.0 mL) was added a 4 N solution of HCl in dioxane (2.0 mL). The resulting solution was stirred for 30 min. Evaporation of the volatiles in vacuo, afforded 0.004 g of the amine HCl salt. LC-MS for $C_{21}H_{31}N_3O_2$ calculated 357.20, found [M+H]$^+$ 358.2.

Step E:

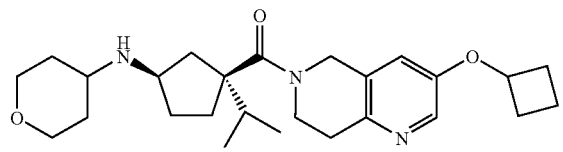

To a solution of the intermediate from Step D, Example 11 (0.004 g, 0.011 mmol) in dichloromethane (2.0 mL) and diisopropylethylamine (0.004 mL) was added tetrahydro-4H-pyran 4-one (0.003 mL) and 4 Å molecular sieve. The mixture was stirred for 45 min and sodium triacetoxyborohydride was added. After 18 h, the mixture was filtered and the filtrate was concentrated in vacuo. Reverse phase purification afforded 4.2 mg of the title product. LC-MS for $C_{26}H_{39}N_3O_3$ calculated 441.30, found [M+H]$^+$ 442.3.

EXAMPLE 12

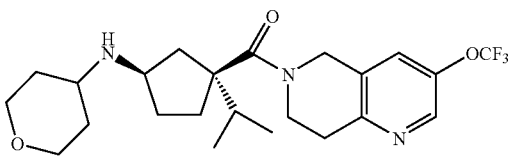

A solution of Intermediate 29 (50 mg 0.11 mmol) in dichloromethane (2.0 mL) and diisopropylethylamine (0.042 mL, 0.24 mmol) at room temperature under $N_2$ was treated with activated 4 Å molecular sieve (10 mg) and tetrahydro-4H-pyran-4-one (0.015 mL, 0.16 mmol). The mixture was stirred for 45 min and sodium triacetoxyborohydride (69 mg, 0.33 mmol) was added. After stirring for 16 h, the reaction was quenched with saturated aqueous sodium bicarbonate and filtered through celite. The layers were separated and the organic layer dried (MgSO$_4$), filtered and concentrated. Reverse phase HPLC purification afforded 20.1 mg of Example 12. LC-MS for $C_{23}H_{32}F_3N_3O_3$ calculated: 455.24 found: 456.25 [M+H]$^+$.

EXAMPLE 13

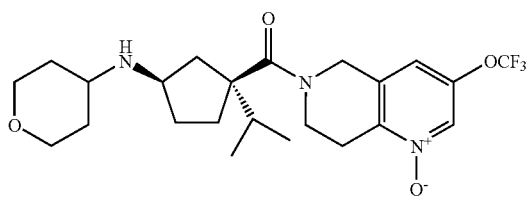

Step A:

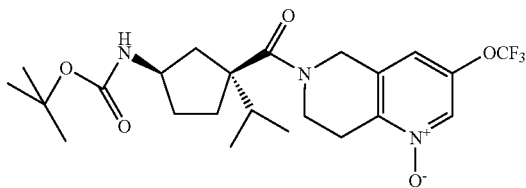

The product from Step A, Intermediate 29 (83 mg, 0.18 mmol), in dichloromethane (1.5 mL) was treated with 3-chloroperoxybenzoic acid (163 mg, 0.700 mmol). The mixture was stirred for 2 h and then excess Ca(OH)$_2$ was added and the reaction mixture was stirred for an additional for 30 min. The white precipitate was filtered through celite and the filtrate was concentrated in vacuo to afford the title product as a white foam. LC-MS for $C_{23}H_{32}F_3N_2O_5$ calculated: 487.23, found: 388.25 [M+H−Boc]$^+$.

Step B

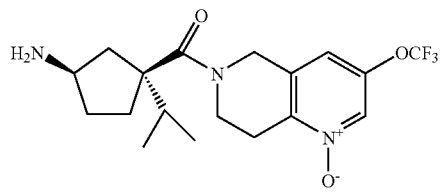

A solution of the product from Step A in ethyl acetate at 0° C. was treated with a saturated solution of HCl in ethyl acetate. The resulting solution was stirred for 2 h. The volatiles were evaporated in vacuo to afford the title product as a white foam which was used without further purification. LC-MS for $C_{18}H_{24}F_3N_3O_3$ calculated: 387.18, found 388.3 [M+H]$^+$.

Step C

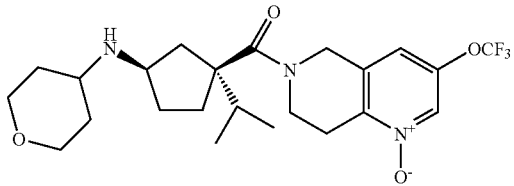

Following the procedure described for Example 12 but using the product from Step B instead of intermediate 29 afforded 33 mg of Example 13. LC-MS for $C_{23}H_{32}F_3N_3O_4$ calculated: 471.23, found: 472.3 [M+H]$^+$.

EXAMPLE 14

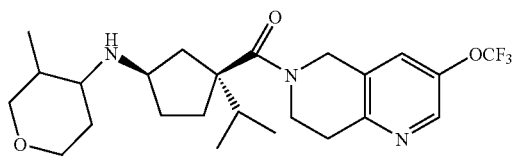

Following the procedure described for Example 12 but using Intermediate 1 instead of tetrahydro-4H-pyran-4-one afforded Example 14 as mixture of 4 diastereomers. Chiral separation on an OD column eluting with ethanol/heptane (5%) afforded the 4 resolved diastereomers. LC-MS for $C_{24}H_{34}F_3N_3O_3$ calculated: 470.26 found: 470.15 [M+H]$^+$.

EXAMPLE 15

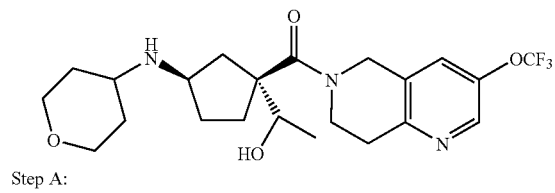

Step A:

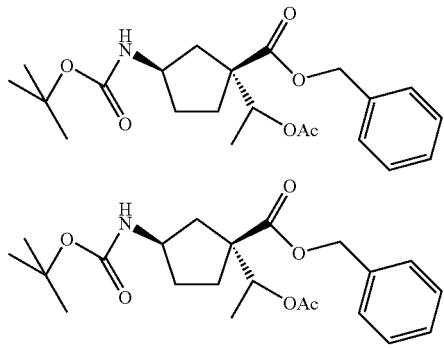

A solution of the ester from Step C intermediate 16 (diastereomeric mixture) (0.50 g, 1.3 mmol) in 5.0 mL of pyridine at 0° C. was treated with a catalytic amount of N,N-dimethyl-4-aminopyridine and 0.26 mL (2.75 mmol) of acetic anhydride. The resulting mixture was stirred overnight. The volatiles were evaporated and the product was purified by flash chromatography (eluting with hexanes/ethyl acetate 7:3). 0.527 g of the title product (mixture of 2 diastereomers) was collected. LC-MS for $C_{22}H_{31}NO_6$ calculated: 405.22, found: 406.2 [M+H]$^+$.

Step B

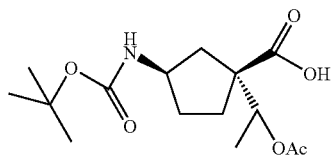

This acid was prepared following the procedure described in Step C Intermediate 12, and was used in the next step without further purification. LC-MS for $C_{15}H_{25}NO_6$ calculated 315.17 found 338.2 [M+Na].

Step C

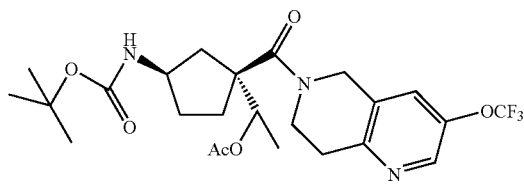

The procedure described in Step A, Intermediate 19 was followed, using Intermediate 28 instead of Intermediate 8 and the acid from Step B above. LC-MS for $C_{24}H_{32}F_3N_3O_6$ calculated: 515.22, found: 416.3 [M+H−Boc]$^+$.

Step D

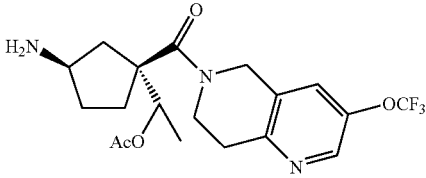

A solution of the product from Step C in ethyl acetate at 0° C. was treated with a saturated solution of HCl in ethyl acetate. The resulting solution was stirred for 2 h. The volatiles were evaporated in vacuo to afford a white foam and used with out further purification. LC-MS for $C_{19}H_{24}F_3N_3O_3$ calculated: 415.17, found: 416.4 [M+H]$^+$.

Step E

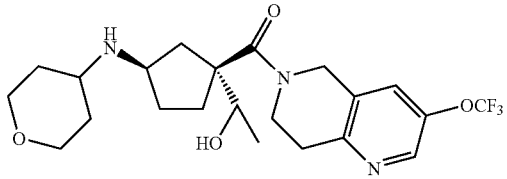

Following the procedure described for Example 12 but using the amine from Step D instead of intermediate 29 afforded the acetate protected product. Hydrolysis of the acetate was accomplished by stirring in a mixture of methanol/$K_2CO_3$(10 eq) at 70° C. Chiral separation on an OD column eluting with ethanol/hexanes (7%) afforded the desired resolved diastereomers (Example 15). LC-MS for $C_{22}H_{30}F_3N_3O_4$ calculated: 457.22, found: 458.15 [M+H]$^+$.

EXAMPLE 16

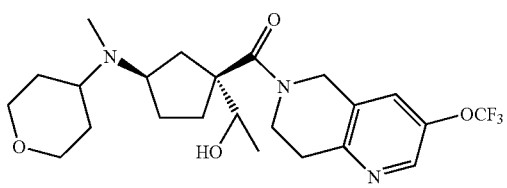

A solution of Example 15 (60 mg, 0.11 mmol) in methanol (2.0 mL) was treated with 0.169 mL of formaldehyde (37%, 1.13 mmol) and sodium cyanoborohydride (21 mg, 0.34 mmol). The mixture was stirred overnight and the volatiles were evaporated. The resulting oil was dissolved in dichloromethane and washed with a small amount of water. The aqueous layer was extracted with dichloromethane (×2) and the combined organic layers were dried (MgSO$_4$) and concentrated in vacuo. Purification by reverse phase HPLC afforded 36.3 mg of Example 16. LC-MS for $C_{23}H_{32}F_3N_3O_4$ calculated: 471.23 found: 472.25 [M+H]$^+$.

EXAMPLE 17

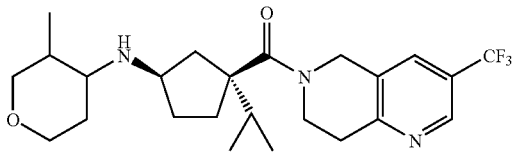

A solution of intermediate 19 (304 mg, 0.712 mmol), Intermediate 1 (160 mg, 1.42 mmol), diisopropylethylamine (370 μL, 2.14 mmol) and crushed molecular sieves (4 Å, 150 mg) in dichloromethane (25 mL) was treated with sodium triacetoxyborohydride (755 mg, 3.56 mmol) and stirred at room temperature overnight. The reaction was quenched with saturated sodium bicarbonate solution (25 mL) and diluted with an additional 25 mL of dichloromethane. The organic layer was separated and the aqueous layer was washed with dichloromethane (2×20 mL). The organics were combined, dried over anhydrous sodium sulfate, filtered and evaporated under reduced pressure. The residue was purified by preparative TLC (eluant: 0.5% NH$_4$OH/5% methanol/94.5% CH$_2$Cl$_2$) to yield 239 mg (74%) of the final product as a mixture of four diastereomers. Cis and trans racemate in reference to the pyran ring were resolved by HPLC equipped with a Preparative ChiralCel OD column (eluant: 5% ethanol/95% hexanes). Cis racemate was further resolved by using the Preparative ChiralPak AD column (eluant: 5% ethanol/95% hexanes). LC-MS for C$_{24}$H$_{35}$F$_3$N$_3$O$_2$ calculated 453.26, found [M+H]$^+$ 454.3.

EXAMPLE 18

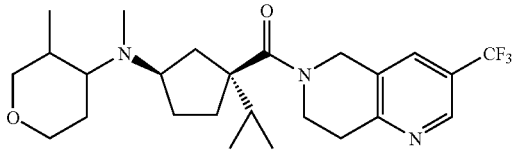

To a solution of a single isomer described in Example 17 (40 mg, 0.088 mmol) and crushed 4 Å molecular sieves (20 mg) in dichloromethane (5 mL) was added formalin (0.1 mL) and the resulting suspension was stirred for 30 min at room temperature. This mixture was then treated with sodium triacetoxyborohydride (93 mg, 0.44 mmol) and stirred an addition 15 h at room temperature. The reaction was quenched with saturated sodium bicarbonate solution (10 mL) and diluted with an additional 10 mL of dichloromethane. The organic layer was separated and the aqueous layer was washed with dichloromethane (2×20 mL). The organics were combined, dried over anhydrous sodium sulfate, filtered and evaporated under reduced pressure. The residue was purified by preparative TLC (eluant: 0.5% NH$_4$OH/5% methanol/94.5% CH$_2$Cl$_2$) to yield 34 mg (83%) of the final product. This reaction was performed the same way for the other isomers.

EXAMPLE 19

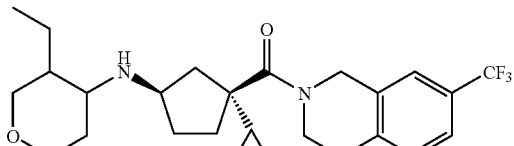

This product was prepared in an analogous fashion to that of Example 17, except Intermediate 1 was replaced with Intermediate 2. Purification by preparative TLC (eluant: 0.5% NH$_4$OH/5% methanol/94.5% CH$_2$Cl$_2$) afforded 203 mg (92%) as a mixture of four diastereomers. The single isomers were obtained by purification on an HPLC equipped with a Preparative ChiralCel OD column eluting with 5% ethanol/95% hexanes with a flow rate of 9 mL/min. LC-MS for C$_{25}$H$_{36}$F$_3$N$_3$O$_2$ calculated 467.28, found [M+H]$^+$ 468.3 for all 4 isomer.

EXAMPLE 20

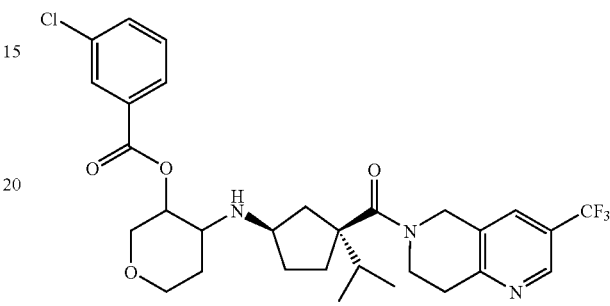

This product was prepared in an analogous fashion to Example 17, except Intermediate 1 was replaced with Intermediate 5. Purification by afforded 312 mg (88%) as a mixture of four diastereomers. LC-MS for C$_{30}$H$_{36}$ClF$_3$N$_3$O$_4$ calculated 593.23, found [M+H]$^+$ 594.3.

EXAMPLE 21

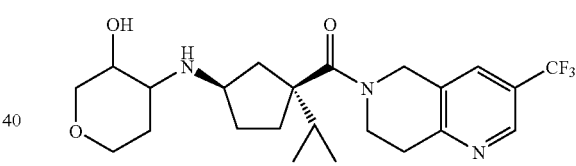

To the solution of the product described in Example 20 (286 mg, 0.482 mmol) in methanol (5 mL) was added a solution of 0.5 M sodium methoxide in methanol (1.2 mL, 0.58 mmol) and the resulting mixture was stirred at room temperature for 2 h. After completion of reaction, the mixture was evaporated in vacuo and purified by preparative TLC (eluant: 1.0% NH$_4$OH/10% methanol/89% CH$_2$Cl$_2$) to yield Example 21 (201 mg, 91.6%) as a mixture of four diastereomers. LC-MS for C$_{23}$H$_{33}$F$_3$N$_3$O$_3$ calculated 455.24, found [M+H]$^+$ 456.25.

EXAMPLE 22

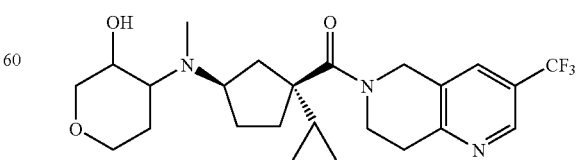

This product was prepared in an analogous fashion to Example 2. The crude product was purified by Preparative TLC (eluant: 1.0% NH₄OH/10% methanol/89% CH₂Cl₂) to afford Example 22. All four isomers were separately reacted to give four single compounds. LC-MS for each diastereomer: $C_{24}H_{35}F_3N_3O_3$ calculated 469.24, found $[M+H]^+$ 470.3.

EXAMPLE 23

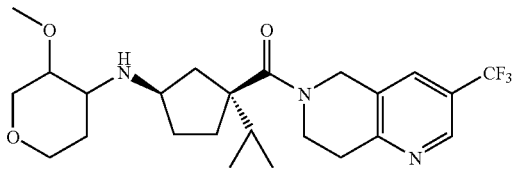

A solution of Intermediate 19 (500 mg, 1.17 mmol), Intermediate 3 (458 mg, 3.51 mmol), diisopropylethylamine (407 μL, 2.34 mmol) and crushed molecular sieves (4 Å, 250 mg) in dichloromethane (25 mL) was treated with sodium triacetoxyborohydride (1.24 g, 5.85 mmol) and stirred at room temperature overnight. The reaction was quenched with saturated sodium bicarbonate solution (25 mL) and diluted with an additional 25 mL of dichloromethane. The organic layer was separated and the aqueous layer was washed with dichloromethane (2×20 mL). The organics were combined, dried over anhydrous sodium sulfate, filtered and evaporated under reduced pressure. The residue was purified by preparative TLC (eluant: 1.0% NH₄OH/10% methanol/89% CH₂Cl₂) to yield 210 mg (86%) of the final product as a mixture of four diastereomers. The single isomers were obtained by using an HPLC equipped with a Preparative ChiralCel OD column eluting with 20% ethanol and 80% hexanes with a flow rate of 9 mL/min. LC-MS calculated for $C_{24}H_{34}F_3N_3O_3$ is 469.21, found $[M+H]^+$ 470.2 for all 4 isomer. 3$^{rd}$ isomer off OD ChiralCel Column: ¹H NMR (500 MHz, CDCl₃) d 8.72 (s, 1H), 7.69 (s, 1H), 4.87 (br d, J=17.2 Hz, 1H), 4.75 (d, J=17.4 Hz, 1H), 4.12 (dd, J=3.1, 12.4 Hz, 1H), 3.99–3.86 (m, 3H), 3.47–3.39 (m, 1H), 3.41 (s, overlapped, 3H), 3.35–3.30 (m, 2H), 3.20–3.08 (m, 3H), 2.87–2.80 (m, 3H), 2.62–2.54 (m, 1H), 2.16–2.02 (m, 2H), 1.95 (br s, 1H), 1.88–1.81 (m, 1H), 1.78–1.57 (m, 6H), 1.41–1.32 (m, 1H), 0.96 (d, J=6.7 Hz, 3H), 0.84 (d, J=6.6 Hz, 3H). 4$^{th}$ isomer off OD ChiralCel Column: ¹H NMR (500 MHz, CDCl₃) d¹H NMR (500 MHz, CDCl₃) d8.72 (s, 1H), 7.69 (s, 1H), 4.87 (br d, J=17.6 Hz, 1H), 4.75 (d, J=17.5 Hz, 1H), 4.10 (dd, J=3.1, 12.3 Hz, 1H), 3.99–3.88 (m, 3H), 3.46–3.39 (m, 1H), 3.41 (s, overlapped, 3H), 3.35–3.30 (m, 2H), 3.17–3.09 (m, 3H), 2.86–2.80 (m, 1H), 2.64–2.55 (m, 1H), 2.16–2.10 (m, 1H), 2.05 (br s, 1H), 1.95–1.82 (m, 2H), 1.76–1.55 (m, 6H), 1.33–1.24 (m, 1H), 0.95 (d, J=6.7 Hz, 3H), 0.83 (d, J=6.6 Hz, 3H).

EXAMPLE 24

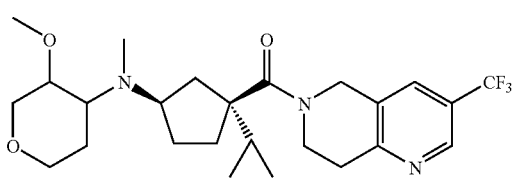

To a solution of a single isomer described in Example 23 (100 mg, 0.203 mmol) and crushed 4 Å molecular sieves (200 mg) in dichloromethane (7 mL) was added formalin (0.2 mL) and the resulting suspension was stirred for 30 min at room temperature. This mixture was then treated with sodium triacetoxyborohydride (215 mg, 1.01 mmol) and stirred an addition 15 h at room temperature. The reaction was quenched with saturated sodium bicarbonate solution (10 mL) and diluted with an additional 10 mL of dichloromethane. The organic layer was separated and the aqueous layer was washed with dichloromethane (2×20 mL). The organics were combined, dried over anhydrous sodium sulfate, filtered and evaporated under reduced pressure. The residue was purified by preparative TLC (eluant: 0.5% NH₄OH/5% methanol/94.5% CH₂Cl₂) to yield 97 mg (95%) of the final product. This reaction was performed the same way for the other three isomers.

EXAMPLE 25

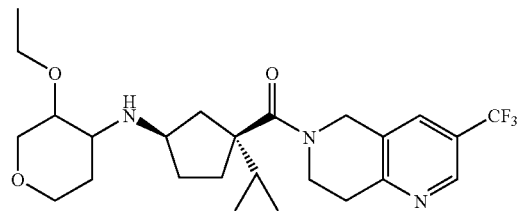

This product was prepared in an analogous fashion to that of Example 17, except Intermediate 1 was replaced with Intermediate 4. The single isomers were obtained by using an HPLC equipped with a Preparative ChiralCel OD column eluting with 15% ethanol and 85% hexanes with a flow rate of 9 mL/min. LC-MS for $C_{25}H_{36}F_3N_3O_3$ calculated 483.23, found $[M+H]^+$ 484.2 for all four isomer.

EXAMPLE 26

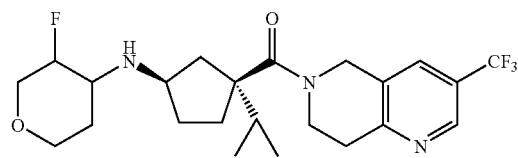

This product was prepared in an analogous fashion to Example 17, except Intermediate 1 was replaced with Intermediate 6. LC-MS for $C_{24}H_{31}F_4N_3O_2$ calculated 457.23, found $[M+H]^+$ 458.2.

EXAMPLE 27

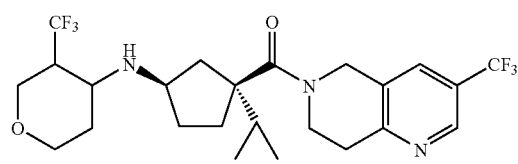

This product was prepared in an analogous fashion to Example 17, except Intermediate 1 was replaced with Intermediate 7. The single isomers were obtained by using an HPLC equipped with a Preparative ChiralCel OD column eluting with 5% ethanol and 95% hexanes with a flow rate of 9 mL/min. LC-MS for $C_{24}H_{31}F_6N_3O_2$ calculated 507.23, found [M+H]$^+$ 508.2 for all isomer.

EXAMPLE 28

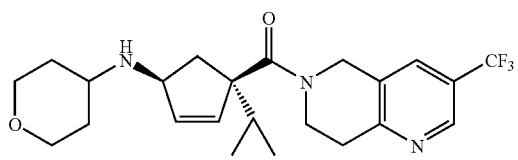

A solution of Intermediate 22 (35 mg, 0.090 mmol), tetrahydro-4H-pyran-4-one (13 mg, 0.14 mmol), diisopropylethylamine (32 μL, 0.18 mmol) and crushed molecular sieves (4 Å, 20 mg) in dichloromethane (10 mL) was treated with sodium triacetoxyborohydride (96 mg, 0.45 mmol) and stirred at room temperature overnight. The reaction was quenched with saturated sodium bicarbonate solution (15 mL) and diluted with an additional 15 mL of dichloromethane. The organic layer was separated and the aqueous layer was washed with dichloromethane (2×10 mL). The organics were combined, dried over anhydrous sodium sulfate, filtered and evaporated under reduced pressure. The residue was purified by preparative TLC (eluant: 0.5% NH$_4$OH/5% methanol/94.5% CH$_2$Cl$_2$) to yield 30 mg (74%) of the final product. LC-MS calculated for $C_{23}H_{30}F_3N_3O_2$ is 437.23, found [M+H]$^+$ 438.3.

EXAMPLE 29

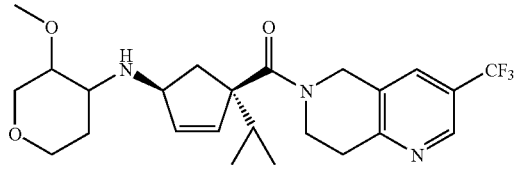

This product was prepared in an analogous fashion to Example 28, except tetrahydro-4H-pyran-4-one was replaced with Intermediate 3. The single isomers were obtained by using an HPLC equipped with a Preparative ChiralCel OD column eluting with 13% ethanol and 87% hexanes with a flow rate of 9 mL/min. LC-MS for $C_{24}H_{32}F_3N_3O_3$ calculated 467.23, found [M+H]$^+$ 468.2 for all isomers.

EXAMPLE 30

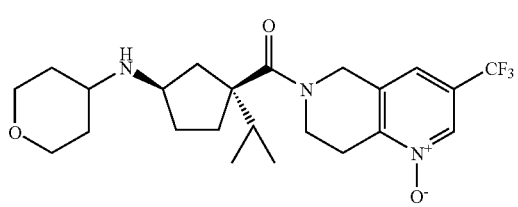

A solution of intermediate 20 (641 mg, 1.60 mmol), tetrahydro-4H-pyran-4-one (220 mg, 2.24 mmol), diisopropylethylamine (279 μL, 1.60 mmol) and crushed molecular sieves (4 Å, 320 mg) in dichloromethane (20 mL) was treated with sodium triacetoxyborohydride (1.70 g, 8.00 mmol) and stirred at room temperature for no longer than 5 h. The reaction was quenched with saturated sodium bicarbonate solution (50 mL) and diluted with an additional 30 mL of dichloromethane. The organic layer was separated and the aqueous layer was washed with dichloromethane (2×30 mL). The organics were combined, dried over anhydrous sodium sulfate, filtered and evaporated under reduced pressure. The residue was purified by preparative TLC (eluant: 0.75% NH$_4$OH/7.5% methanol/91.75% CH$_2$Cl$_2$) to yield 626 mg (86%) of the final product. $^1$H NMR (500 MHz, CDCl$_3$) δ 8.45, (s, 3H), 7.25 (s, 1H), 4.88 (br d, J=17.4 Hz, 1H), 4.77 (d, J=17.6 Hz, 1H), 4.00–3.85 (m, 4H), 3.41 (app t, J=11.7 Hz, 2H), 3.22 (p, J=6.8 Hz, 1H), 3.13–3.07 (m, 2H), 2.82–2.74 (m, 1H), 2.54–2.47 (m, 1H), 2.14 (dd, J=6.8, 12.8 Hz, 1H), 2.07–2.00 (m, 1H), 1.94–1.86 (m, 2H), 1.84–1.77 (m, 3H), 1.65–1.57 (m, 2H), 1.46–1.26 (m, 3H), 0.93 (d, J=6.8 Hz, 3H), 0.83 (d, J 6.8 Hz, 3H): LC-MS for $C_{23}H_{32}F_3N_3O_3$ calculated 455.24, found [M+H]$^+$ 456.2.

EXAMPLE 31

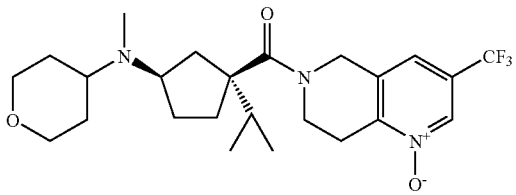

To a solution of product described in Example 30 (100 mg 0.203 mmol) and crushed 4 Å molecular sieves (150 mg) in dichloromethane (7 mL) was added formalin (0.2 mL) and the resulting suspension was stirred for 30 min at room temperature. This mixture was then treated with sodium triacetoxyborohydride (215 mg, 1.01 mmol) and stirred an addition 5 h at room temperature. The reaction was quenched with saturated sodium bicarbonate solution (10 mL) and diluted with an additional 10 mL of dichloromethane. The organic layer was separated and the aqueous layer was washed with dichloromethane (2×20 mL). The organics were combined, dried over anhydrous sodium sulfate, filtered and evaporated under reduced pressure. The crude product was purified by Preparative TLC to afford Example 20 (97 mg, 95%). LC-MS for $C_{24}H_{34}F_3N_3O_3$ calculated 469.24, found [M+H]$^+$ 470.2.

EXAMPLE 32

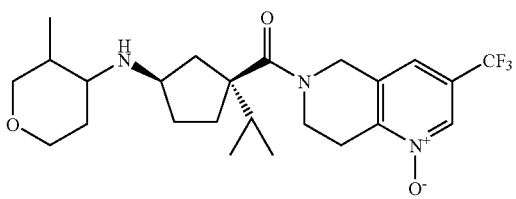

This product was prepared in an analogous fashion to Example 30, except tetrahydro-4H-pyran-4-one was replaced with Intermediate 1. The single isomers were

EXAMPLE 33

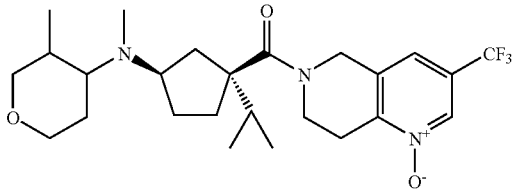

This product was prepared in an analogous fashion to Example 31. The crude product was purified by Preparative TLC (eluant: 1.0% NH$_4$OH/10% methanol/89% CH$_2$Cl$_2$) to afford Example 33. All four isomers were separately reacted to give four single compounds. LC-MS for each diastereomer: C$_{25}$H$_{36}$F$_3$N$_3$O$_3$ calculated 483.24, found [M+H]$^+$ 484.4.

EXAMPLE 34

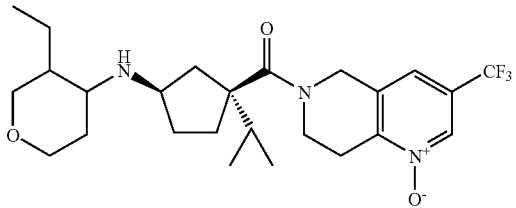

This product was prepared in an analogous fashion to Example 30, except tetrahydro-4H-pyran-4-one was replaced with Intermediate 2. The single isomers were obtained by using an HPLC equipped with a Preparative ChiralCel OD column eluting with 5% ethanol and 95% hexanes with a flow rate of 9 mL/min. LC-MS for C$_{25}$H$_{34}$F$_3$N$_3$O$_3$ calculated 483.24, found [M+H]$^+$ 484.2, for all four isomer.

EXAMPLE 35

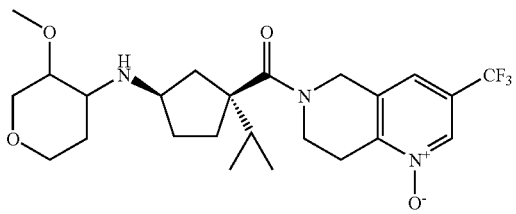

This product was prepared in an analogous fashion to Example 30, except tetrahydro-4H-pyran-4-one was replaced with Intermediate 3. The single isomers were obtained by using an HPLC equipped with a Preparative ChiralCel OD column eluting with 21% ethanol and 79% hexanes with a flow rate of 9 mL/min. LC-MS for C$_{24}$H$_{34}$F$_3$N$_3$O$_4$ calculated 485.25, found [M+H]$^+$ 486.3, for all four isomer.

EXAMPLE 36

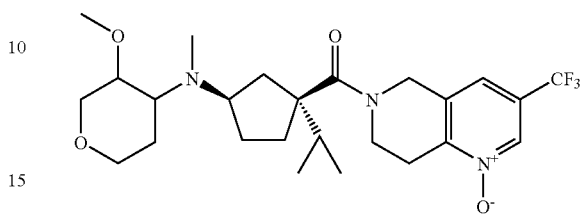

This product was prepared in an analogous fashion to Example 31. The crude product was purified by Preparative TLC (eluant: 1.0% NH$_4$OH/10% methanol/89% CH$_2$Cl$_2$) to afford Example 36. All four isomers were separately reacted to give four single compounds. LC-MS for each diastereomer: C$_{25}$H$_{36}$F$_3$N$_3$O$_4$ calculated 499.24, found [M+H]$^+$ 500.3.

EXAMPLE 37

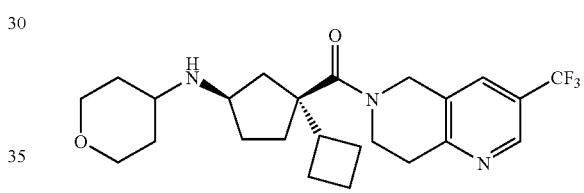

Step A:

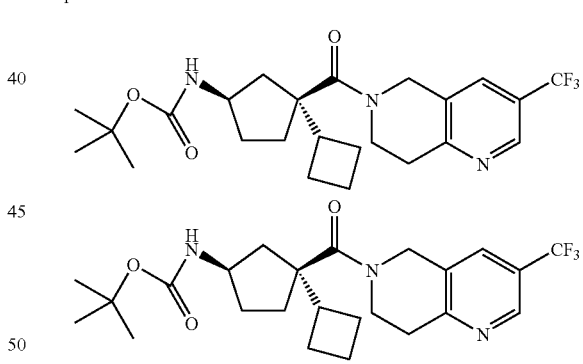

Intermediate 8 (28 g, 0.10 mmol) and Intermediate 14 (25 mg, 0.088 mmol) were first dried by azeotropic distillation with toluene (3×10 mL) and placed under high vacuum for 30 min. Under nitrogen, 4-dimethylaminopyridine (7 mg, 0.053 mmol), anhydrous dichloromethane (1.0 mL), and diisopropylethylamine (30 µL, 0.175 mmol) were added sequentially. After Intermediate 8 was in solution, bromo-tris-pyrrolidino-phosphonium hexafluorophosphate (42 mg, 0.088 mmol) was added, immediately followed by additional diisopropylethylamine (30 µL, 0.17 mmol). The reaction mixture was stirred at room temperature overnight and then quenched with saturated NaHCO$_3$. The aqueous layer was back washed with dichloromethane (3×5 mL) and the organic layers were combined, dried over Na$_2$SO$_4$, filtered, and evaporated in vacuo. The crude product was purified by preparative TLC (eluant: 40% ethyl acetate/60% hexanes) to afford the product (21 mg, 51%) as a clear film. LC-MS for $C_{24}H_{32}F_3N_3O_3$ calculated 467.24, found $[M+H-100(Boc)]^+$ 368.2.

Step B:

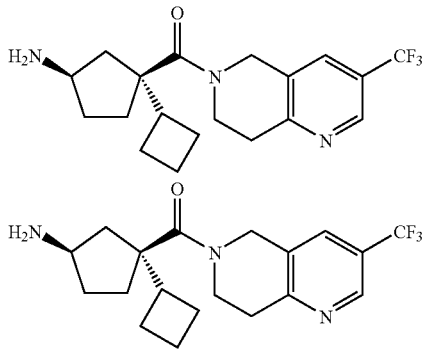

The product described in Step B, Example 37 (21 g, 0.045 mmol) was dissolved in 4 N HCl in dioxane (2.0 mL) and the resulting solution was stirred at room temperature for 1 h. The reaction was evaporated under vacuum to afford the product (20 mg, 100%) as a white powder. LC-MS for $C_{18}H_{24}F_3N_3O$ calculated 367.20, found $[M+H]^+$ 368.2.

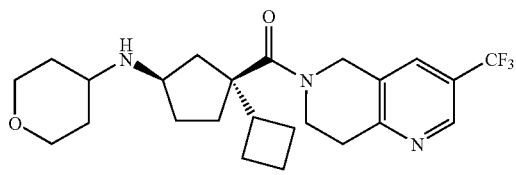

A solution of the product described in Step B, Example 37 (20 mg, 0.045 mmol), tetrahydro-4H-pyran-4-one (9 mg, 0.09 mmol), diisopropylethylamine (16 μL, 0.090 mmol) and crushed molecular sieves (4 Å, 15 mg) in dichloromethane (1.0 mL) was treated with sodium triacetoxyborohydride (48 mg, 0.22 mmol) and stirred at room temperature overnight. The reaction was quenched with saturated sodium bicarbonate solution (10 mL) and diluted with an additional 10 mL of dichloromethane. The organic layer was separated and the aqueous layer was washed with dichloromethane (10 mL). The organics were combined, dried over anhydrous sodium sulfate, filtered and evaporated under reduced pressure. The residue was purified by preparative TLC (eluant: 0.5% NH$_4$OH/5% methanol/94.5% CH$_2$Cl$_2$) to yield 18 mg (88%) of the final product. LC-MS for $C_{24}H_{32}F_3N_3O_2$ calculated 451.24, found $[M+H]^+$ 452.2.

EXAMPLE 38

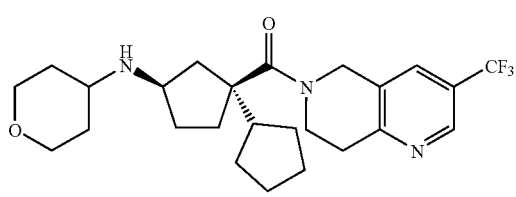

Step A:

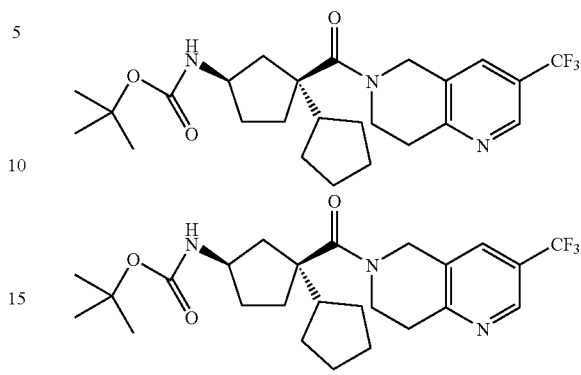

Intermediate 8 (250 mg, 0.81 mmol) and Intermediate 15 (280 mg, 1.00 mmol) were first dried by azeotropic distillation with toluene (3×10 mL) and placed under high vacuum for 30 min. Under nitrogen, 4-dimethylaminopyridine (65 mg, 0.53 mmol), anhydrous dichloromethane (3.0 mL), and diisopropylethylamine (350 μL, 2.02 mmol) were added sequentially. After Intermediate 8 was in solution, bromo-tris-pyrrolidino-phosphonium hexafluorophosphate (378 mg, 0.810 mmol) was added, immediately followed by additional diisopropylethylamine (350 μL, 2.02 mmol). The reaction mixture was stirred at room temperature overnight and then quenched with saturated NaHCO$_3$. The aqueous layer was back extracted with dichloromethane (3×10 mL) and the organic layers were combined, dried over Na$_2$SO$_4$, filtered, and evaporated in vacuo. The crude product was purified by preparative TLC (eluant: 20% ethyl acetate/80% hexanes) to afford the product (192 mg, 50%) as a white foam. LC-MS for $C_{25}H_{34}F_3N_3O_3$ calculated 481.24, found $[M+H-100(Boc)]^+$ 382.2.

Step B:

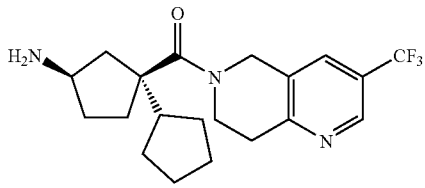

The product described in Step B, Example 38 (100 mg, 0.21 mmol) was dissolved with 4 N HCl in dioxane (5.0 mL) and the resulting solution was stirred at room temperature for 1 h. The reaction was evaporated under vacuum to afford the product (91 mg, 96%) as a white powder. LC-MS for $C_{18}H_{24}F_3N_3O$ calculated 381.20, found $[M+H]^+$ 382.2.

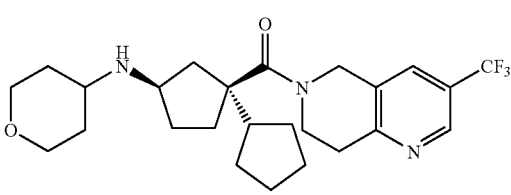

A solution of the product described in Step B, Example 38 (91 mg, 0.20 mmol), tetrahydro-4H-pyran-4-one (30 mg, 0.30 mmol), diisopropylethylamine (70 µL, 0.40 mmol) and crushed molecular sieves (4 Å, 45 mg) in dichloromethane (7.0 mL) was treated with sodium triacetoxyborohydride (212 mg, 1.00 mmol) and stirred at room temperature overnight. The reaction was quenched with saturated sodium bicarbonate solution (20 mL) and diluted with an additional 10 mL of dichloromethane. The organic layer was separated and the aqueous layer was washed with dichloromethane (2×10 mL). The organics were combined, dried over anhydrous sodium sulfate, filtered and evaporated under reduced pressure.

The residue was purified by preparative TLC (eluant: 0.5% $NH_4OH$/5% methanol/94.5% $CH_2Cl_2$) to yield 82 mg (77%) of the final product. LC-MS for $C_{25}H_{34}F_3N_3O_2$ calculated 465.24, found $[M+H]^+$ 466.2.

EXAMPLE 39

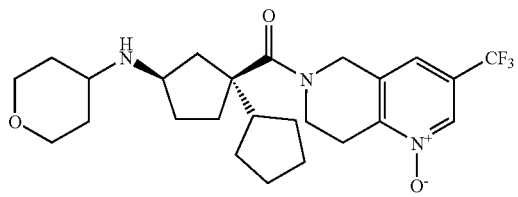

Step A:

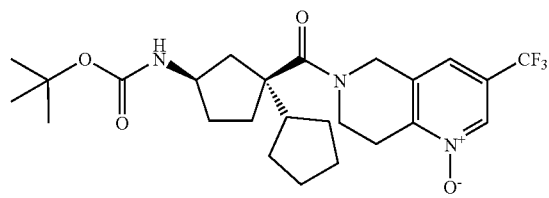

To a solution of the product described in Step A, Example 38 (100 mg, 0.208 mmol) in dichloromethane (5 mL) was added 3-chloroperoxybenzoic acid (93 mg, 0.42 mmol) and the resulting solution was stirred overnight at room temperature. The mixture was cooled to 0° C. and while stirring vigorously solid calcium hydroxide was added in portions until about 1 gram was added. The suspension was stirred for an additional 30 min, then filtered through celite to remove all solids. The filtrate was evaporated in vacuo and the residue purified by preparative TLC (eluant: 70% ethyl acetate/30% hexanes) to afford 79 mg (77%) of the desired compound. LC-MS for $C_{25}H_{34}F_3N_3O_4$ calculated 497.20, found $[M+H]^+$ 498.2.

Step B:

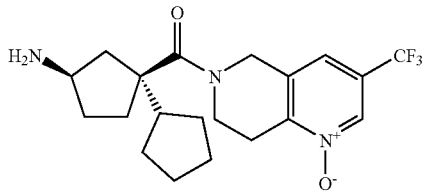

The product described in Step B, Example 39 (75 mg, 0.151 mmol) was dissolved in 4 N HCl in dioxane (4 mL) and the resulting solution was stirred at room temperature for 1 h. The reaction was evaporated under vacuum to afford the product (64 mg, 98%) as a white powder. LC-MS for $C_{18}H_{24}F_3N_3O_2$ calculated 397.20, found $[M+H]^+$ 398.2.

Step C:

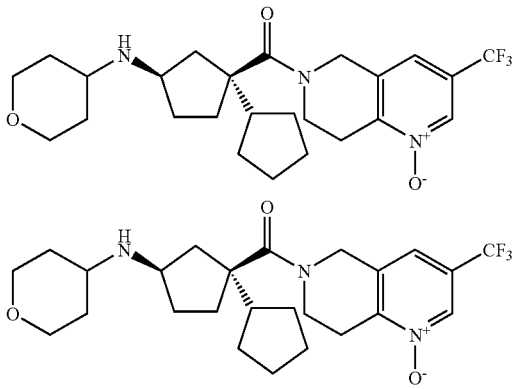

To a solution of the product described in Step C, Example 39 (64 mg 0.15 mmol), tetrahydro-4H-pyran-4-one (22 mg, 0.22 mmol), diisopropylethylamine (26 µL, 0.149 mmol) and crushed molecular sieves (4 Å, 30 mg) in dichloromethane (5 mL) was treated with sodium triacetoxyborohydride (158 mg; 0.745 mmol) and stirred at room temperature for no longer than 5 h. The reaction was quenched with saturated sodium bicarbonate solution (10 mL) and diluted with an additional 10 mL of dichloromethane. The organic layer was separated and the aqueous layer was washed with dichloromethane (2×10 mL). The organics were combined, dried over anhydrous sodium sulfate, filtered and evaporated under reduced pressure. The residue was purified by preparative TLC (eluant: 0.75% $NH_4OH$/7.5% methanol/91.75% $CH_2Cl_2$) to yield 52 mg (68%) of the final product. LC-MS for $C_{25}H_{34}F_3N_3O_3$ calculated 482.24, found $[M+H]^+$ 483.3.

EXAMPLE 40

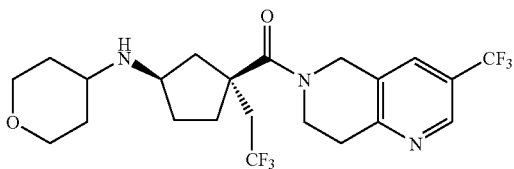

A solution of intermediate 23 (65 mg, 0.14 mmol), tetrahydro-4H-pyran-4-one (26 mg, 0.28 mmol), diisopropylethylamine (25 µL, 0.14 mmol) and crushed molecular sieves (4 Å, 35 mg) in dichloromethane (5 mL) was treated with sodium triacetoxyborohydride (148 mg, 0.700 mmol) and stirred at room temperature overnight. The reaction was quenched with saturated sodium bicarbonate solution (10 mL) and diluted with an additional 15 mL of dichloromethane. The organic layer was separated and the aqueous layer was washed with dichloromethane (2×10 mL). The organics were combined, dried over anhydrous sodium sulfate, filtered and evaporated under reduced pressure. The crude product was purified by reverse phase HPLC to yield the final product (42 mg, 63%). LC-MS for $C_{22}H_{27}F_6N_3O_2$ calculated 479.20, found $[MH]^+$ 480.25.

EXAMPLE 41

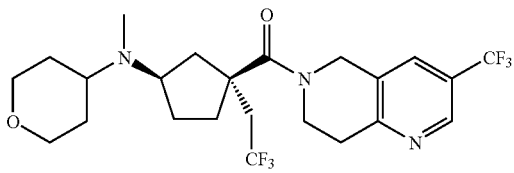

To a solution of product described in Example 40 (40 mg 0.083 mmol) and crushed 4 Å molecular sieves (20 mg) in dichloromethane (5 mL) was added formalin (0.1 mL) and the resulting suspension was stirred for 30 min at room temperature. This mixture was then treated with sodium triacetoxyborohydride (89 mg, 0.42 mmol) and stirred an addition 15 h at room temperature. The reaction was quenched with saturated sodium bicarbonate solution (10 mL) and diluted with an additional 10 mL of dichloromethane. The organic layer was separated and the aqueous layer was washed with dichloromethane (2×20 mL). The organics were combined, dried over anhydrous sodium sulfate, filtered and evaporated under reduced pressure. The crude product was purified by reverse phase HPLC to yield Example 41 (37.5 mg, 92%). LC-MS for $C_{23}H_{29}F_6N_3O_2$ [M$^+$H$^+$] calculated 493.22, found [MH]$^+$ 494.2.

EXAMPLE 42

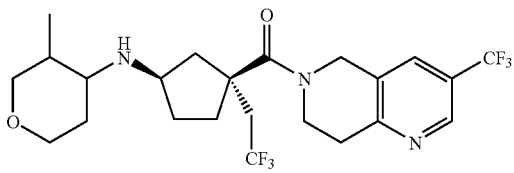

This product was prepared in an analogous fashion to Example 40, except tetrahydro-4H-pyran-4-one was replaced with Intermediate 1. The single isomers were obtained by using an HPLC equipped with a Preparative ChiralCel OD column eluting with 4% ethanol and 96% hexanes with a flow rate of 9 mL/min. LC-MS for $C_{23}H_{29}F_6N_3O_2$ calculated 493.22, found [M+H]$^+$ 494.2, for all four isomer.

TABLE 1

The table below shows examples synthesized in a similar fashion to Example 40 and 41 above, where the tetrahydropyran is replaced with some substituted tetrahydropyrans.

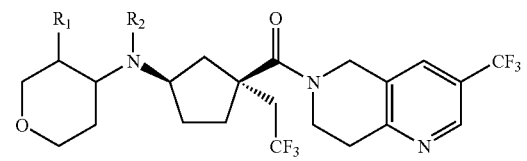

| EXAMPLE | R1 | R2 | Column and eluant | FW: formula/found [M+H]$^+$ |
|---|---|---|---|---|
| 43 | CH$_3$ | CH$_3$ | Single isomers obtained from Example 31 | $C_{24}H_{31}F_6N_3O_2$ 508.2 |
| 44 | OMe | H | Preparative ChiralCel OD 93% Hexane: 7% Ethanol | $C_{23}H_{29}F_6N_3O_3$ 510.2 |
| 45 | OMe | CH$_3$ | Single isomers obtained from Example 34 | $C_{24}H_{31}F_6N_3O_3$ 524.2 |
| 46 | F | H | Preparative ChiralCel OD 90% Hexane: 10% Ethanol | $C_{22}H_{26}F_7N_3O_2$ 498.1 |
| 47 | CF$_3$ | H | Preparative ChiralCel OD 97% Hexane: 3% Ethanol | $C_{23}H_{26}F_9N_3O_2$ 548.3 |

EXAMPLE 48

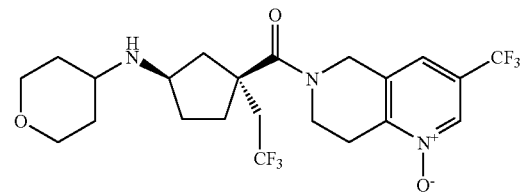

A solution of intermediate 24 (250 mg, 0.558 mmol), tetrahydro-4H-pyran-4-one (90 mg, 0.84 mmol), diisopropylethylamine (100 µL, 0.558 mmol) and crushed molecular sieves (4 Å, 150 mg) in dichloromethane (10 mL) was treated with sodium triacetoxyborohydride (590 mg, 2.79 mmol) and stirred at room temperature for no longer than 5 h. The reaction was quenched with saturated sodium bicarbonate solution (20 mL) and diluted with an additional 20 mL of dichloromethane. The organic layer was separated and the aqueous layer was washed with dichloromethane (2×20 mL). The organics were combined, dried over anhydrous sodium sulfate, filtered and evaporated under reduced pressure. The residue was purified by preparative TLC (eluant: 1.0% NH$_4$OH/10% methanol/89% CH$_2$Cl$_2$) to yield 191 mg (70%) of the final product. LC-MS for $C_{22}H_{27}F_6N_3O_3$ calculated 495.24, found [M+H]$^+$ 4.96.2.

EXAMPLE 49

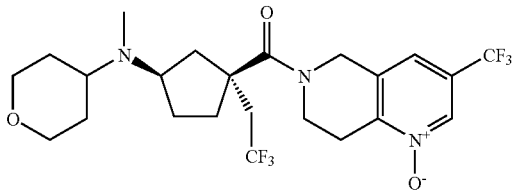

To a solution of the product described in Example 48 (150 mg 0.302 mmol) and crushed 4 Å molecular sieves (200 mg) in dichloromethane (7 mL) was added formalin (0.3 mL) and the resulting suspension was stirred for 30 min at room temperature. This mixture was then treated with sodium triacetoxyborohydride (321 mg, 1.51 mmol) and stirred an addition 5 h at room temperature. The reaction was quenched with saturated sodium bicarbonate solution (20 mL) and diluted with an additional 20 mL of dichloromethane. The organic layer was separated and the aqueous layer was washed with dichloromethane (2×20 mL). The organics were combined, dried over anhydrous sodium sulfate, filtered and evaporated under reduced pressure. The crude product was purified by Preparative TLC to afford Example 49 (112 mg, 73%). LC-MS for $C_{23}H_{29}F_6N_3O_3$ calculated 509.24, found $[M+H]^+$ 510.2.

EXAMPLE 50

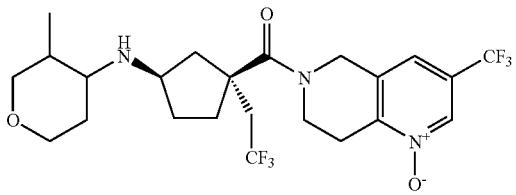

This product was prepared in an analogous fashion to Example 48, except tetrahydro-4H-pyran-4-one was replaced with Intermediate 1. The single isomers were obtained by using an HPLC equipped with a Preparative ChiralCel OD column eluting with 6% ethanol and 94% hexanes with a flow rate of 9 mL/min. LC-MS for $C_{23}H_{29}F_6N_3O_3$ calculated 509.24, found $[M+H]^+$ 510.2., for all four isomer.

EXAMPLE 51

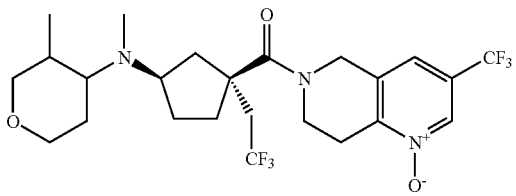

This product was prepared in an analogous fashion to Example 49 from Example 50. The crude product was purified by Preparative TLC (eluant: 1.0% $NH_4OH$:10% methanol:89% $CH_2Cl_2$) to afford Example 51. All four isomers were separately reacted to give four single compounds. LC-MS for each diastereomer: $C_{24}H_{31}F_6N_3O_3$ calculated 515.24, found $[M+H]^+$ 516.3.

EXAMPLE 52

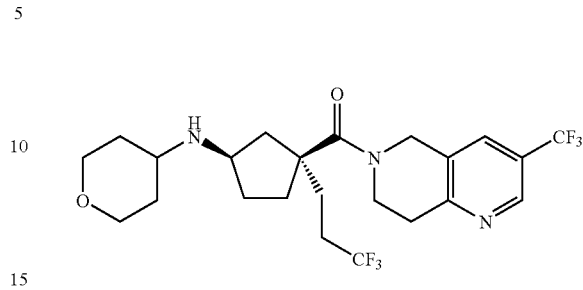

A solution of intermediate 25 (50 mg, 0.11 mmol), tetrahydro-4H-pyran-4-one (21 mg, 0.21 mmol), diisopropylethylamine (37 µL, 0.21 mmol) and crushed molecular sieves (4 Å, 35 mg) in dichloromethane (5 mL) was treated with sodium triacetoxyborohydride (111 mg, 0.525 mmol) and stirred at room temperature overnight. The reaction was quenched with saturated sodium bicarbonate solution (10 mL) and diluted with an additional 15 mL of dichloromethane. The organic layer was separated and the aqueous layer was washed with dichloromethane (2×10 mL). The organics were combined, dried over anhydrous sodium sulfate, filtered and evaporated under reduced pressure. The crude product was purified by preparative TLC (eluant: 0.75% $NH_4OH$/7.5% methanol/91.75% $CH_2Cl_2$) to yield the final product (39 mg, 75%). LC-MS for $C_{23}H_{29}F_6N_3O_2$ calculated 493.20, found $[M+H]^+$ 494.3.

EXAMPLE 53

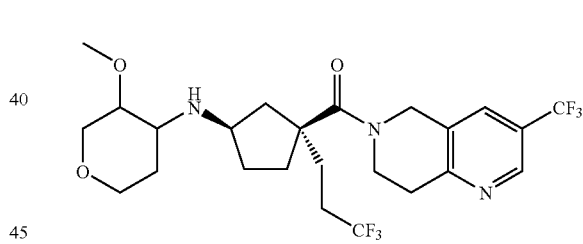

This product was prepared in an analogous fashion to Example 52, except tetrahydro-4H-pyran-4-one was replaced with Intermediate 3. The single isomers were obtained by using an HPLC equipped with a Preparative ChiralCel OD column eluting with 7% ethanol and 93% hexanes with a flow rate of 9 mL/min. LC-MS for $C_{24}H_{31}F_6N_3O_3$ calculated 523.22, found $[M+H]^+$ 524.4, for all four isomer.

EXAMPLE 54

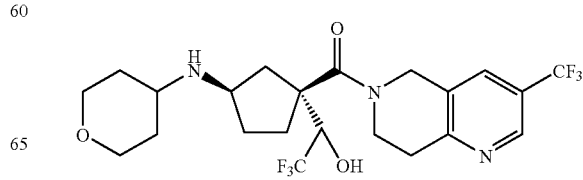

Step A:

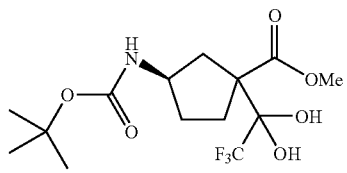

This intermediate was prepared in an analogous fashion to the product described in Step B, Intermediate 12, except 2-iodo-1,1,1-trifluoroethane was replaced with ethyl-1,1,1-trifluoroacetate. Purification by MPLC (gradient eluent 0–40% ethyl acetate/hexanes) afforded the desired compound (4.26 g, 68%) as a 3:2 mixture of diastereoisomers. LC-MS for $C_{14}H_{22}F_3NO_6$ calculated 357.70, found [M+H–100(Boc)]$^+$ 258.1

Step B:

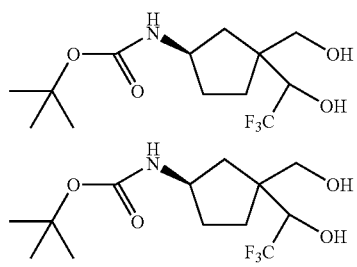

A solution of the product described in Step A, Example 54 (4.0 g, 12 mmol) in methanol (10 mL) was treated with sodium borohydride (1.34 g) and the resulting mixture was stirred at room temperature for 2 h. The reaction was quenched with water (20 mL) and concentrated in vacuo to remove the methanol. The aqueous layer was extracted with ethyl acetate (3×50 mL) and the organics were combined, dried over sodium sulfate, filtered, and evaporated under reduced pressure. Purification by MPLC (gradient eluent 0–75% ethyl acetate/hexanes) gave the product as a clear oil. LC-MS for $C_{134}H_{22}F_3NO_4$ calculated 313.14, found [M+H–100(Boc)]$^+$ 214.1

Step C:

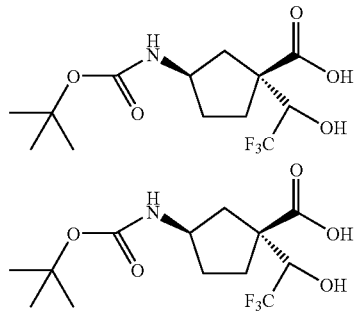

A solution of the product described in Step B, Example 54 (3.5 g, 11 mmol) in chloroform/acetonitrile/water (1:1:1 solution, 63 mL) was treated with sodium periodate (9.56 g, 44.7 mmol) and RuCl$_3$ trihydrate (175 mg, 0.670 mmol) and the resulting dark brown solution was stirred at room temperature for 3 h. The dark brown solution changed to a bright orange after stirring for 3 h. The mixture was diluted with dichloromethane (100 mL) and the layers were separated. The aqueous layer was washed with dichloromethane (2×50 mL) and the organics were combined, dried over sodium sulfate, filtered through celite, and evaporated in vacuo. Purification by flash column (gradient eluent 0–20% methanol/ethyl acetate) afforded two separated isomers as a mixture of 2 diastereoisomers at the hydroxyethyl carbon. The faster eluting isomer was the desired cis isomer (1.45 g, 40%) and the lower eluting isomer was the undesired trans isomer (986 mg, 27%).

Step D:

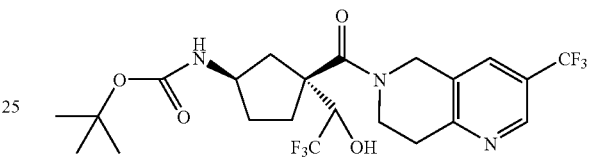

The faster eluting cis isomer described in Step C, Example 54 (326 mg, 1.00 mmol) and Intermediate 8 (412 mg, 1.50 mmol) were first dried by azeotropic distillation with toluene (2×10 mL) and placed under high vacuum for 30 min. Under nitrogen, 4-dimethylaminopyridine (73 mg, 0.60 mmol), anhydrous dichloromethane (4 mL), and diisopropylethylamine (435 µL, 2.50 mmol) were added sequentially. After Intermediate 8 was in solution, bromo-tris-pyrrolidino-phosphonium hexafluorophosphate (466 mg, 1.00 mmol) was added, immediately followed by additional diisopropylethylamine (435 µL, 2.50 mmol). The reaction mixture was stirred at room temperature overnight and then quenched with saturated NaHCO$_3$ solution. The aqueous layer was back extracted with dichloromethane (3×50 mL) and the organic layers were combined, dried over Na$_2$SO$_4$, filtered, and evaporated in vacuo. The crude product was purified by preparative TLC (eluent: 50% ethyl acetate/50% hexanes) to afford two single isomers: higher eluting (126 mg, 25%) and lower eluting (65 mg, 13%) as yellow films. The stereochemistry of the two isomers at the hydroxy-trifluoroethyl carbon is unknown and was not determined. $^1$H NMR (500 MHz, CDCl$_3$), First higher eluting cis isomer δ 8.70, (s, 3H), 7.71 (s, 1H), 5.55 (br s, 1H), 5.10 (br s, 1H), 5.04.86 (m, 1H), 4.78 (d, J=17.6 Hz, 1H), 4.34 (br s, 1H), 4.12–4.04 (m, 1H), 4.02–3.84 (m, 1H), 3.56–3.44 (m, 1H), 3.20–3.06 (m, 2H), 2.64–2.46 (m, 1H), 2.44–2.29 (m, 1H), 2.26–2.16 (m, 1H), 2.12–2.00 (m, 2H), 2.00–1.82 (m, 3H), 1.78–1.66 (m, 1), 1.45 (s, 9H). $^1$H NMR (500 MHz, CDCl$_3$), Second lower eluting cis isomer δ 8.70, (s, 3H), 7.71 (s, 1H), 5.60 (br s, 1H), 4.87 (br d, J=17.2 Hz, 1H), 4.81 (d, J=17.7 Hz, 1H), 4.29 (br s, 1H), 4.20–3.93 (m, 2H), 3.20–3.05 (m, 2H), 2.72–2.56 (m, 1H), 2.26–2.18 (m, 1H), 2.16–2.00 (m, 1H), 2.10–2.04 (m, 1H), 1.98–1.92 (m, 1H), 1.46–1.42 (m, 1H), 1.40 (s, 9H).

Step E:

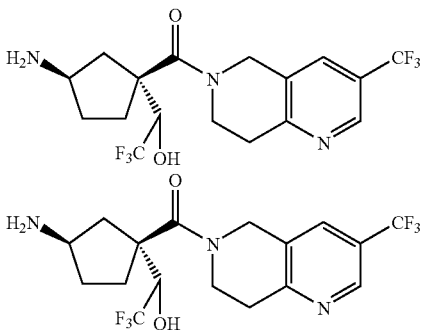

The products described in step D, Example 54 (124 mg, 0.242 mmol, higher eluting isomer and 60 mg, 0.117 mmol, lower eluting isomer) were each dissolved with 4 N HCl in dioxane (5 mL) and the resulting solutions were stirred at room temperature for 1 h. The reactions were evaporated under vacuum to afford the products (higher eluting isomer, 116 mg, 99%, and lower eluting isomer, 53 mg, 94%) as pale white solids. LC-MS for $C_{17}H_{19}F_6N_3O_2$ calculated 412.14, found [M+H]$^+$ 413.15 for both isomers.

Step F: (Higher eluting isomer)

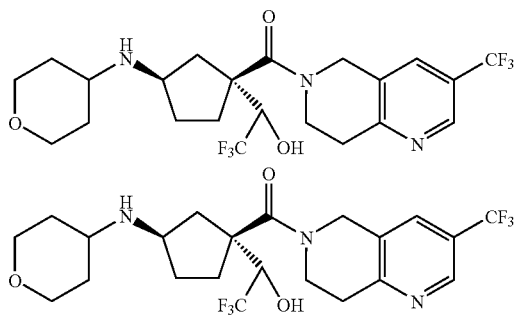

A solution of the higher eluting isomer described in Step E, Example 54 (116 mg, 0.239 mmol), tetrahydro-4H-pyran-4-one (72 mg, 0.72 mmol), diisopropylethylamine (84 µL, 0.47 mmol) and crushed molecular sieves (4 Å, 55 mg) in dichloromethane (5 mL) was treated with sodium triacetoxyborohydride (254 mg, 1.20 mmol) and stirred at room temperature overnight. The reaction was quenched with saturated sodium bicarbonate solution (20 mL) and diluted with an additional 20 mL of dichloromethane. The organic layer was separated and the aqueous layer was washed with dichloromethane (2×10 mL). The organics were combined, dried over anhydrous sodium sulfate, filtered and evaporated under reduced pressure. The crude product was purified by preparative TLC (eluant: 1.0% NH$_4$OH/10% methanol/89% CH$_2$Cl$_2$) to yield the product labeled as the higher isomer (58 mg, 49%). $^1$H NMR (500 MHz, CDCl$_3$), δ 8.73 (s, 1H), 7.70 (s, 1H), 4.86 (s, 2H), 4.17–4.11 (m, 1H), 4.06–3.95 (m, 3H), 3.88 (ddd, J=7.3, 5.0, 13.0 Hz, 1H), 3.42–3.36 (m, 3H), 3.21–3.07 (m, 2H), 2.77–2.70 (m, 1H), 2.60–2.52 (m, 2H), 2.29–2.21 (m, 1H), 2.05 (ddd, J=6.4, 7.0, 12.0 Hz, 1H), 1.92 (dd, J=8.5, 13.0 Hz, 1H), 1.86–1.78 (m, 2H), 1.44–1.30 (m, 4H). LC-MS for $C_{22}H_{27}F_6N_3O_3$ calculated 495.20, found [M+H]$^+$ 496.15.

Step G: (Lower eluting isomer)

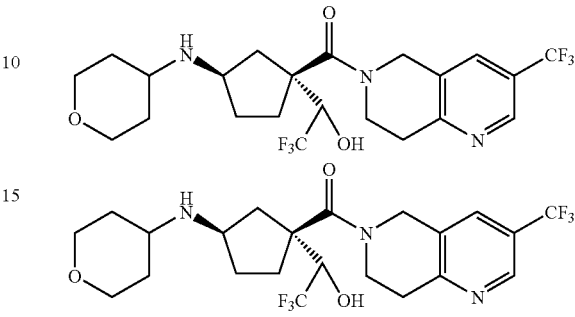

This product was prepared in an analogous fashion to the compound described in Step F, Example 54. The crude product was purified by Preparative TLC (eluant: 1.0% NH$_4$OH/10% methanol/89% CH$_2$Cl$_2$) to afford the product labeled as the lower isomer (32 mg, 67%). $^1$H NMR (500 MHz, CDCl$_3$), δ 8.71 (s, 1H), 7.69 (s, 1H), 4.87 (d, J=17.1 Hz, 1H), 4.78 (br d, J=18.0 Hz, 1H), 4.10 (dd, J=7.0, 14.2 Hz, 1H), 4.06–4.01 (m, 1H), 3.97 (br d, J=11.2 Hz, 2H), 3.88 (ddd, J=5.7, 7.0, 12.7 Hz, 1H), 3.46–3.34 (m, 3H), 3.22–3.07 (m, 2H), 2.76–2.66 (m, 1H), 2.62 (dd, J=6.5, 13.6 Hz, 1H), 2.55–2.48 (m, 1H), 2.14–2.00 (m, 3H), 1.84–1.76 (m, 2H), 1.55 (dd, J=6.5, 6.7, 12.8 Hz, 2H), 1.35–1.26 (m, 4H). LC-MS for $C_{22}H_{27}F_6N_3O_3$ calculated 495.20, found [M+H]$^+$ 496.15.

EXAMPLE 55

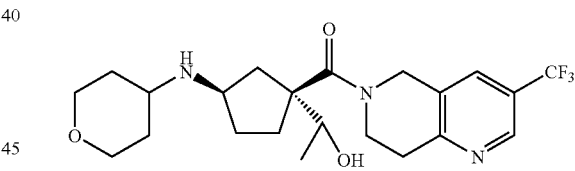

A solution of Intermediate 16 (89 mg, 0.17 mmol), tetrahydro-4H-pyran-4-one (52 mg, 0.52 mmol), diisopropylethylamine (30 µL, 0.17 mmol) and crushed molecular sieves (4 Å, 200 mg) in dichloromethane (6 mL) was treated with sodium triacetoxyborohydride (184 mg, 0.870 mmol) and stirred at room temperature overnight. The reaction was quenched with saturated sodium bicarbonate solution (20 mL) and diluted with an additional 20 mL of dichloromethane. The organic layer was separated and the aqueous layer was washed with dichloromethane (10 mL). The organics were combined, dried over anhydrous sodium sulfate, filtered and evaporated under reduced pressure. The single isomers of the crude product (65.7 mg, 78%) were separated by preparative TLC (CH$_2$Cl$_2$/methanol/NH$_4$OH/ 90:9:1) to yield the final products: Higher eluting isomer: LC-MS for $C_{22}H_{30}F_3N_3O_3$ calculated 441.22, found [M+H]$^+$ 442.30. $^1$H NMR (500 MHz, CDCl$_3$): 8.71 (s, 1H), 7.69 (s, 1H), 4.94 (d, J=17.4 Hz, 1H), 4.78 (d, J=17.40, 1H), 4.0 (m, 4H), 3.40 (m, 3H), 3.12 (m, 2H), 2.80 (bs, 1H), 2.54 (m, 1H), 2.40 (m, 1H), 2.00 (m, 2H), 1.85 (m, 3H), 1.14 (d, J=6.17 Hz, 3H). Lower eluting isomer: MS for C$_{22}$H$_{30}$F$_3$N$_3$O$_3$ calculated 441.22, found [M+H]$^+$ 442.30. $^1$H NMR (500 MHz, CDCl$_3$): 8.71 (s, 1H), 7.69 (s, 1H), 4.96 (m, 1H), 4.78 (d, J=17.40 Hz, 1H), 4.02 (m, 3H), 3.90 (m, 1H), 3.40 (t, J=11.67 Hz, 2H), 3.12 (t, J=5.49 Hz, 2H), 2.84 (bs, 1H), 2.50 (ddd, J=13.04, 8.01, 4.80 Hz, 1H), 2.36 (dd, J=13.50, 6.64 Hz, 1H), 2.05 (bd, J~10 Hz, 2H), 1.88 (m, 3H), 1.50 (bs, 3H), 1.16 (d, 6.41 Hz, 3H).

EXAMPLE 56

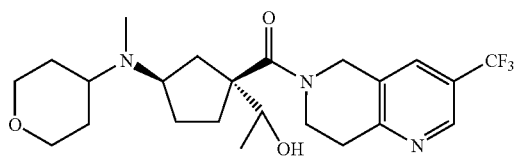

This compound was synthesized from the lower eluting isomer described under Example 55 using a procedure analogous to that detailed in Example 2. MS for C$_{23}$H$_{32}$F$_3$N$_3$O$_3$ calculated 455.24, found [M+H]$^+$ 456.25.

EXAMPLE 57

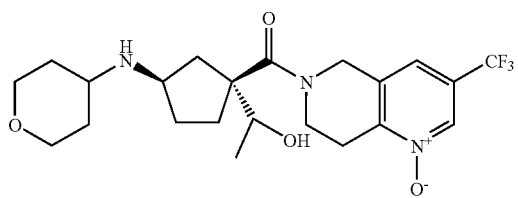

Step A:

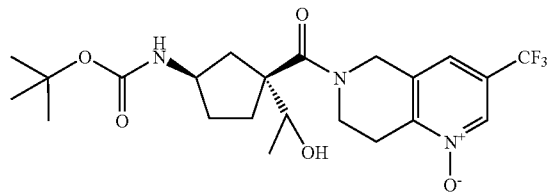

A solution of the amide, the synthesis of which was described under Steps A–E of Intermediate 16 (172 mg, 0.376 mmol) and 3-chloroperoxybenzoic acid (191 mg, 68%, 0.752 mmol) in dichloromethane (5 mL) was stirred at room temperature for 2 h. The reaction was quenched by the careful addition of calcium hydroxide (170 mg, 2.3 mmol), and the stirring was continued for another 30 min. The solid was filtered off and the filtrate was evaporated to dryness to leave 156.6 mg (88%) of the product, which was used in the next reaction step as obtained. MS for C$_{22}$H$_{30}$F$_3$N$_3$O$_5$ calculated 473.21, found [M+H]$^+$ 374.30 (loss of the BOC group).

Step B

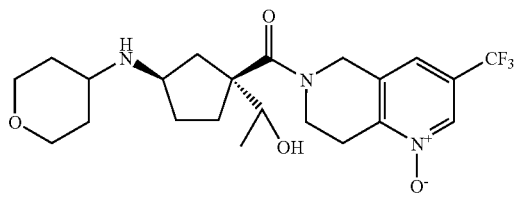

The final compound was synthesized starting from the previously described N-oxide in a series of steps described in Intermediate 16, Step F, followed by the procedure detailed under Example 47, except that the reductive amination step was conducted at room temperature for not longer than 2.5 h. The pure single diastereomers were obtained by separation on chiral IPLC (ChiralCel OD, 15% ethyl alcohol in hexanes, 9.0 mL/min). LC-MS for C$_{22}$H$_{30}$F$_3$N$_3$O$_4$ calculated 457.22, found [M+H]$^+$ 458.20.

EXAMPLE 58

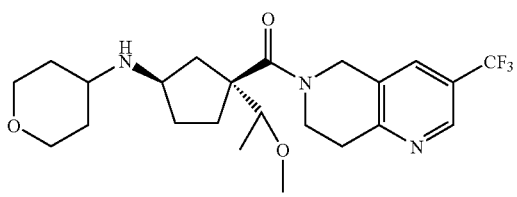

This compound was synthesized from the lower eluting diastereoisomer described in Step A, Intermediate 17 according to the procedure described in Example 55. LC-MS for C$_{23}$H$_{32}$F$_3$N$_3$O$_3$ calculated 455.24, found [M+H]$^+$ 456.25.

EXAMPLE (59–62)

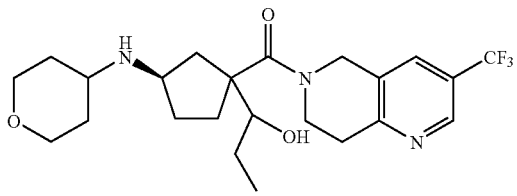

Step A:

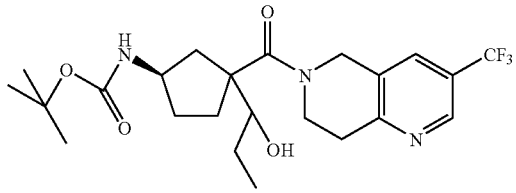

A solution of Intermediate 18 (first eluting isomer, 125 mg, 0.435 mmol), Intermediate 8 (176 g, 0.870 mmol), 1-hydroxy-7-azobenzotriazole (60 mg, 0.435 mmol), and diisopropylethylamine (303 μL, 1.74 mmol) in dichloromethane (5 mL) was treated with 1-(-3-dimethylaminopropyl)-3-ethylcarbodiimide hydrochloride (250 mg, 1.31 mmol) and the resulting mixture was stirred at room temperature overnight. The reaction was quenched with water, and the product was extracted into dichloromethane. The combined organic extracts were dried (anhydrous magnesium sulfate) and the solvent was removed in vacuo. The residue (115 mg) was separated by preparative TLC (eluant: 80% ethyl acetate/20% hexanes) to yield the single isomer (the hydroxypropyl side-chain, isomer 1, 65 mg, 32%) of unknown absolute stereochemistry. All four isomers were prepared as described above to give four single compounds labeled isomers 1–4. LC-MS for C$_{22}$H$_{32}$F$_3$N$_3$O$_4$ calculated 471.23, found [M+H−100(Boc)]$^+$ 372.25 for all four isomers.

Step B

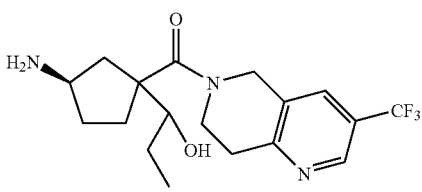

The product described in Step B, Example (59–62) (isomer 1, 65 mg, 0.130 mmol) was dissolved in 4 N HCl in dioxane (2 mL) and the resulting solution was stirred at room temperature for 1 h. The reaction was evaporated under vacuum to afford the product (isomer 1, 61 mg, 99%) as a white solid. The other isomers were also prepared as described above. LC-MS for $C_{18}H_{24}F_3N_3O_2$ calculated 371.23, found [M+H]$^+$ 372.25

Step C

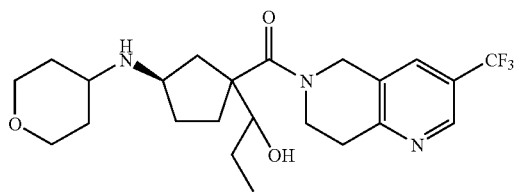

A solution of the product (isomer 1) described in Step B, Example (59–62) (61 mg, 0.14 mmol), tetrahydro-4H-pyran-4-one (27.7 mg, 0.276 mmol), diisopropylethylamine (48 µL, 0.28 mmol) and crushed molecular sieves (4 Å, 50 mg) in dichloromethane (5 mL) was treated with sodium triacetoxyborohydride (147 mg, 0.690 mmol) and stirred at room temperature overnight. The reaction was quenched with saturated sodium bicarbonate solution (20 mL) and diluted with an additional 20 mL of dichloromethane. The organic layer was separated and the aqueous layer was washed with dichloromethane (10 mL). The organics were combined, dried over anhydrous sodium sulfate, filtered and evaporated under reduced pressure. The crude product was purified by preparative TLC (eluant: 1.0% NH$_4$OH/10% methanol/89% CH$_2$Cl$_2$) to yield the final product as a single isomer of unknown absolute stereochemistry (55 mg, 80%). LC-MS for $C_{23}H_{32}F_3N_3O_3$ calculated 455.27, found [M+H]$^+$ 456.3.

TABLE 2

The other three isomers synthesized in a similar fashion to Example 59 are listed in the table below.

| Example | label | Molecular Formula | Calculated [M] | Found [M+H]$^+$ |
|---|---|---|---|---|
| 60 | Isomer 2 2$^{nd}$ fastest eluting isomer | $C_{23}H_{32}F_3N_3O_3$ | 455.27 | 456.3 |
| 61 | Isomer 3 3$^{rd}$ fastest eluting isomer | $C_{23}H_{32}F_3N_3O_3$ | 455.27 | 456.3 |
| 62 | Isomer 4 Last eluting isomer | $C_{23}H_{32}F_3N_3O_3$ | 455.27 | 456.3 |

EXAMPLE 63

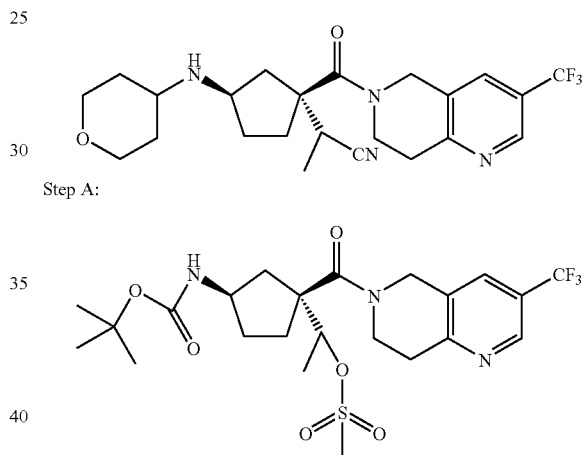

Step A:

A solution of the alcohol from Intermediate 16, Step E (80 mg, 0.18 mmol), triethylamine (122 µL, 0.875 mmol) and a catalytic amount of 4-dimethylaminopyridine in dichloromethane (5 mL) was treated at 0° C. with neat methanesulfonyl chloride (20 µL, 0.26 mmol). The cooling bath was removed, and the reaction mixture was stirred at room temperature for 1 h. It was then diluted with dichloromethane (20 mL), and washed with water (10 mL). After drying with anhydrous sodium sulfate the organic solvent was removed in vacuo, and the crude product (126 mg, 100%) was used immediately in the next reaction step. MS for $C_{23}H_{32}F_3N_3O_6S$ calculated 535.20, found 436.15 [M+H−BOC]$^+$.

Step B

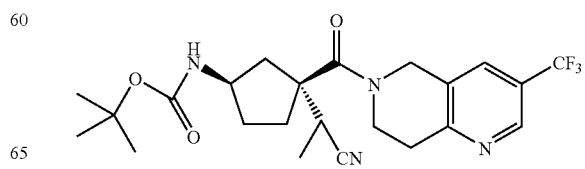

A solution of the mesylate from the previous step (126 mg, 0.175 mmol) and potassium cyanide (114 mg, 1.75 mmol) in N,N-dimethylformamide (4 mL) was degassed by vacuum/nitrogen cycle and heated to 85° C. overnight. The reaction was quenched with water and the product was extracted with a mixture of hexane/diethyl ether (8:2). The combined extracts were dried with anhydrous magnesium sulfate and the solvent was removed in vacuo to yield 77.7 mg (95%) of the desired nitrile. MS for $C_{23}H_{29}F_3N_4O_3$ calculated 466.22, found 367.15 $[M+H-BOC]^+$.

Step C

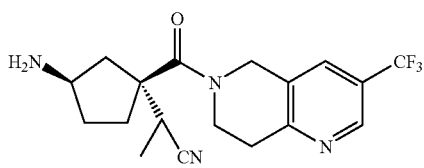

A solution of the nitrile from previous step (80 mg, 0.17 mmol) in dichloromethane (10 mL) was treated with 2 mL of trifluoroacetic acid and stirred at room temperature for 2 h. The solvent was removed in vacuo, and the residual trifluoroacetic acid was co-distilled with toluene two times to yield 148 mg (100%) of the desired amine in a form of a trifluoroacetic acid salt. MS for $C_{18}H_{21}F_3N_4O$ calculated 366.17, found 367.10 $[M+H]^+$.

Step D:

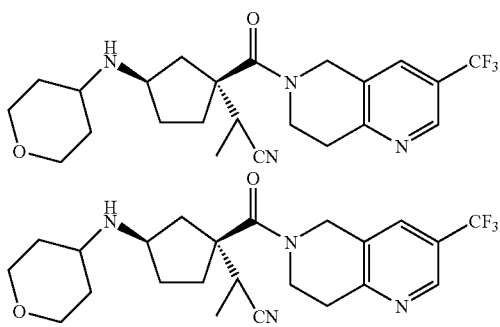

The final compound was synthesized according to the procedure analogous to that described under Example 55. The two respective diastereoisomers were conveniently separated using semi-preparative HPLC on a ChiralCel OD column. The retention times under analogous analytical conditions (ChiralCel OD, 1.0 mL/min, hexanes/ethanol (85:15) were 11.23 min and 18.12 min, respectively. MS for $C_{23}H_{29}F_3N_4O_2$ calculated: 450.22, found: 451.30 $[M+H]^+$.

EXAMPLE 64

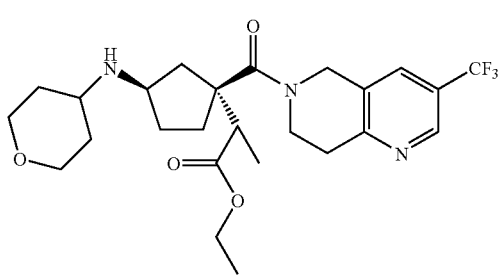

This compound was synthesized in a reductive amination step analogous to that described in Example 55. The respective diastereoisomers were obtained by preparative TLC. MS for $C_{25}H_{34}F_3N_3O_4$ calculated: 497.25, found: 498.30 $[M+H]^+$.

EXAMPLE 65

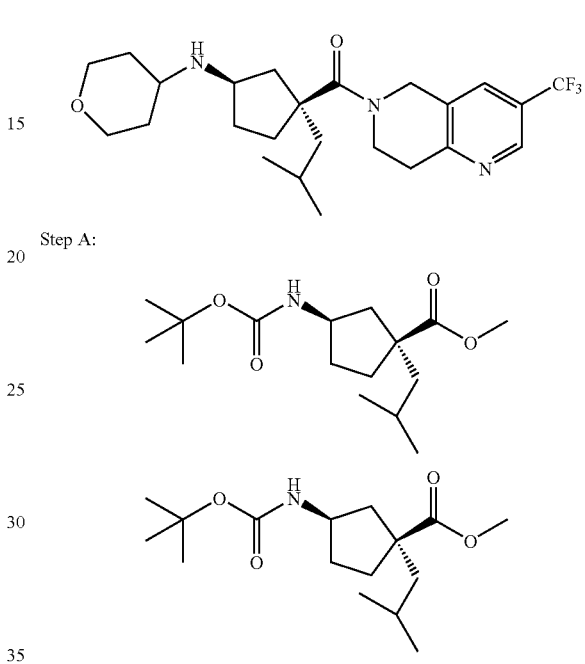

Step A:

A solution of the product described in Step B, Intermediate 11 (5.0 g, 15.2 mmol) in anhydrous tetrahydrofuran (20 mL) was added to a solution of freshly prepared lithium diisopropylamide (19.52 mmol in 35 mL of tetrahydrofuran) at −78° C. and the resulting dark-brown mixture was stirred for 45 min. A solution of 1-iodo-2-methylpropane (2.25 mL) was then added and the resulting mixture was stirred at −78° C. for 3 h. The mixture was the stirred at −25° C. for 1 h (yellow solution) and quenched with saturated aqueous ammonium chloride. The mixture was extracted with ethyl acetate (×3) and the combined organic layers were washed with brine, dried (MgSO₄) and concentrated in vacuo. The resulting oil was dissolved in tetrahydrofuran (30 mL) and treated with 10 mL of 2 N HCl and stirred for 3 h. The aqueous tetrahydrofuran was evaporated to afford a clear brown oil which was dissolved in dichloromethane (60 mL) and treated with a saturated solution of sodium bicarbonate (60 mL) and di-tert-butyl dicarbonate (17.7 g, 81.3 mmol). The mixture was stirred overnight and the layers were separated. The organic layer was washed with brine, dried (MgSO₄) and concentrated in vacuo. Flash chromatography eluting with ethyl acetate/hexanes (0 to 8%) afforded 0.78 g of the cis diastereomer and 1.69 g of the trans (with some cis) diastereomers (51%). ¹H NMR (CDCL₃, 500 MHz) □4.88–4.96(b, 1H), 4.06–4.16 (b, 1H), 3.71 (s, 3H), 2.21 (m, 1H), 2.14 (d, 1H), 2.15 (d, 1H), 2.06 (m, 1H), 1.85–1.92 (m, 1H), 1.72–1.79 (m, 1H), 1.58 (s, 2H), 1.48–1.54 (m, 1H), 1.45 (s, 9H), 0.82–0.87 (dd, 6H).

Step B

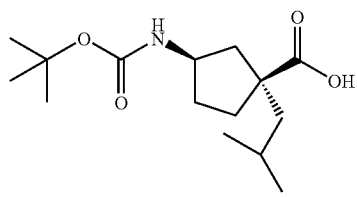

To a solution of 0.45 g (1.5 mmol) of the cis intermediate from Step A in tetrahydrofuran/methanol (5.0 mL) was added an aqueous solution of lithium hydroxide (0.10 g in 2.0 mL water). The mixture was stirred overnight at 60° C. and cooled to room temperature. The pH was adjusted to 7 and the methanol evaporated. The resulting suspension was extracted with ethyl acetate (×3). The combined organic layers were washed with brine, dried (MgSO$_4$) and concentrated in vacuo to afford 0.27 g (57%) of the title product as an oil.

Step C:

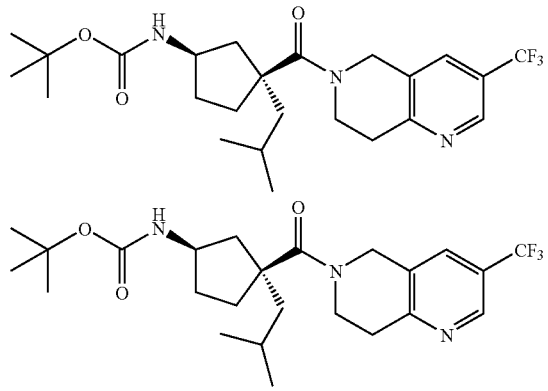

The acid from Step B (0.25 g, 0.89 mmol) in dry dichloromethane (4.0 mL) at room temperature was treated with Intermediate 19 (0.49 g, 1.8 mmol) and 1-hydroxy-7-azabenzotriazole (0.12 g, 0.89 mmol). After 10 min of stirring, 1-(-3-dimethylaminopropyl)-3-ethylcarbodiimide hydrochloride (0.51 g, 2.7 mmol) was added to the mixture and the reaction was quenched with sodium bicarbonate after 18 h. The suspension was extracted with dichloromethane (×2) and the combined organic layers were dried (MgSO$_4$) and concentrated in vacuo. Flash chromatograph eluting with ethyl acetate/hexanes (15%) afforded 0.220 g (52%) of the title product. LC-MS for $C_{24}H_{34}F_3N_3O_3$ calculated: 469.26, found 370.3 (loss of Boc group) [M+H–100]$^+$.

Step D

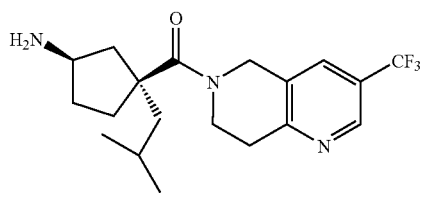

To a solution of the intermediate from Step C (0.220 g) in ethyl acetate (1.0 mL) was added a saturated solution of HCl in ethyl acetate and the mixture was stirred for 30 min. Removal of the volatiles in vacuo gave the desired product as the HCl salt. LC-MS for $C_{19}H_{26}F_3N_3O$ calculated: 369.20, found: 370.2 [M+H]$^+$.

Step E

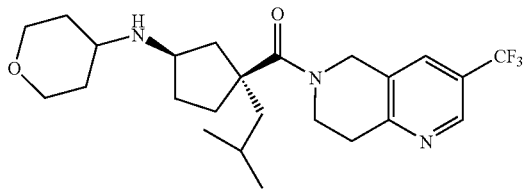

A solution of the intermediate from Step D (0.190 g, 0.468 mmol) in dichloromethane (3.0 mL) and diisopropylethylamine (0.123 mL) was treated with tetrahydro-4H-pyran-4-one (0.065 mL, 0.70 mmol) and 4 Å molecular sieve. After stirring the mixture for 45 min, sodium triacetoxyborohydride (0.198 g, 0.936 mmol) was added. The mixture was stirred for 18 h, filtered and the filtrate was extracted with water. The organic layer was dried (MgSO$_4$) and concentrated in vacuo. Reverse phase HPLC purification of the crude afforded the title product which was subsequently transformed to the HCl salt (0.072 g). LC-MS for $C_{24}H_{34}F_3N_3O_2$ calculated: 453.26, found 454.25 [M+H]$^+$.

EXAMPLE 66

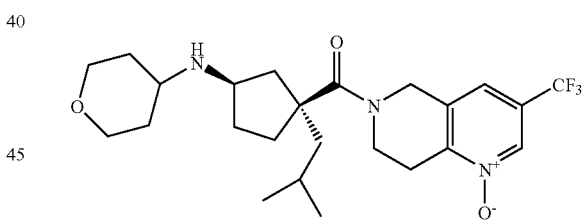

Step A:

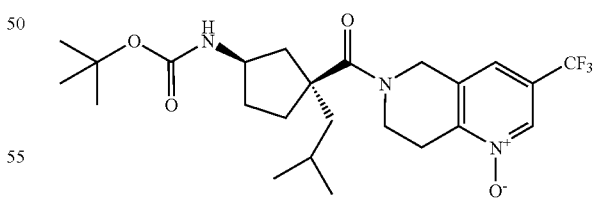

A solution of the intermediate in Step C, Example 65 (0.10 g, 0.23 mmol) in chloroform (20 mL) was treated with 3-chloroperoxybenzoic acid (0.198 g, 1.15 mmol) and the mixture was stirred for 16 h. The solvent was evaporated and flash chromatography eluting with ethyl acetate/hexanes (75%) afford 0.060 g of the N-oxide title compound (54%). LC-MS for $C_{24}H_{34}F_3N_3O_4$ calculated: 485.25, found 386.3 (loss of Boc group) [M+H–100]$^+$.

Step B

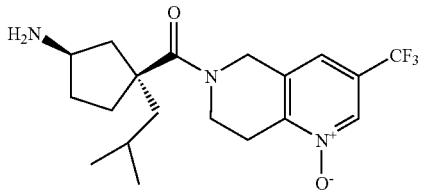

To a solution of the intermediate from Step A in ethyl acetate (1.0 mL) was added a saturated solution of HCl/ethyl acetate. The resulting solution was stirred for 30 min. Removal of the volatiles under vacuum gave the desired product as the HCl salt. LC-MS for $C_{19}H_{26}F_3N_3O_2$ calculated: 385.20, found 386.3 [M+H]$^+$.

Step C

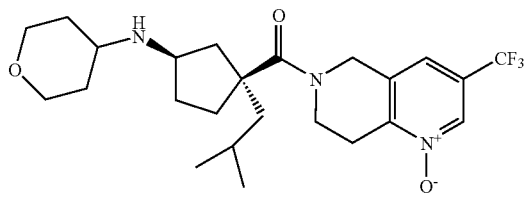

A solution of the intermediate from Step B (0.053 g, 0.13 mmol) in dichloromethane (2.0 mL) and diisopropylethylamine (0.033 mL) was treated with tetrahydro-4H-pyran-4-one (0.017 mL, 0.19 mmol) and 4 Å molecular sieve. After stirring the mixture for 45 min, sodium triacetoxyborohydride (0.053 g, 0.25 mmol) was added. The mixture was stirred for 18 h, filtered and the filtrate was extracted with water. The organic layer was dried (MgSO$_4$) and concentrated in vacuo. Reverse phase HPLC purification of the crude afforded gave the title product, which was subsequently transformed to the HCl salt (0.029 g). LC-MS for $C_{24}H_{34}F_3N_3O_3$ calculated: 469.26, found: 470.2 [M+H]$^+$.

EXAMPLE 67

Step A:

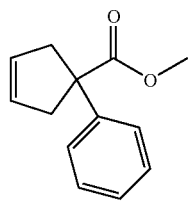

A solution of methyl phenylacetate (15 g, 99 mmol) in tetrahydrofuran (200 mL) and N,N'-dimethylpropyleneurea (50 ml) at 0° C. was treated with sodium hydride (7.99 g, 199 mmol) and the mixture stirred for 2 h at 50° C. (hydrogen gas evolution). After cooling to room temperature cis-1,4-dichloro-2-butene was added to the mixture (exothermic reaction) and the mixture was stirred at 50° C. for 3 h. The mixture was cooled to room temperature, quenched with saturated ammonium chloride and extracted with ethyl acetate (×2). The combined organic layers were washed with brine, dried (MgSO$_4$) and concentrated. Flash chromatography eluting with 3% ethyl acetate in hexanes afforded 7 g of the title product. $^1$H NMR (CDCl$_3$, 500 MHz) d7.35 (m, 5H), 5.78 (s, 2H), 3.65 (s, 3H), 3.42 (d, 2H), 2.78 (d, 2H).

Step B

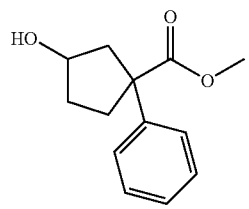

A solution of the intermediate from Step A (2.0 g, 9.9 mmol) in tetrahydrofuran (5 mL) at 0° C. was treated with 4.94 mL of 1.0 M borane-tetrahydrofuran complex. The mixture was stirred at room temperature overnight and quenched with 5 mL of water. Borax (2.28 g, 14.8 mmol) was added to the mixture and after 18 h the mixture was diluted with water and extracted with ethyl acetate (×2). The organic layer was dried (MgSO$_4$) and concentrated. Flash chromatography eluting with ethyl acetate/hexanes (15%) in hexanes afforded 1.2 g of a cis/trans mixture of the title alcohol.

Step C

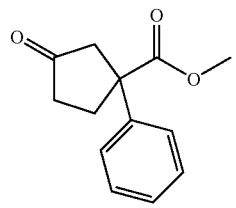

A solution of the intermediate in Step B (1.2 g, 5.4 mmol) in acetone (5.0 mL) was treated with 2 mL of Jones' reagent (10.3 g CrO$_3$ in 35 mL water and 8.8 mL of H$_2$SO$_4$) and the mixture was stirred for 2 h. The acetone was evaporated and the residue diluted with ethyl acetate and extracted with water (×3). The organic layer was washed with brine, dried (MgSO$_4$) and concentrated in vacuo. Column chromatography eluting with ethyl acetate/hexanes (10–20%) afforded 0.34 g of the title ketone. $^1$H NMR (CDCl$_3$, 500 MHz) 7.35 (m, 5H), 3.68 (s, 3H), 3.27 (d, 2H), 3.0 (m, 2H), 2.65 (d, 2H).

Step D:

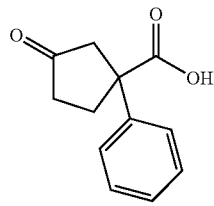

To a solution of the intermediate from Step C (0.19 g, 0.87 mmol) in tetrahydrofuran/methanol (5.0 mL) was added an aqueous solution of lithium hydroxide (0.074 g in 2.0 mL water). The mixture was stirred for 6 h at 60° C. and cooled to room temperature. The pH was adjusted to 7 and the methanol evaporated. The resulting suspension was extracted with ethyl acetate (×3). The combined organic layers were washed with brine, dried (MgSO$_4$) and concentrated in vacuo to afford 0.145 g (82%) of the title product as an oil. $^1$H NMR (CDCl$_3$, 500 MHz) d7.38 (m, 5H), 3.28 (d, 2H), 3.05 (m, 2H), 2.63 (d, 2H).

Step E

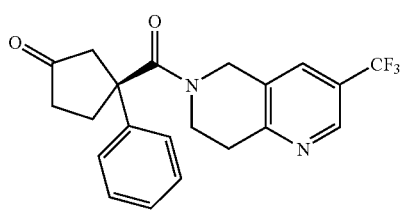

The acid from Step D (0.14 g, 0.71 mmol) in dry dichloromethane (3.0 mL) at room temperature was treated with Intermediate 8 (0.39 g, 1.4 mmol) and 1-hydroxy-7-azabenzotriazole (0.096 g, 0.71 mmol). After 10 min of stirring, 1-(-3-dimethylaminopropyl)-3-ethylcarbodiimide hydrochloride (0.4 g, 2 mmol) was added to the mixture and the reaction was quenched with sodium bicarbonate after 18 h. The suspension was extracted with dichloromethane (×2) and the combine organic layers dried (MgSO$_4$) and concentrated in vacuo. Flash chromatograph eluting with ethyl acetate/hexanes (25–30%) afforded 0.212 g (77%) of the title product. LC-MS for C$_{21}$H$_{19}$F$_3$N$_2$O$_2$ [M+H]$^+$ calculated 389.14, found 389.05.

Step F:

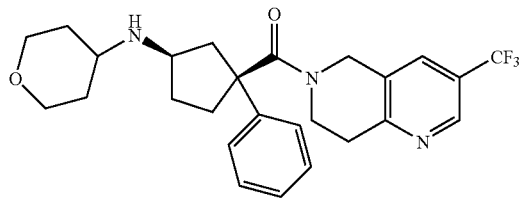

-continued

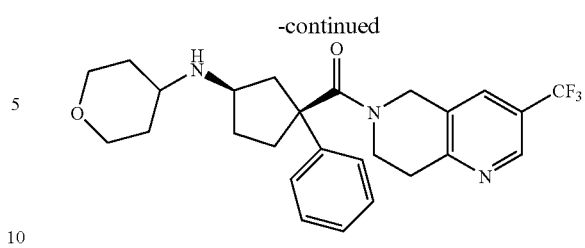

A solution of the intermediate from Step E (0.2 g, 0.5 mmol) in dichloromethane (4.0 mL) was treated with tetrahydro-2H-pyran-4-ylamine (0. 105 g, 0.76 mmol) and 4 Å molecular sieve. After stirring the mixture for 45 min, sodium triacetoxyborohydride (0.216 g, 1.02 mmol) was added. The mixture was stirred for 18 h, filtered and the filtrate was extracted with water. The organic layer was dried (MgSO$_4$) and concentrated in vacuo. Column chromatography eluting with methanol/ethyl acetate (3%) afforded 0.082 g of the two cis products and 0.020 g of the two trans title products which were subsequently transformed to their HCl salts. LC-MS for C$_{26}$H$_{30}$F$_3$N$_3$O$_2$ calculated 473.23, found 474.25 [M+H]$^+$.

EXAMPLE 68

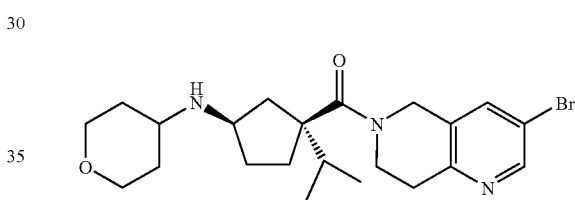

Step A:

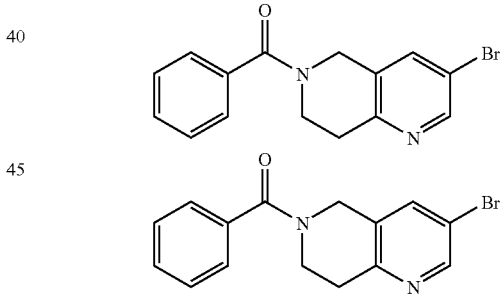

To a solution of the product described in Intermediate 28, Step C (1.44 g, 5.68 mmol) in 48% HBr (12 mL), was added copper(I) bromide (1.01 g, 7.04 mmol), and saturated sodium nitrite (520 mg, 7.55 mmol) solution. The reaction mixture was stirred at room temperature for 1 h and heated at 100° C. for 20 min. The reaction mixture was made alkaline by the addition of 50% KOH solution, and then extracted with ethyl acetate (four times). The organic portions were combined, washed by water and brine, dried over Na$_2$SO$_4$, filtered and concentrated. The residue was purified by column chromatography (silica gel, 50% ethyl acetate/hexanes to 75% ethyl acetate/hexanes) to yield the title compound (Example 52, Step A, 0.79 g, 52%). ESI-MS calculated For C$_{15}$H$_{13}$BrN$_2$O: 316.02; Found: [M+H] 317.

Step B

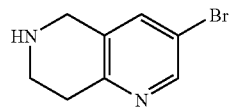

A solution of the amide intermediate from Example 68, Step A (0.79 g) in concentrated HCl (50 mL) was refluxed for 24 h. The solvent and extra HCl were evaporated under vacuum. The residue was then suspended with $Ca(OH)_2$ (1.20 g) in dichloromethane (100 mL) and stirred at room temperature for 12 h. The solid precipitate was filtered and the filtrate was concentrated to give the title compound (Example 55, Step B, 274 mg, 53%). $^1$H-NMR (500 MHz, $CD_3OD$) δ 8.46 (s, 1H), 7.48 (s, 1H), 4.00 (s, 2H), 3.23 (t, J=6.0 Hz, 2H), 2.80 (t, J=6.0 Hz, 2H).

Step C

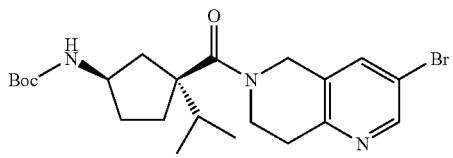

To a flask was added Intermediate 11 (274 mg, 1.01 mmol), the product described in Step B, Example 68 (215 mg, 1.01 mmol), bromo-tris-pyrrolidino-phosphonium hexafluorophosphate (471 mg, 1.01 mmol), 4-dimethylaminopyridine (74 mg, 0.61 mmol), diisopropylethylamine (528 μL, 3.03 mmol) and dichloromethane (5 mL). The resulting mixture was stirred for 36 h under nitrogen, diluted by dichloromethane, washed by water (adding 1 mL of 1N HCl) and brine, dried over $Na_2SO_4$, filtered and concentrated. The residue was purified by flash column chromatography (silica gel, 50% ethyl acetate/hexanes to 80% ethyl acetate/hexanes) to yield the title compound (Example 55, Step C) (358 mg, 93%). $^1$H-NMR (400 MHz, $CDCl_3$) δ 8.52 (s, 1H), 7.61 (s, 1H), 4.67–4.85 (m, 3H), 3.82–4.00 (m, 3H), 3.00 (m, 2H), 1.60–2.20 (m, 7H), 1.44 (s, 9H), 0.89 (m, 6H). ESI-MS calculated For $C_{22}H_{32}BrN_3O_3$: 465.16; Found: [M+H and M+H+2]$^+$ 466 and 468 respectively.

Step D

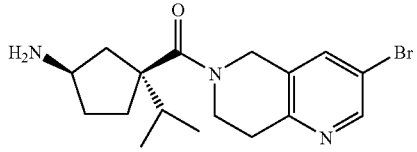

A solution of the Boc amide intermediate from Example 68, Step C (350 mg, 0.75 mmol) in 4.0 N HCl/dioxane (4.0 mL, 16 mmol) was stirred for 12 h. Solvent was evaporated to yield the product as an HCl salt (342 mg, 100%).

$^1$H-NMR (500 MHz, $CD_3OD$) δ 8.50 (s, 1H), 7.60 (s, 1H), 4.72–4.78 (m, 2H), 3.86–3.92 (m, 2H), 3.75 (s, 3H), 3.29 (m, 1H), 3.00 (m, 2H), 2.50 (m, 1H), 2.02–2.14 (m, 2H), 1.78–1.92 (m, 2H), 1.62–1.69 (m, 1H), 1.28–1.35 (m, 1H), 0.88 (m, 6H). ESI-MS calculated For $C_{17}H_{24}BrN_3O_3$: 365.11; Found: [M+H]$^+$ 366.

Step E:

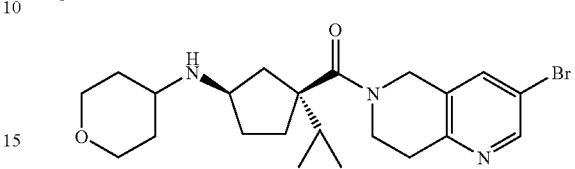

A solution of the product described in Step D, Example 68 (55 mg, 0.13 mmol), tetrahydro-4H-pyran-4-one (35 mg, 0.38 mmol), diisopropylethylamine (44 μL, 0.25 mmol) and crushed molecular sieves (4 Å, 150 mg) in dichloromethane (4 mL) was treated with sodium triacetoxyborohydride (132 mg, 0.625 mmol) and stirred at room temperature overnight. The reaction was quenched with saturated sodium bicarbonate solution (10 mL) and diluted with an additional 15 mL of dichloromethane. The organic layer was separated and the aqueous layer was washed with dichloromethane (2×10 mL). The organics were combined, dried over anhydrous sodium sulfate, filtered and evaporated under reduced pressure. The residue was purified on preparative TLC (1000 micron) (eluent: 1.0% $NH_4OH$/10% methanol/89% $CH_2Cl_2$) to yield the final product of the title compound as a free base. Its HCl salt (47.9 mg) was formed by treatment with 4 N HCl/dioxane. $^1$H NMR ($CDCl_3$, 500 MHz): d 8.50 (s, 11H), 7.60 (s, 1H), 4.68–4.78 (m, 2H), 3.97 (m, 2H), 3.88 (m, 2H), 3.38–3.48 (m, 2H), 3.18 (m, 1H), 2.98 (m, 2H), 2.75 (m, 1H), 2.52 (m, 1H), 2.15 (m, 1H), 2.04 (br s, 1H), 1.74–1.93 (m, 4H), 1.24–1.60 (m, 5H), 0.88 (m, 6H). LC-MS calculated for $C_{22}H_{32}BrN_3O_2$: 449.17; Found: [M+H and M+H+2]$^+$ 450 and 452 respectively.

EXAMPLE 69

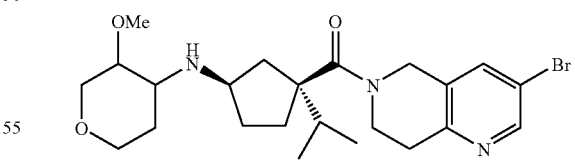

This product was prepared in an analogous fashion to that of Example 68, except tetrahydro-4H-pyran-4-one was replaced with Intermediate 3. $^1$H NMR ($CDCl_3$, 500 MHz): d 8.51 (s, 1H), 7.60 (s, 1H), 4.66–4.80 (m, 2H), 4.11 (m, 1H), 3.86–3.98 (m, 3H), 3.41 (s, 3H), 3.34 (m, 2H), 3.16 (m, 1H, 2.99 (m, 2H), 2.84 (br s, 1H), 2.58 (m, 1H), 1.56–2.14 (m, 7H), 1.34 (m, 1H), 0.88 (m, 6H). LC-MS calculated for $C_{23}H_{34}BrN_3O_3$: 479.18; Found: 480 and 482 (M+H and M+H+2).

EXAMPLE 70

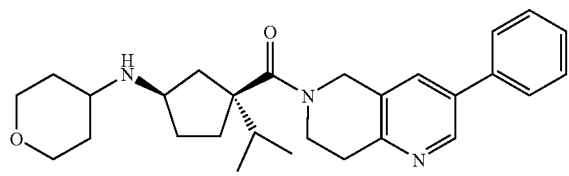

Step A:

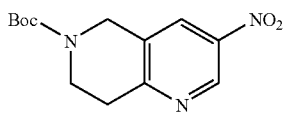

A solution of 3,5-dinitro-1-methyl-2-pyridone (5.40 g, 27.1 mmol) and tert-butyl 4-oxo-1-piperidinecarboxylate (6.48 g, 32.5 mmol) in 2 M $NH_3$/methanol (100 mL) was stirred at 60° C. for 16 h. The solvent was evaporated under vacuum and the residue was purified by flash column chromatography (silica gel, 30% ethyl acetate/hexanes to 50% ethyl acetate/hexanes) to yield the title compound (6.22 g, 82%). $^1$H-NMR (500 MHz, $CDCl_3$) δ 9.26 (d, J=2.5 Hz, 1H), 8.24 (d, J=2.5 Hz, 1H), 4.72 (s, 2H), 3.81 (t, J=6.0 Hz, 2H), 3.14 (t, J=6.0 Hz, 2H), 1.52 (s, 9H). LC-MS calculated For $C_{13}H_{17}N_3O_4$: 279.12; Found: $[M+H]^+$ 280.

Step B

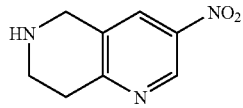

A solution of the intermediate described in Example 70, Step A (6.15 g, 22.02 mmol) in 4 N HCl/dioxane (110 mL, 440 mmol) was stirred for 12 h. Solvent was evaporated to yield the compound as the HCl salt (5.47 g, 99%). $^1$H-NMR (400 MHz, $CD_3OD$) δ 9.32 (d, J=2.5 Hz, 1H), 8.59 (d, J=2.5 Hz, 1H), 4.57 (s, 2H), 3.71 (t, J=6.0 Hz, 2H), 3.38 (t, J=6.0 Hz, 2H).

Step C:

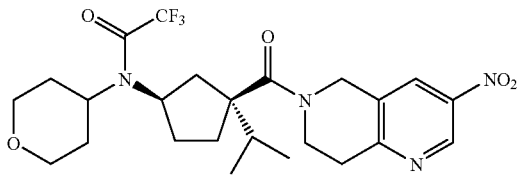

To a solution of Intermediate 9 (8.39 g, 23.9 mmol) in dichloromethane (80 mL), was added 2 M oxalyl chloride in dichloromethane (17.36 mL, 34.72 mmol) and N,N-dimethylformamide (~100 μL). The reaction mixture was stirred for 3 h, and concentrated. The residue was put on high vacuum for 2 h and dissolved in dichloromethane (40 mL). The formed acid chloride was added into a solution of the product described above (Example 70, Step B, 5.47 g, 21.70 mmol) and diisopropylethylamine (13.61 mL, 78.12 mmol) in dichloromethane (40 mL) at 0° C. The reaction mixture was stirred for 16 h and diluted with dichloromethane, washed with 10% $NaHCO_3$ and brine, dried over $Na_2SO_4$, filtered and concentrated. The residue was purified by flash column chromatography (silica gel, 80% ethyl acetate/hexane to 100% ethyl acetate) to yield the title compound (7.25 g, 65.3%). LC-MS calculated For $C_{24}H_{31}F_3N_4O_5$: 512.22; Found: $[M+H]^+$ 513.

Step D:

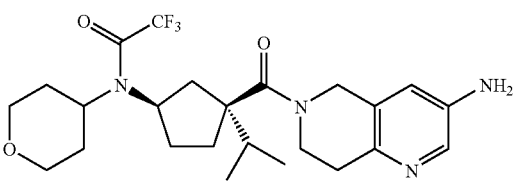

To a solution of intermediate described in Example 70, Step C (7.22 g, 14.1 mmol) in ethanol (150 mL) was added 10% Pd/C (750 mg). The reaction mixture was placed in a Parr apparatus and shaken under 50 lb pressure of $H_2$ for 2 h. The solution was filtered through celite and concentrated under vacuum to yield the desired product (6.97 g, 100%). LC-MS calculated For $C_{24}H_{33}F_3N_4O_3$: 482.25; Found: $[M+H]^+$ 483.

Step E:

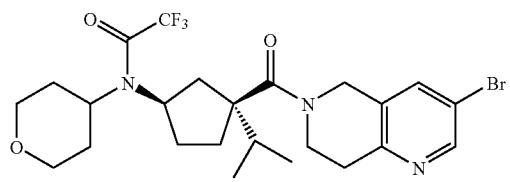

This compound was prepared starting from the intermediate described in Example 70, Step D as detailed in Example 52, Step A. LC-MS calculated For $C_{24}H_{31}BrF_3N_3O_3$: 545.15; Found: $[M+H]^+$ 546.

Step F:

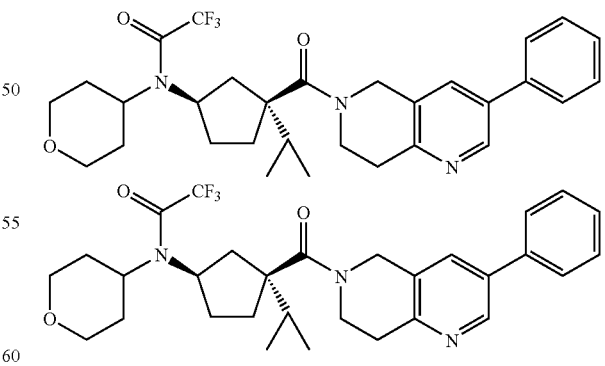

To a mixture the product described in Example 70, Step E (150 mg, 0.275 mmol), palladium (II) acetate (1 mg), phenylboronic acid (36.8 mg, 0.302 mmol), $K_2CO_3$ (190 mg, 1.38 mmol) and tetrabutylammonium bromide (88.7 mg, 0.275 mmol) was added slowly water (1 mL) under nitrogen. The reaction mixture was stirred and heated at 70°

C. for 10 h, diluted with water (5 mL) and extracted with ethyl acetate (five times). The organic portions were combined, washed by brine, dried over Na$_2$SO$_4$, filtered and concentrated. The residue was purified by preparative TLC (silica gel, 1000 micron) (developed by 80% ethyl acetate/hexanes) to yield the product (124 mg, 83%). $^1$H-NMR (500 MHz, CDCl$_3$) δ 8.68 (m, 1H), 7.42–7.66 (m, 6H), 4.75–4.98 (m, 2H), 3.88–4.20 (m, 6H), 3.22–3.62 (m, 2H), 3.10 (s, 2H), 2.74–2.86(m, 2H), 2.44 (m, 1H), 1.80–2.21 (m, 4H), 1.53–1.74(m, 3H), 0.94(m, 6H). LC-MS calculated For C$_{30}$H$_{36}$F$_3$N$_3$O$_3$: 543.27; Found: [M+H]$^+$ 544.

Step G:

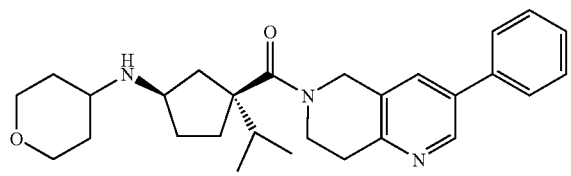

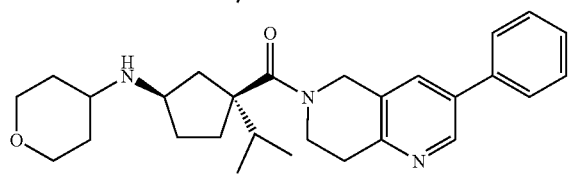

To a solution of the product described in Example 70, Step F (120 mg, 0.221 mmol) in ethanol (10 mL) was added sodium borohydride (168 mg, 4.42 mmol). The reaction mixture was stirred for 16 h, and diluted with methanol. The extra sodium borohydride was destroyed by 4 N HCl in dioxane and then the solvent was evaporated under vacuum. The residue was purified by preparative TLC (silica gel, 1000 micron) (developed by 10% [aqueous NH$_4$OH/methanol 1/9]/dichloromethane) to yield the final product of the title compound as a free base. Its HCl salt (49.0 mg) was formed by treatment with 4 N HCl/dioxane. $^1$H NMR (400 MHz, CDCl$_3$): d 8.67 (s, 1H), 7.40–7.62 (m, 6H), 4.83 (s, 2H), 3.94–4.02 (m, 4H), 3.33–3.44 (m, 3H), 2.96–3.12 (m, 3H), 2.56 (m, 1H), 1.84–2.18 (m, 6H), 1.55–1.70 (m, 4H), 1.26 (s, 1H), 0.86–0.93 (m, 6H). LC-MS calculated for C$_{28}$H$_{37}$N$_3$O$_2$: 447.29; Found: [M+H]$^+$ 488

TABLE 3

The table below shows other examples synthesized in a similar fashion to Example 70. The difference is the replacement of the phenyl substituent with various substituted aryl groups.

| Example | substituent | Molecular Formula | Calculated [M] | Found [M+H]$^+$ |
|---|---|---|---|---|
| 71 | 4-methylphenyl | C$_{29}$H$_{39}$N$_3$O$_2$ | 461.30 | 462.3 |
| 72 | 4-fluorophenyl | C$_{28}$H$_{36}$N$_3$O$_2$F | 465.27 | 466.3 |
| 73 | 4-methoxyphenyl | C$_{29}$H$_{39}$N$_3$O$_3$ | 477.30 | 478.3 |
| 74 | 4-CF$_3$-phenyl | C$_{29}$H$_{36}$N$_3$O$_2$F$_3$ | 515.24 | 516.3 |
| 75 | 2-CF$_3$-phenyl | C$_{29}$H$_{36}$N$_3$O$_2$F$_3$ | 515.24 | 516.3 |
| 76 | 3,5-difluorophenyl | C$_{28}$H$_{35}$N$_3$O$_2$F$_2$ | 483.26 | 484.3 |
| 77 | 2,4-difluorophenyl | C$_{28}$H$_{35}$N$_3$O$_2$F$_2$ | 483.26 | 484.3 |
| 78 | 3,4-difluorophenyl | C$_{28}$H$_{35}$N$_3$O$_2$F$_2$ | 483.26 | 484.3 |
| 79 | 4-pyridyl | C$_{27}$H$_{36}$N$_4$O$_2$ | 448.27 | 449.3 |
| 80 | 3-pyridyl | C$_{27}$H$_{36}$N$_4$O$_2$ | 448.27 | 449.3 |
| 81 | 2-pyridyl | C$_{27}$H$_{36}$N$_4$O$_2$ | 448.27 | 449.3 |
| 82 | 6-methoxy-3-pyridyl | C$_{28}$H$_{38}$N$_4$O$_3$ | 478.28 | 479.3 |

EXAMPLE 83

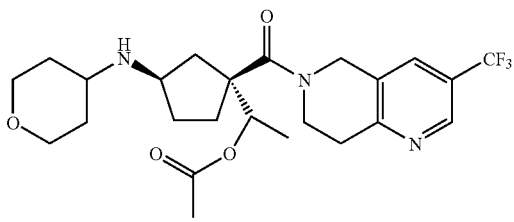

A solution of the lower eluting isomer described in Example 55 (40 mg, 0.091 mmol), acetic acid (210 μL, 3.62 mmol) in tetrahydrofuran (6 mL) was added to a solution containing nBu$_3$P (900 μL, 3.62 mmol) and diethyl azodicarboxylate (570 μL, 3.62 mmol) in tetrahydrofuran (6 mL) at 0° C., and stirring was continued at room temperature for 6 h. The reaction mixture was diluted with dichloromethane, washed with sodium bicarbonate, dried with anhydrous sodium sulfate and the solvent was removed in vacuo. Preparative TLC purification (dichloromethane/methanol/ammonium hydroxide: 90:9:1) gave 13.5 mg (31%) of the desired product. LC MS: for $C_{24}H_{32}N_3F_3O_4$ calculated 483.23, found 484.30 $[M+H]^+$.

EXAMPLE 84

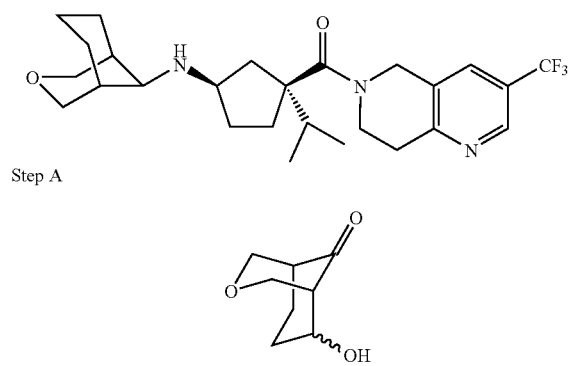

Step A

A mixture of 9.70 g (97.0 mmol) of tetrahydro-4 H-pyran-4-one and 10.5 g (150 mmol) of pyrrolidine was stirred at room temperature for 1.5 h. The excess pyrrolidine was removed under vacuum. The residue was dissolved in 90 mL of diethyl ether, cooled to 0° C. and 7.4 mL of acrolein was added. The resulting mixture was stirred at room temperature overnight. 67 mL of water was added, followed by a solution of 14 g of sulfuric acid (98%) in 33 mL of water. The ether and 10 mL of water were removed under reduced pressure, the remaining mixture was refluxed for 0.3 h and then cooled to room temperature. The resulting dark mixture was extracted with dichloromethane (4×100 mL), dried over anhydrous Na$_2$SO$_4$ and evaporated. The residue was purified by MPLC (30% ethyl acetate/hexanes). A mixture (6.6 g) of endo/exo isomers (~1/1) was obtained together with pure fast isomer (1.0 g, endo) and pure slow isomer (0.8 g, exo). $^1$H NMR (400 MHz, CDCl$_3$): δ endo: 4.58 (d, J=11.6 Hz, 1H), 4.20 (d, J=11.2 Hz, 1H), 4.17 (d, J=11.2 Hz, 1H), 3.91 (d, J=11.3 Hz, 1H), 3.72 (d, J=11.5 Hz, 1H), 2.60–2.30 (m, 4H), 2.13 (m, 1H), 2.02 (m, 1H), 1.80 (m, 1H). Exo: 4.54 (d, J=1.1 Hz, 1H), 4.10 (dd, J=11.4 Hz, 2H), 3.80 (dd, J=11.5 Hz, 2H), 2.86 (s, 1H), 2.70 (m, 1H), 2.50 (s, 1H), 2.38 (m, 2H), 2.10 (m, 1H), 1.78 (m, 1H).

Step B:

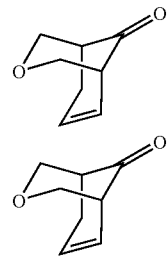

To a mixture of the hydroxyketone from Step A, Example 84 (endo/exo: ~1:1, 3.12 g, 20 mmol), 1,8-diazabicyclo[5.4.0]undec-7-ene (9.0 g, 60 mmol) in benzene (25 mL) at 0° C. was added dropwise a neat solution of trifluoromethanesulfonic anhydride. An exothermic reaction was observed. The reaction mixture was stirred for 1 h, poured directly onto a silica gel column, eluting with 20% Et$_2$O/hexanes. The desired product was obtained as a light yellow oil (1.80 g). $^1$H NMR (400 MHz, CDCl$_3$): δ 5.98 (m, 1H), 5.65 (m, 1H), 4.10 (dd, 1H), 3.90(dd, 1H), 3.78 (dd, 1H), 3.65 (dd, 1H), 2.80 (m, 3H), 2.50 (d, J=11.5).

Step C:

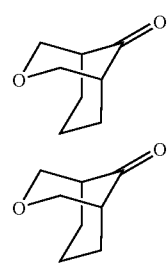

A mixture of the unsaturated ketone from Step B, Example 84 (9.0 g) and 10% Pd/C (0.9 g) in 50 mL of ethyl acetate was hydrogenated on a Parr apparatus for 2 h under 50 lb of hydrogen. The catalyst was removed by filtration. The filtrate was evaporated. The product was obtained as a light yellow solid (6.817 g). $^1$H NMR (400 MHz, CDCl$_3$): δ 4.24 (d, J=11.5 Hz, 2H), 3.90 (d, J=11.60 Hz, 2H), 2.58 (m, 1H), 2.38 (br S, 2H), 2.25 (m, 2H), 2.08 (m, 2H), 1.58 (m, 1H).

Step D:

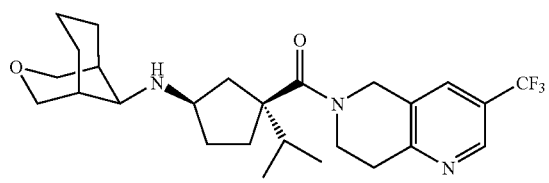

Intermediate 19 (117 mg, 0.300 mmol), the bicyclic ketone from Step C, Example 84 (84 mg, 0.6 mmol), diisopropylethylamine (78 mg, 0.60 mmol), molecular sieves (4 Å, 200 mg) and sodium triacetoxyborohydride (125 mg, 0.600 mmol) were mixed with 10 mL of dichloromethane. The mixture was stirred for 5 h, LC-MS showed a complete conversion. The reaction was quenched with saturated aqueous sodium carbonate, filtered to remove insoluble molecular sieves. The organic phase was separated and dried over sodium sulfate. The crude product was purified on preparative TLC (10%[aqueous NH$_4$OH/methanol 1/9]/dichloromethane) to yield the title compound as a white solid (70 mg, 44%). ESI-MS calculated for C$_{26}$H$_{36}$F$_3$N$_3$O$_2$: 479; Found: 480 [M+H]$^+$. The endo and exo single isomers were obtained by using an HPLC equipped with a preparative ChiralCel OD column eluting with 10% ethanol and 90% hexanes with a flow rate of 9 mL/min.

EXAMPLE 85

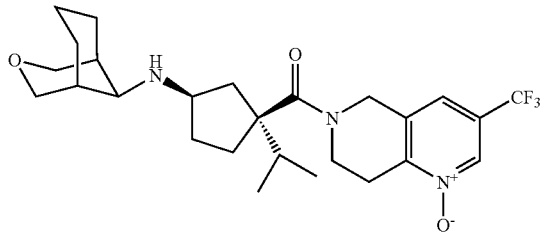

This compound was prepared starting from Intermediate 20 according to the procedure as detailed in Example 84. ESI-MS calculated for C$_{26}$H$_{36}$F$_3$N$_3$O$_3$: 495; Found: 496 [M+H]$^+$. The endo and exo single isomers were obtained by using an HPLC equipped with a preparative ChiralCel OD column eluting with 10% ethanol and 90% hexanes with a flow rate of 9 mL/min.

EXAMPLE 86

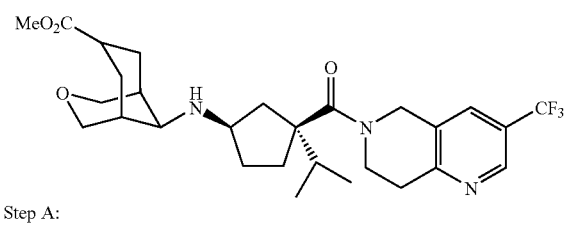

Step A:

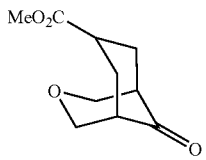

A mixture of tetrahydro-4H-pyran-4-one (10 g, 0.10 mol) and pyrrolidine (12 g, 0.15 mol) was stirred for 2 h. Excessive pyrrolidine was removed under vacuum. The enamine residue was dissolved in 50 mL of acetonitrile. To this solution was added a neat solution of methyl α-bromomethyl acrylate. The mixture was stirred for 2 h before water (30 mL) was added. After being stirred for additional 2 h, acetonitrile was removed under vacuum. The crude product was extracted into ethyl acetate (3×) and dried over sodium sulfate. Flash chromatography (50% ethyl acetate/ hexanes) afforded three components. The most polar component contained the desired product. Further purification on MPLC (30% ethyl acetate/hexanes) afforded the pure compound (3.4 g, 17%). $^1$H NMR (400 MHz, CDCl$_3$): δ 4.20, 4.18 (ss, 2H), 3.76 (s, 3H), 3.70 (s, 2H), 3.00, 2.98 (ss, 2H), 2.61 (m, 1H), 2.38 (m, 2H), 2.22 (m, 2H).

Step B:

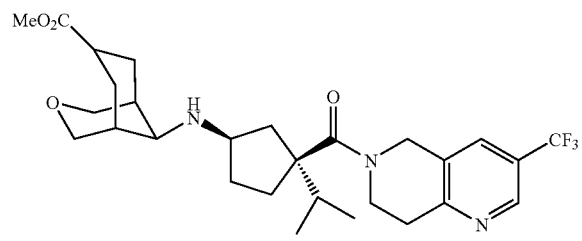

This compound was prepared starting from Intermediate 19 and the keto ester from Step A, Example 86 according to the procedure detailed in Example 84. ESI-MS calculated for C$_{28}$H$_{38}$F$_3$N$_3$O$_4$: 537; Found: 538 [M+H]$^+$. The endo and exo single isomers were obtained by using an HPLC equipped with a preparative ChiralCel OD column eluting with 10% ethanol and 90% hexanes with a flow rate of 9 mL/min.

EXAMPLE 87

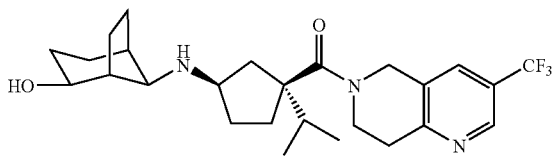

Step A:

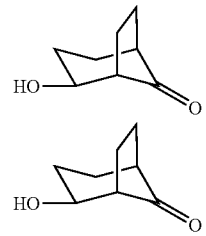

To a stirred solution of 1-morpholino-1-cyclopentene (15.3 g, 100 mmol) in ether (150 mL) at 0° C. was added acrolein neat solution (90%, 9 mL). The resulting mixture was stirred at room temperature overnight, mixed with water (70 mL) and a solution of concentrated sulfuric acid (15 mL) in 30 mL of water. The ether was removed and the aqueous solution was refluxed for 30 min. The dark solution was cooled to room temperature, extracted with dichloromethane (3×), dried over sodium sulfate. Flash chromatography (50% ethyl acetate/hexanes) afforded two components. Fast isomer (3.2 g): $^1$H NMR (400 MHz, CDCl$_3$): δ 4.05 (m, 1H), 2.44 (m, 1H), 2.24 (m, 1H), 2:10–1.60 (m, 9H). Slow isomer (3.0 g): $^1$H NMR (400 MHz, CDCl$_3$): δ 4.35 (m, 1H), 2.40–1.60 (m, 11H).

Step B:

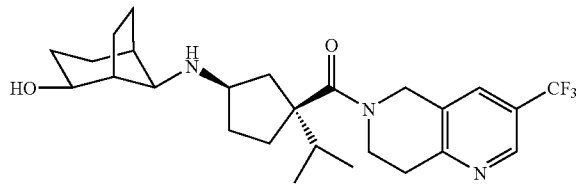

This compound as a mixture of all diastereoisomers was prepared starting from Intermediate 19 and the hydroxy ketone (fast or slow isomers, Step A, Example 87) according to the same procedure as detailed in Example 71. ESI-MS calculated for $C_{25}H_{36}F_3N_3O_2$: 479; Found: 480 [M+H]$^+$. The corresponding major single isomers from the fast and slow eluted hydroxy ketones were obtained by using an HPLC equipped with a preparative ChiralCel OD column eluting with 5% ethanol and 95% hexanes with a flow rate of 9 mL/min.

EXAMPLE 88

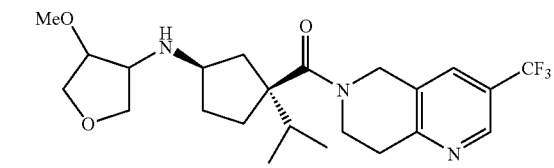

Step A

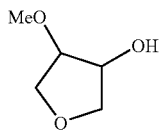

To a stirred solution of 3,4-anhydroerythritol (25 g, 240 mmol) in tetrahydrofuran (100 mL) was added lithium hydride (2.1 g, 260 mmol) at 0° C. The resulting suspension was stirred for 1 h before iodomethane (15.6 mL, 250 mmol) was added. The suspension was stirred for 2 days, then at 50° C. for 2 h. After being cooled to room temperature, the reaction was quenched with ice water, extracted with ethyl acetate (3×), dried over sodium sulfate and evaporated. The residue was purified by flash chromatogrpahy (10% methanol/dichloromethane) to yield the desired mono alcohol contaminated with over alkylated ether. Further flash chromatography (eluant:ethyl acetate) afforded the pure alcohol as a colorless oil (3.0 g, 11%). $^1$H NMR (400 MHz, CDCl$_3$): δ 4.29 (m, 1H), 3.90 (m, 3H), 3.78 (m, 2H), 3.42 (s, 3H), 2.60 (br s, 1H).

Step B:

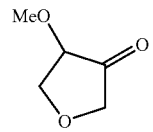

To a stirred solution of 2 M oxalyl chloride (12 mL, 24 mmol) was added dichloromethane (10 mL). The solution was cooled at −78° C. under nitrogen, dimethyl sulfoxide was added (2.83 mL, 40.0 mmol) dropwise, stirred for 10 min, then solution of the alcohol from Step A, Example 88 (2.36 g, 20 mmol) was added in dichloromethane (10 mL). The resulting mixture was stirred for 30 min before triethylamine (11.5 mL, 80 mmol) was added. After being warmed to room temperature, the mixture was diluted with ether. The resulting solid was removed by filtration and the filtrate was concentrated and the residue purified by flash chromatography (eluant: 1:1 ether/dichloromethane) to yield the desired ketone as a yellow oil (2.4 g, 100%). $^1$H NMR (400 MHz, CDCl$_3$): δ 4.40 (m, 1H), 4.00 (m, 1H), 3.90 (m, 1H), 3.58 (s, 3H).

Step C:

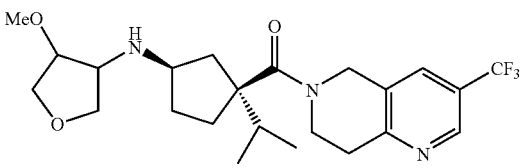

This compound was prepared starting from Intermediate 19 and the tetrahydrofuran ketone from Step B, Example 88 according to the procedure detailed in Example 71. LC-MS calculated for $C_{23}H_{32}F_3N_3O_3$: 455; Found: 456 [M+H]$^+$. The two major cis single isomers were obtained by using an HPLC equipped with a preparative ChiralCel OD column eluting with 10% ethanol and 90% hexanes with a flow rate of 9 mL/min.

EXAMPLE 89

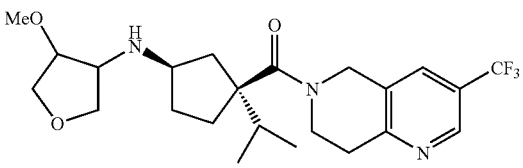

This compound was prepared starting from Intermediate 19 and commercially available 2-methyl tetrahydrofuran-3-one according to the procedure detailed in Example 84. LC-MS calculated for $C_{23}H_{32}F_3N_3O_2$: 439; Found: 440 [M+H]$^+$. The two major cis single isomers were obtained by using an HPLC equipped with a preparative ChiralCel OD column eluting with 5% ethanol and 95% hexanes with a flow rate of 9 mL/min.

EXAMPLE 90

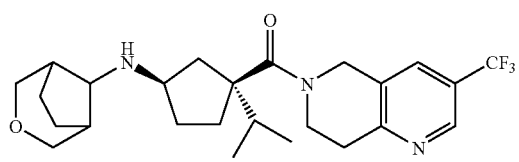

Intermediate 19 (76 mg, 0.18 mmol) was combined with Intermediate 26 (18 mg, 0.14 mmol), N,N-diisopropylethylamine (74 μL, 0.43 mmol), 4 Å powdered molecular sieves (100 mg), and sodium triacetoxyborohydride (150 mg, 0.710 mmol) in 5 mL of dichloromethane. The reaction mixture was stirred at room temperature for 3 days, then filtered through celite, washed with saturated sodium bicarbonate and brine, and dried over $Na_2SO_4$, filtered and concentrated under reduced pressure. The product was purified first by preparative TLC (silica gel, 0.5% $NH_4OH$/4.5% methanol/ 95% dichloromethane) to give a crude product of which 20% was purified by reverse phase HPLC (C 18, 20–100% MeCN/$H_2O$) and converted to its hydrochloride salt by the addition of hydrogen chloride (2 M solution in ethyl ether) to give 2.2 mg of a white solid (17%). ESI-MS calculated for $C_{25}H_{34}F_3N_3O_2$: 465.26; found 466 $[M+H]^+$.

EXAMPLE 91

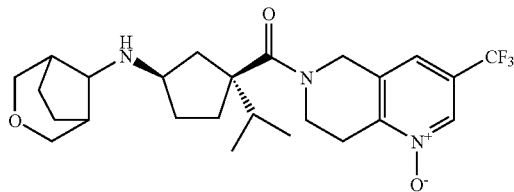

Intermediate 20 (129 mg, 0.32 mmol) was combined with Intermediate 26 (40 mg, 0.32 mmol), N,N-diisopropylethylamine (175 μL, 1.05 mmol), 4 Å powdered molecular sieves (100 mg), and sodium triacetoxyborohydride (268 mg, 1.27 mmol) in 5 mL dichloromethane. The reaction mixture was stirred at room temperature for 1.5 h and then was placed in the refrigerator overnight before being filtered through celite, washed with saturated sodium bicarbonate and brine, and dried over $Na_2SO_4$, filtered and concentrated under reduced pressure. The product was purified by preparative TLC (silica gel, 0.5% $NH_4OH$/4.5% methanol/95% dichloromethane) and converted to its hydrochloride salt by the addition of hydrogen chloride (2 M solution in ethyl ether) to give 75 mg of a white solid (48%). ESI-MS calculated for $C_{25}H_{34}F_3N_3O_3$: 481.26; found 482 $[M+H]^+$.

EXAMPLE 92

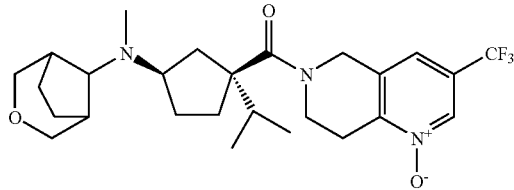

The product from Example 91 (11 mg, 0.021 mmol) was combined with formalin (37% aqueous solution, 17 μL, 0.21 mmol), N,N-diisopropylethylamine (8 μL, 0.05 mmol) and 4 Å powdered molecular sieves (20 mg) in 5 mL of dichloromethane. The mixture was stirred at room temperature for 30 min before sodium triacetoxyborohydride (22 mg, 0.10 mmol) was added. The reaction was stirred at room temperature for 1 h before being filtered through celite, washed with saturated sodium bicarbonate and brine, and dried over $Na_2SO_4$, filtered and concentrated under reduced pressure. The product was purified by preparative TLC (silica gel, 0.5% $NH_4OH$/4.5% methanol/95% dichloromethane) and converted to its hydrochloride salt by the addition of hydrogen chloride (2 M solution in ethyl ether) to give 6.4 mg of a white solid (58%). ESI-MS calculated for $C_{26}H_{36}F_3N_3O_2$: 495.27; found 496 $[M+H]^+$.

EXAMPLE 93

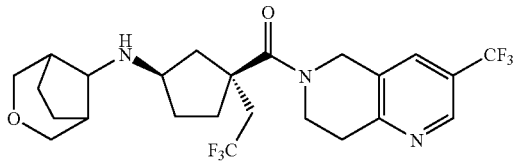

Intermediate 23 (37 mg, 0.079 mmol) was combined with Intermediate 26 (10 mg, 0.079 mmol), N,N-diisopropylethylamine (43 μL, 0.25 mmol), 4 Å powdered molecular sieves (50 mg), and sodium triacetoxyborohydride (50 mg, 0.24 mmol) in 5 mL dichloromethane. The reaction mixture was stirred at room temperature for 24 h before being filtered through celite, washed with saturated sodium bicarbonate and brine, and dried over $Na_2SO_4$, filtered and concentrated under reduced pressure. The product was purified by preparative TLC (silica gel, 0.5% $NH_4OH$/4.5% methanol/95% dichloromethane) and converted to its hydrochloride salt by the addition of hydrogen chloride (2 M solution in ethyl ether) to give 18 mg of a white solid (45%). ESI-MS calculated for $C_{24}H_{29}F_6N_3O_2$: 505.22; found 506 $[M+H]^+$.

EXAMPLE 94

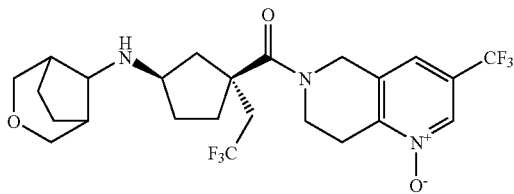

Intermediate 24 (70 mg, 0.16 mmol) was combined with Intermediate 26 (20 mg, 0.16 mmol), N,N-diisopropylethylamine (72 μL, 0.42 mmol), 4 Å powdered molecular sieves (100 mg), and sodium triacetoxyborohydride (165 mg, 0.78 mmol) in 5 mL dichloromethane. The reaction mixture was stirred at room temperature for 1.5 h and then was placed in the refrigerator over the weekend before being filtered through celite, washed with saturated sodium bicarbonate and brine, and dried over $Na_2SO_4$, filtered and concentrated under reduced pressure. The product was purified by preparative TLC (silica gel, 0.5% $NH_4OH$/4.5% methanol/95% dichloromethane) and converted to its hydrochloride salt by the addition of hydrogen chloride (2 M solution in ethyl ether) to give 24 mg of a white solid (29%). ESI-MS calculated for $C_{24}H_{29}F_6N_3O_3$: 521.21; found 522 $[M+H]^+$.

EXAMPLE 95

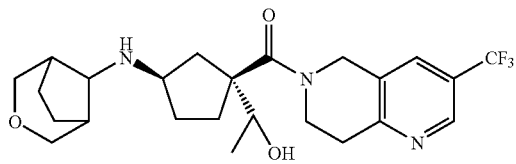

Intermediate 16 (68 mg, 0.016 mmol) was combined with Intermediate 26 (19 mg, 0.16 mmol), N,N-diisopropylethylamine (82 μL, 0.48 mmol), 4 Å powdered molecular sieves (100 mg), and sodium triacetoxyborohydride (170 mg, 0.80 mmol) in 5 mL dichloromethane. The reaction mixture was stirred at room temperature for 3 days before being filtered through celite, washed with saturated sodium bicarbonate and brine, and dried over $Na_2SO_4$, filtered and concentrated under reduced pressure. The product was purified by preparative TLC (silica gel, 0.5% $NH_4OH$/4.5% methanol/95% dichloromethane) to give 2 diastereomers. The top spot and the bottom spot where both converted to their hydrochloride salts by the addition of hydrogen chloride (2 M solution in ethyl ether) to give 17 mg and 5 mg respectively. Top Spot: ESI-MS calculated for $C_{24}H_{32}F_3N_3O_3$: 467.24; found 468 $[M+H]^+$. Bottom Spot: ESI-MS calculated for $C_{24}H_{32}F_3N_3O_3$: 467.24; found 468 $[M+H]^+$

EXAMPLE 96

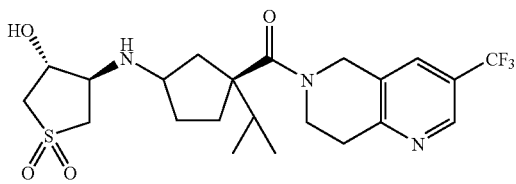

To a solution of Intermediate 27 (20 mg, 0.057 mmol) in dichloromethane (10 mL) was added (3R,4R)-4-aminotetrahydrothiophene-3-ol 1,1-dioxide (17 mg, 0.11 mmol), 4 Å powdered molecular sieves (50 mg) and sodium triacetoxyborohydride (60 mg, 0.28 mmol). The resulting reaction mixture was stirred at room temperature for 3 days before being diluted dichloromethane and washed with saturated aqueous sodium bicarbonate and brine. The organic layer was dried over sodium sulfate, filtered and concentrated under reduced pressure. The resulting crude material was purified by preparative TLC (4.5% methanol/0.5% $NH_4OH$/95% dichloromethane) to give the 2 desired single stereoisomers. Higher band: HPLC-MS calculated for $C_{22}H_{30}F_3N_3O_4S$: 489.19; found 490 $[M+H]^+$. Lower band: HPLC-MS calculated for $C_{22}H_{30}F_3N_3O_4S$: 489.19; found 490 $[M+H]^+$.

EXAMPLE 97

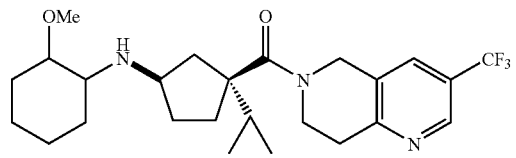

This compound was prepared as detailed in Example 1 using 2-methoxy-cyclohexanone instead of tetrahydro-4H-pyran-4-one. The four isomers on the cyclohexane ring were resolved on a preparative chiral OD column (5/95, ethanol/Hexanes). LC-MS for $C_{25}H_{36}F_3N_3O_2$ calculated: 467.28, found: 468.25 $[M+H]^+$.

EXAMPLE 98

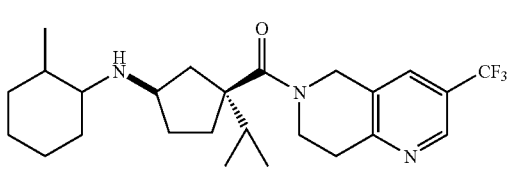

This compound was prepared as detailed in Example 1 using 2-methyl-cyclohexanone instead of tetrahydro-4H-pyran-4-one. The cis and trans racemate in respect to the cyclohexane ring were resolved on a preparative chiral AD column (2/98, ethanol/Hexanes). LC-MS for $C_{25}H_{36}F_3N_3O$ calculated: 451.28, found: 452.35 $[M+H]^+$.

EXAMPLE 99

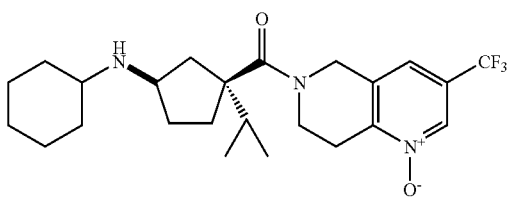

This compound was prepared as detailed in Example 30 using cyclohexanone instead of tetrahydro-4H-pyran-4-one. LC-MS for $C_{24}H_{34}F_3N_3$ calculated: 453.26, found: 454.3 $[M+H]^+$.

EXAMPLE 100

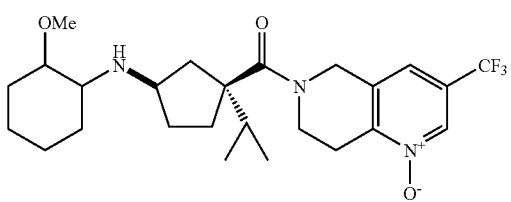

This compound was prepared as detailed in Example 30 using 2-methoxy-cyclohexanone instead of tetrahydro-4H-pyran-4-one. LC-MS for $C_{25}H_{36}F_3N_3O_3$ calculated: 4834.27, found 484.3 $[M+H]^+$.

EXAMPLE 101

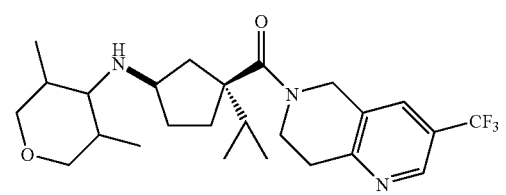

Following the procedure described for Example 12 but using Intermediate 31 instead of tetrahydro-4H-pyran-4-one afforded Example 101 as a mixture of 4 diastereomers. Chiral separation on the AD column eluting with isopropanol/heptane (8%) afforded the 4 resolved diastereomers. LC-MS for $C_{25}H_{36}F_3N_3O_2$ calculated 467.28 found 468.25 $[M+H]^+$.

EXAMPLE 102

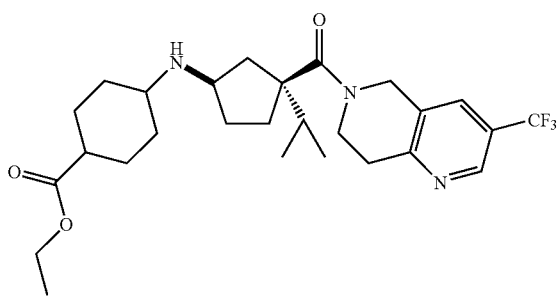

Following the procedure described for Example 12 but using ethyl 4-oxocyclohexane-1-carboxylate instead of tetrahydro-4H-pyran-4-one afforded Example 105 as mixture of 2 diastereomers. Chiral separation on the OD column eluting with ethanol/heptane (15%) afforded the 2 resolved diastereomers. LC-MS for $C_{27}H_{38}F_3N_3O_3$ calculated 509.29 found 510.4 $[M+H]^+$.

EXAMPLE 103

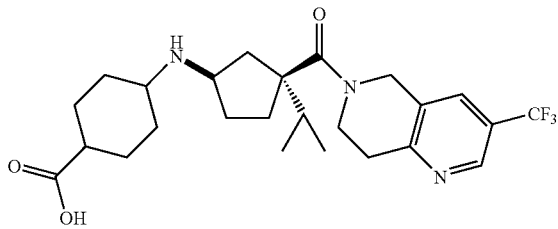

A solution of the diastereomeric esters in Example 102 (45 mg, 0.088 mmol) in methanol (1.0 mL) was treated with an aqueous solution of LiOH. H$_2$O (10 mg, 2.4 mmol) and the mixture was stirred at 50° C. overnight. The volatiles were evaporated and the product purified by reverse phase HPLC to afford Example 82. LC-MS for $C_{25}H_{34}F_3N_3O_3$ calculated 481.26 found 482.35 $[M+H]^+$.

EXAMPLE 104

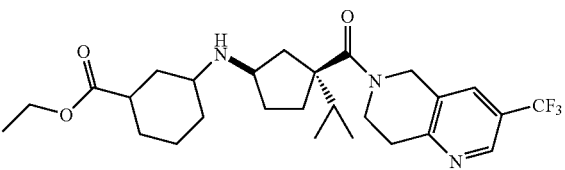

Following the procedure described for Example 12 but using ethyl 3-oxocyclohexane-1-carboxylate instead of tetrahydro-4H-pyran-4-one afforded Example 104 as mixture of 2 diastereomers. LC-MS for $C_{27}H_{38}F_3N_3O_3$ calculated 509.29 found 510.4 $[M+H]^+$.

EXAMPLE 105

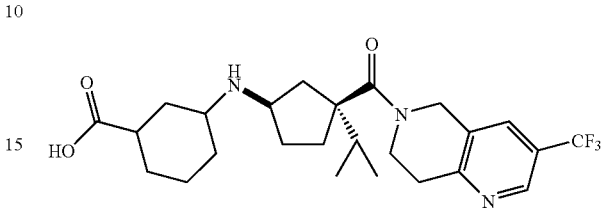

A solution of the diastereomeric esters from Example 104 (65 mg, 0.13 mmol) in methanol (1.5 mL) was treated with an aqueous solution of LiOH (20 mg, 0.48 mmol) and the mixture was stirred at 50° C. overnight. The volatiles were evaporated and the product was purified by reverse phase HPLC. LC-MS for $C_{25}H_{34}F_3N_3O_3$ calculated 481.56 found 482.5 $[M+H]^+$.

EXAMPLE 106

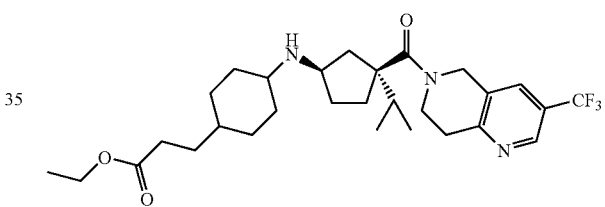

Following the procedure described for Example 12 but using ethyl 3-(4-oxocyclohexyl)propanoate instead of tetrahydro-4H-pyran-4-one afforded Example 106 as mixture of 2 diastereomers. LC-MS for $C_{29}H_{42}F_3N_3O_3$ calculated 537.32 found 538.5 $[M+H]^+$.

EXAMPLE 107

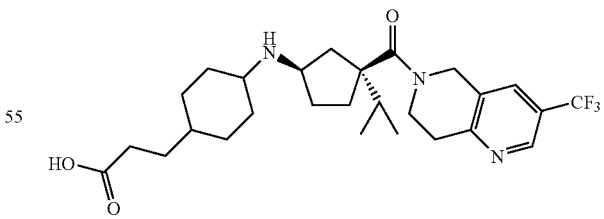

A solution of the diastereomeric esters from Example 106 (75 mg, 0.14 mmol) in methanol (1.5 mL) was treated with an aqueous solution of LiOH (25 mg, 0.60 mmol) and the mixture stirred at 50° C. overnight. The volatiles were evaporated and the product was purified by reverse phase HPLC. LC-MS for $C_{27}H_{38}F_3N_3O_3$ calculated 509.29 found 510.5 $[M+H]^+$.

EXAMPLE 108

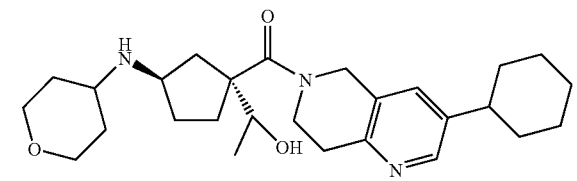

Step A

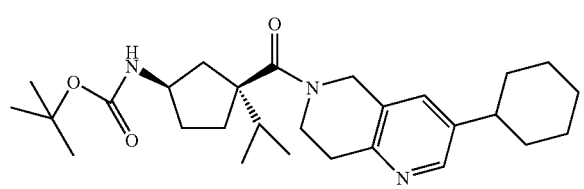

The procedure described in Step A, Intermediate 19 was followed using Intermediate 34 instead of Intermediate 8. LC-MS for $C_{28}H_{43}N_3O_3$ calculated 469.33 found 470.3 $[M+H]^+$.

Step B:

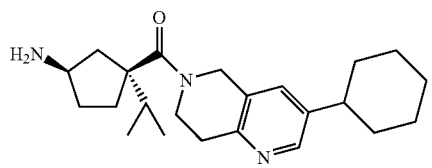

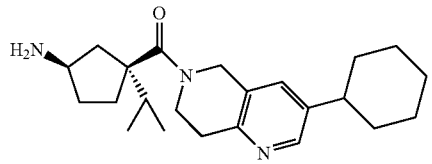

A solution of the product from Step A in ethyl acetate at 0° C. was treated with a saturated solution of HCl in ethyl acetate and the mixture was stirred for 2 h. The volatiles were evaporated in vacuo to afford the title product as a white foam. LC-MS for $C_{23}H_{35}N_3O$ calculated 369.28 found 370.5 $[M+H]^+$.

Step C:

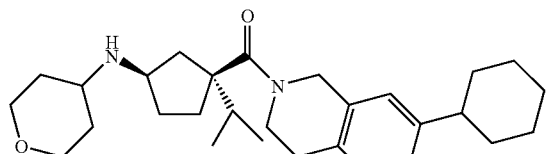

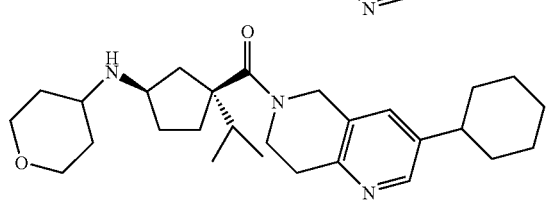

Following the procedure described for Example 12 but using the product from Step B instead of Intermediate 29 afforded Example 108. LC-MS for $C_{28}H_{43}N_3O_2$ calculated 453.34 found 454.4 $[M+H]^+$.

EXAMPLE 109

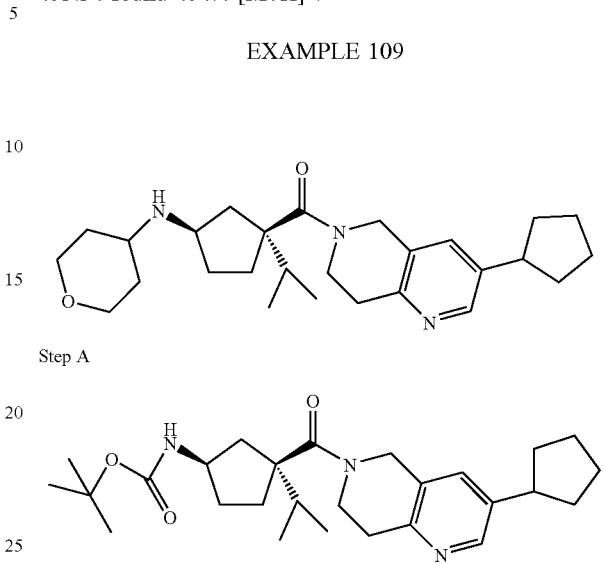

Step A

Starting from 0.235 g of Intermediate 35 and following the procedure outlined for Intermediate 19, Step A gave 0.242 g of the title compound. LC-MS for $C_{27}H_{41}N_3O_3$ calculated 455.3 found 400.3 $[M+H-56]^+$.

Step B:

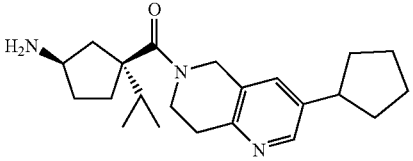

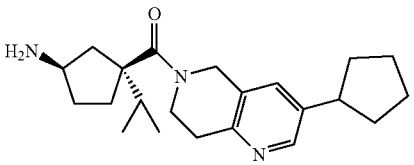

A solution of the product from Step A in ethyl acetate at 0° C. was treated with a saturated solution of HCl in ethyl acetate and the mixture was stirred for 2 h. The volatiles were evaporated in vacuo to afford 0.240 g of the title product. LC-MS for $C_{22}H_{33}N_3O$ calculated 355.2 found 356.3 $[M+H]^+$.

Step C:

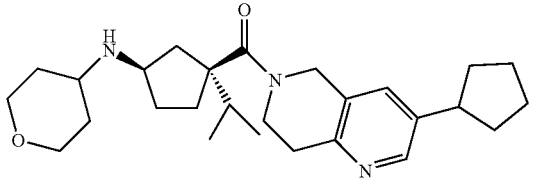

-continued

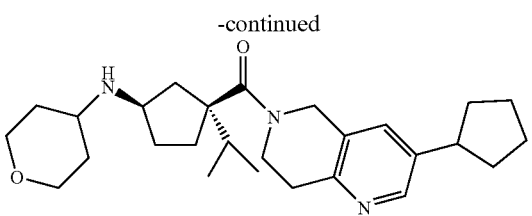

Following the procedure described for Example 12 and starting from the intermediate prepared in Step B (0.1 g, 0.2 mmol) afforded 0.1 g of Example 109 as its HCl salt. LC-MS for $C_{27}H_{41}N_3O_2$ calculated 439.3 found 440.4 $[M+H]^+$.

EXAMPLE 110

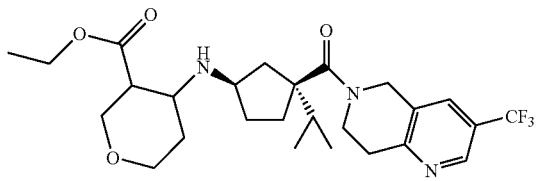

Following the procedure described for Example 12 and starting from Intermediates 19 (0.1 g, 0.2 mmol) and 32 afforded 0.0031 g of Example 110 as mixture of diastereomeric compounds HCl salts. LC-MS for $C_{26}H_{36}F_3N_3O_4$ calculated 511.2 found 512.3 $[M+H]^+$.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for treating an inflammatory or disorder or disease, which method comprises the administration to a patient of an effective amount of the compound of formula I:

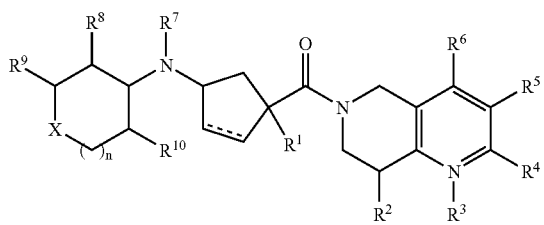

I and pharmaceutically acceptable salts thereof and individual diastereomers thereof, wherein:

wherein:
X is selected from the group consisting of:
—O—, —NR$^{20}$—, —S—, —SO—, —SO$_2$—, and —CR$^{21}$R$^{22}$—, —NSO$_2$R$^{20}$—, —NCOR$^{20}$—, —NCO$_2$R$^{20}$—, —C$^{21}$CO$_2$R$^{20}$—, —CR$^{21}$OCOR$^{20}$—, —CO—, where R$^{20}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —CO$_2$H, —CO$_2$—$C_{1-6}$ alkyl, and trifluoromethyl, where R$^{21}$ and R$^{22}$ are independently selected from: hydrogen, hydroxy, $C_{1-6}$ alkyl, —O—$C_{1-6}$alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —CO$_2$H, —CO$_2$—$C_{1-6}$ alkyl, and trifluoromethyl;

R$^1$ is selected from:
—$C_{1-6}$alkyl, —$C_{0-6}$alkyl-O—$C_{1-6}$alkyl-, —$C_{0-6}$alkyl-S—$C_{1-6}$alkyl-, —($C_{0-6}$alkyl)-($C_{3-7}$cycloalkyl)-($C_{0-6}$alkyl), hydroxy, -heterocycle, —CN, —NR$^{20}$R$^{26}$, —NHSO$_2$R$^{20}$, —NHCOR$^{20}$, —NHCO$_2$R$^{20}$, —CO$_2$R$^{20}$, —CR$^{21}$CO$_2$R$^{20}$, —CR$^{21}$OCOR$^{20}$ and phenyl, where R$^{26}$ is selected from: hydrogen, $C_{1-6}$ alkyl, benzyl, phenyl, $C_{3-6}$ cycloalkyl where the alkyl, phenyl, benzyl, and cycloalkyl groups can be unsubstituted or substituted with 1–3 substituents where the substituents are independently selected from: halo, hydroxy, $C_{1-3}$alkyl, $C_{1-3}$alkoxy, —CO$_2$H, —CO$_2$—$C_{1-6}$ alkyl, and trifluoromethyl where the alkyl and the cycloalkyl are unsubstituted or substituted with 1–7 substituents where the substituents are independently selected from:
(a) halo,
(b) hydroxy,
(c) —O—C1–3alkyl,
(d) trifluoromethyl,
(f) C1–3alkyl,
(g) —O—C1–3alkyl,
(h) —CO2R20,
(i) —SO2R20,
(j) —NHCOCH3,
(k) —NHSO2CH3,
(l) -heterocycle,
(m) =O,
(n) —CN, and where the phenyl and pyridyl are unsubstituted or substituted with 1–3 substituents where the substituents are independently selected from: halo, hydroxy, $C_{1-3}$alkyl, $C_{1-3}$alkoxy and trifluoromethyl;

R$^2$ is selected from:
(a) hydrogen,
(b) hydroxy,
(c) halo,
(d) $C_{1-3}$alkyl, where the alkyl is unsubstituted or substituted with 1–6 substituents independently selected from: fluoro, and hydroxy,
(e) —NR$^{20}$R$^{26}$,
(f) —CO$_2$R$^{20}$,
(g) —CONR$^{20}$R$^{26}$,
(h) —NR$^{20}$COR$^{21}$,
(i) —OCONR$^{20}$R$^{26}$, (j) —NR$^{20}$CONR$^{20}$R$^{26}$,
(k) -heterocycle,
(l) —CN,
(m) —NR$^{20}$—SO$_2$—NR$^{20}$R$^{26}$,
(n) —NR$^{20}$—SO$_2$—R$^{26}$,
(o) —SO$_2$—NR$^{20}$R$^{26}$, and
(p) =O, where R$^2$ is connected to the ring via a double bond;

R$^3$ is oxygen or is absent;
R$^4$ is selected from:
(a) hydrogen,
(b) C$_{1-6}$alkyl,
(c) trifluoromethyl,
(d) trifluoromethoxy,
(e) chloro,
(f) fluoro,
(g) bromo, and
(h) phenyl;

R$^5$ is selected from:
(a) C$_{1-6}$alkyl, where alkyl may be unsubstituted or substituted with 1–6 fluoro and optionally substituted with hydroxyl,
(b) —O—C$_{1-6}$alkyl, where alkyl may be unsubstituted or substituted with 1–6 fluoro,
(c) —CO—C$_{1-6}$alkyl, where alkyl may be unsubstituted or substituted with 1–6 fluoro,
(d) —S—C$_{1-6}$alkyl, where alkyl may be unsubstituted or substituted with 1–6 fluoro,
(e) -pyridyl, which may be unsubstituted or substituted with one or more substituents selected from the group consisting of: halo, trifluoromethyl, C$_{1-4}$alkyl, and CO$_2$R$^{20}$,
(f) fluoro,
(g) chloro,
(h) bromo,
(i) —C$_{4-6}$cycloalkyl,
(j) —O—C$_{4-6}$cycloalkyl,
(k) phenyl, which may be unsubstituted or substituted with one or more substituents selected from the group consisting of: halo, trifluoromethyl, C$_{1-4}$alkyl, and CO$_2$R$^{20}$,
(l) —O-phenyl, which may be unsubstituted or substituted with one or more substituents selected from the group consisting of: halo, trifluoromethyl, C$_{1-4}$alkyl, and CO$_2$R$^{20}$,
(m) —C$_{3-6}$cycloalkyl, where alkyl may be unsubstituted or substituted with 1–6 fluoro,
(n) —O—C$_{3-6}$cycloalkyl, where alkyl may be unsubstituted or substituted with 1–6 fluoro,
(o) -heterocycle,
(p) —CN, and
(q) —CO$_2$R$^{20}$;

R$^6$ is selected from:
(a) hydrogen,
(b) C1–6alkyl, and
(c) trifluoromethyl
(d) fluoro
(e) chloro, and
(f) bromo;

R$^7$ is selected from:
(a) hydrogen, and
(b) C$_{1-6}$alkyl, which is unsubstituted or substituted with 1–3 substituents where the substituents are independently selected from: halo, hydroxy, —CO$_2$H, —CO$_2$C$_{1-6}$alkyl, and —O—C$_{1-3}$alkyl;

R$^8$ is selected from:
(a) hydrogen,
(b) C$_{1-6}$alkyl, where alkyl may be unsubstituted or substituted with 1–6 substituents where the substituents are chosen from the group: fluoro, C$_{1-3}$alkoxy, hydroxy, —CO$_2$R$^{20}$,
(c) fluoro,
(d) —O—C$_{1-3}$alkyl, where alkyl may be unsubstituted or substituted with 1–3 fluoro, and
(e) C$_{3-6}$ cycloalkyl,
(f) —O—C$_{3-6}$cycloalkyl,
(g) hydroxy,
(h) —CO$_2$R$^{20}$,
(i) —OCOR$^{20}$,
or R$^7$ and R$^8$ may be joined together via a C$_{2-4}$alkyl or a C$_{0-2}$alkyl-O—C$_{1-3}$alkyl chain to form a 5–7 membered ring;

R$^9$ is selected from:
(a) hydrogen,
(b) C$_{1-6}$alkyl, where alkyl may be unsubstituted or substituted with 1–6 substituents where the substituents are chosen from the group: fluoro, C$_{1-3}$alkoxy, hydroxy, —CO$_2$R$^{20}$,
(c) CO$_2$R$^{20}$,
(d) hydroxy, and
(e) —O—C$_{1-6}$alkyl, where alkyl may be unsubstituted or substituted with 1–6 substituents where the substituents are chosen from the group: fluoro, C$_{1-3}$alkoxy, hydroxy, —CO$_2$R$^{20}$,
or R$^8$ and R$^9$ may be joined together by a C$_{1-4}$alkyl chain or a C$_{0-3}$alkyl-O—C$_{0-3}$alkyl chain to form a 3–6 membered ring;

R$^{10}$ is selected from:
(a) hydrogen, and
(b) C$_{1-6}$alkyl, where alkyl may be unsubstituted or substituted with 1–6 fluoro,
(c) fluoro,
(d) —O—C$_{3-6}$cycloalkyl, and
(e) —O—C$_{1-3}$alkyl, where alkyl may be unsubstituted or substituted with 1–6 fluoro,
or R$^8$ and R$^{10}$ may be joined together by a C$_{2-3}$alkyl chain to form a 5–6 membered ring, where the alkyl are unsubstituted or substituted with 1–3 substituents where the substiuents are independently selected from: halo, hydroxy, —CO$_2$R$^{20}$, C$_{1-3}$alkyl, and C$_{1-3}$alkoxy,
or R$^8$ and R$^{10}$ may be joined together by a C$_{1-2}$alkyl-O—C$_{1-2}$alkyl chain to form a 6–8 membered ring, where the alkyl are unsubstituted or substituted with 1–3 substituents where the substiuents are independently selected from: halo, hydroxy, —CO$_2$R$^{20}$, C$_{1-3}$alkyl, and
C$_{1-3}$alkoxy, or R$^8$ and R$^{10}$ may be joined together by a —O—C$_{1-2}$alkyl-O-chain to form a 6–7 membered ring, where the alkyl are unsubstituted or substituted with 1–3 substituents where the substiuents are independently selected from: halo, hydroxy, —CO$_2$R$^{20}$, C$_{1-3}$alkyl, and C$_{1-3}$alkoxy;

n is selected from 0, 1 and 2;
the dashed line represents a single or a double bond.

2. A method according to claim 1, wherein said disorder or disease is rheumatoid arthritis.

3. A method according to claim 1, wherein said disorder or disease is atherosclerosis.

4. A method according to claim 1, wherein said compound is of formula Ia:

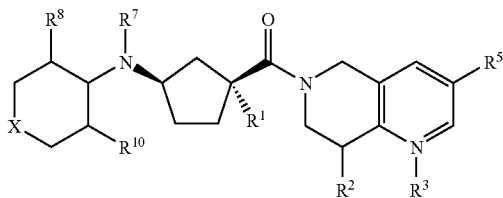

and pharmaceutically acceptable salts and individual diastereomers thereof.

5. A method according to claim 1, wherein said compound is of formula Ib:

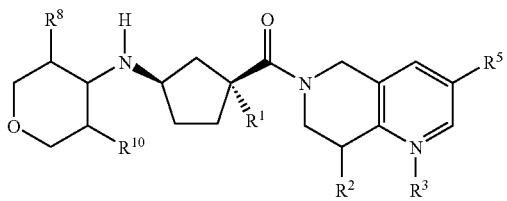

and pharmaceutically acceptable salts and individual diastereomers thereof.

6. A method according to claim 1, wherein said compound is of formula Ic:

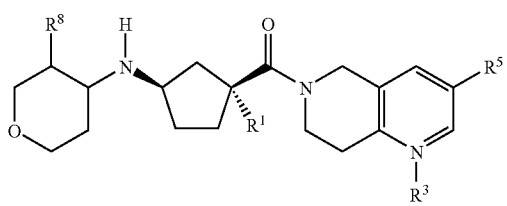

and pharmaceutically acceptable salts and individual diastereomers thereof.

7. A method according to claim 1, wherein said compound is of formula Id:

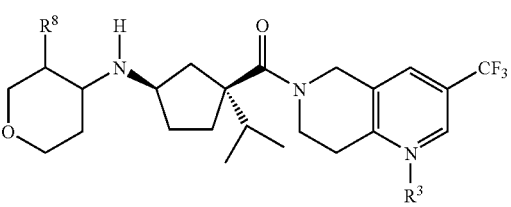

and pharmaceutically acceptable salts and individual diastereomers thereof.

8. A method according to claim 1, wherein said compound is:

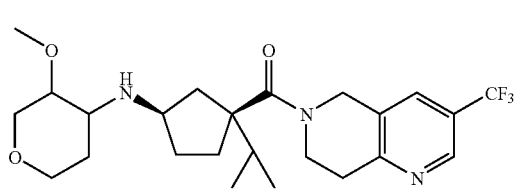

and pharmaceutically acceptable salts and individual diastereomers thereof.

9. A method according to claim 1, wherein said compound is:

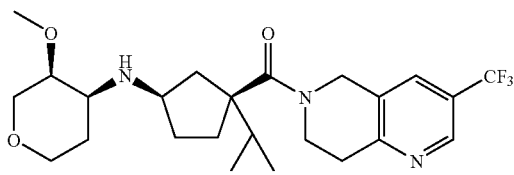

and pharmaceutically acceptable salts and individual diastereomers thereof.

10. A method according to claim 1, wherein said compound is a salt of a compound having the structure:

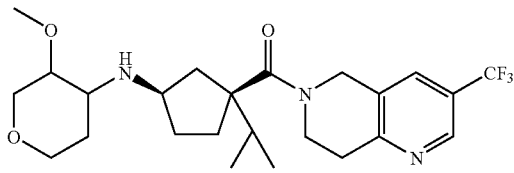

wherein said salt is derived from an acid selected from hydrochloric, hydrobromic, sulfuric, sulfamic, phosphoric, nitric, acetic, propionic, succinic, glycolic, stearic, lactic, malic, tartaric, citric, ascorbic, pamoic, maleic hydroxymaleic, phenylacetic, glutamic, benzoic, salicylic, sulfanillic, 2-acetoxybenzoic, fumaric, toluenesulfonic, methanesulfonic, ethane disulfonic, oxalic, and isethionic.

11. A method according to claim 1, wherein said compound is a salt of a compound having the structure:

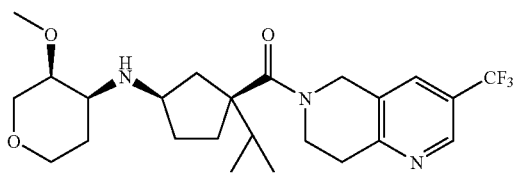

wherein said salt is derived from an acid selected from hydrochloric, hydrobromic, sulfuric, sulfamic, phosphoric, nitric, acetic, propionic, succinic, glycolic, stearic, lactic, malic, tartaric, citric, ascorbic, pamoic, maleic hydroxymaleic, phenylacetic, glutamic, benzoic, salicylic, sulfanillic, 2-acetoxybenzoic, fumaric, toluenesulfonic, methanesulfonic, ethane disulfonic, oxalic, and isethionic.

12. A method for modulation of chemokine receptor activity in a mammal which comprises the administration of an effective amount of the compound of formula I:

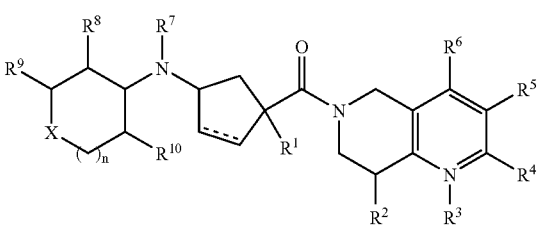

and pharmaceutically acceptable salts thereof and individual diastereomers thereof, wherein:

wherein:
X is selected from the group consisting of:
—O—, —NR$^{20}$—, —S—, —SO—, —S$_2$—, and —CR$^{21}$R$^{22}$—, —NSO$_2$R$^{20}$—, —NCOR$^{20}$—, —NCO$_2$R$^{20}$—, —CR$^{21}$CO$_2$R$^{20}$—, —CR$^{21}$OCOR$^{20}$—, —CO—, where R$^{20}$ is selected from: hydrogen, C$_{1-6}$ alkyl, benzyl, phenyl, C$_{3-6}$ cycloalkyl where the alkyl, phenyl, benzyl, and cycloalkyl groups can be unsubstituted or substituted with 1–3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl, where R$^{21}$ and R$^{22}$ are independently selected from: hydrogen, hydroxy, —C$_{1-6}$ alkyl, —O—C$_{1-6}$alkyl, benzyl, phenyl, C$_{3-6}$ cycloalkyl where the alkyl, phenyl, benzyl, and cycloalkyl groups can be unsubstituted or substituted with 1–3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl;

R$^1$ is selected from:
—C$_{1-6}$alkyl, —C$_{0-6}$alkyl-O—C$_{1-6}$alkyl-, —C$_{0-6}$alkyl-S—C$_{1-6}$alkyl-, —(C$_{0-6}$alkyl)-(C$_{3-7}$cycloalkyl)-(C$_{0-6}$alkyl), hydroxy, -heterocycle, —CN, —NR$^{20}$R$^{26}$, —NHSO$_2$R$^{20}$, —NHCOR$^{20}$, —NHCO$_2$R$^{20}$, —CO$_2$R$^{20}$, —CR$^{21}$CO$_2$R$^{20}$, —CR$^{21}$OCOR$^{20}$ and phenyl, where R$^{26}$ is selected from: hydrogen, C$_{1-6}$ alkyl, benzyl, phenyl, C$_{3-6}$ cycloalkyl where the alkyl, phenyl, benzyl, and cycloalkyl groups can be unsubstituted or substituted with 1–3 substituents where the substituents are independently selected from: halo, hydroxy, C$_{1-3}$alkyl, C$_{1-3}$alkoxy, —CO$_2$H, —CO$_2$—C$_{1-6}$ alkyl, and trifluoromethyl where the alkyl and the cycloalkyl are unsubstituted or substituted with 1–7 substituents where the substituents are independently selected from:
(a) halo,
(b) hydroxy,
(c) —O—C1–3alkyl,
(d) trifluoromethyl,
(f) C1–3alkyl,
(g) —O—C1–3alkyl,
(h) —CO2R20,
(i) —SO2R20,
(j) —NHCOCH3,
(k) —NHSO2CH3,
(l) -heterocycle,
(m) =O,
(n) —CN, and where the phenyl and pyridyl are unsubstituted or substituted with 1–3 substituents where the substituents are independently selected from: halo, hydroxy, C$_{1-3}$alkyl, C$_{1-3}$alkoxy and trifluoromethyl;

R$^2$ is selected from:
(a) hydrogen,
(b) hydroxy,
(c) halo,
(d) C$_{1-3}$alkyl, where the alkyl is unsubstituted or substituted with 1–6 substituents independently selected from: fluoro, and hydroxy,
(e) —NR$^{20}$R$^{26}$,
(f) —CO$_2$R$^{20}$,
(g) —CONR$^{20}$R$^{26}$,
(h) —NR$^{20}$COR$^{21}$,
(i) —OCONR$^{20}$R$^{26}$,
(j) —NR$^{20}$CONR$^{20}$R$^{26}$,
(k) -heterocycle,
(l) —CN,
(m) —NR$^{20}$—SO$_2$—NR$^{20}$R$^{26}$,
(n) —NR$^{20}$—SO$_2$—R$^{26}$,
(o) —SO$_2$—NR$^{20}$R$^{26}$, and
(p) =O, where R$^2$ is connected to the ring via a double bond;

R$^3$ is oxygen or is absent;

R$^4$ is selected from:
(a) hydrogen,
(b) C$_{1-6}$alkyl,
(c) trifluoromethyl,
(d) trifluoromethoxy,
(e) chloro,
(f) fluoro,
(g) bromo, and
(h) phenyl;

R$^5$ is selected from:
(a) C$_{1-6}$alkyl, where alkyl may be unsubstituted or substituted with 1–6 fluoro and optionally substituted with hydroxyl,
(b) —O—C$_{1-6}$alkyl, where alkyl may be unsubstituted or substituted with 1–6 fluoro,
(c) —CO—C$_{1-6}$alkyl, where alkyl may be unsubstituted or substituted with 1–6 fluoro,
(d) —S—C$_{1-6}$alkyl, where alkyl may be unsubstituted or substituted with 1–6 fluoro,
(e) -pyridyl, which may be unsubstituted or substituted with one or more substituents selected from the group consisting of: halo, trifluoromethyl, C$_{1-4}$alkyl, and CO$_2$R$^{20}$,
(f) fluoro,
(g) chloro,
(h) bromo,
(i) —C$_{4-6}$cycloalkyl,
(j) —O—C$_{4-6}$cycloalkyl,
(k) phenyl, which may be unsubstituted or substituted with one or more substituents selected from the group consisting of: halo, trifluoromethyl, C$_{1-4}$alkyl, and CO$_2$R$^{20}$,
(l) —O-phenyl, which may be unsubstituted or substituted with one or more substituents selected from the group consisting of: halo, trifluoromethyl, C$_{1-4}$alkyl, and CO$_2$R$^{20}$,
(m) —C$_{3-6}$cycloalkyl, where alkyl may be unsubstituted or substituted with 1–6 fluoro,
(n) —O—C$_{3-6}$cycloalkyl, where alkyl may be unsubstituted or substituted with 1–6 fluoro,
(o) -heterocycle,
(p) —CN, and
(q) —CO$_2$R$^{20}$;

R$^6$ is selected from:
(a) hydrogen,
(b) C1–6alkyl, and
(c) trifluoromethyl
(d) fluoro
(e) chloro, and
(f) bromo;

R$^7$ is selected from:
(a) hydrogen, and
(b) C$_{1-6}$alkyl, which is unsubstituted or substituted with 1–3 substituents where the substituents are independently selected from: halo, hydroxy, —CO$_2$H, —CO$_2$C$_{1-6}$alkyl, and —O—C$_{1-3}$alkyl;

$R^8$ is selected from:
  (a) hydrogen,
  (b) $C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
  (c) fluoro,
  (d) —O—$C_{1-3}$alkyl, where alkyl may be unsubstituted or substituted with 1–3 fluoro, and
  (e) $C_{3-6}$ cycloalkyl,
  (f) —O—$C_{3-6}$cycloalkyl,
  (g) hydroxy,
  (h) —$CO_2R^{20}$,
  (i) —$OCOR^{20}$,
  or $R^7$ and $R^8$ may be joined together via a $C_{2-4}$alkyl or a $C_{0-2}$alkyl-O—$C_{1-3}$alkyl chain to form a 5–7 membered ring;

$R^9$ is selected from:
  (a) hydrogen,
  (b) $C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
  (c) $CO_2R^{20}$,
  (d) hydroxy, and
  (e) —O—$C_{1-6}$alkyl, where alkyl may be unsubstituted or substituted with 1–6 substituents where the substituents are chosen from the group: fluoro, $C_{1-3}$alkoxy, hydroxy, —$CO_2R^{20}$,
  or $R^8$ and $R^9$ may be joined together by a $C_{1-4}$alkyl chain or a $C_{0-3}$alkyl-O—$C_{0-3}$alkyl chain to form a 3–6 membered ring;

$R^{10}$ is selected from:
  (a) hydrogen, and
  (b) $C_{1-6}$alkyl, where alkyl may be unsubstituted or substituted with 1–6 fluoro,
  (c) fluoro,
  (d) —O—$C_{3-6}$cycloalkyl, and
  (e) —O—$C_{1-3}$alkyl, where alkyl may be unsubstituted or substituted with 1–6 fluoro,
  or $R^8$ and $R^{10}$ may be joined together by a $C_{2-3}$alkyl chain to form a 5–6 membered ring, where the alkyl are unsubstituted or substituted with 1–3 substituents where the substiuents are independently selected from: halo, hydroxy, —$CO_2R^{20}$, $C_{1-3}$alkyl, and $C_{1-3}$alkoxy,
  or $R^8$ and $R^{10}$ may be joined together by a $C_{1-2}$alkyl-O—$C_{1-2}$alkyl chain to form a 6–8 membered ring, where the alkyl are unsubstituted or substituted with 1–3 substituents where the substiuents are independently selected from: halo, hydroxy, —$CO_2R^{20}$, $C_{1-3}$alkyl, and
  $C_{1-3}$alkoxy, or $R^8$ and $R^{10}$ may be joined together by a —O—$C_{1-2}$alkyl chain to form a 6–7 membered ring, where the alkyl are unsubstituted or substituted with 1–3 substituents where the substiuents are independently selected from: halo, hydroxy, —$CO_2R^{20}$, $C_{1-3}$alkyl, and $C_{1-3}$alkoxy;

n is selected from 0, 1 and 2;
the dashed line represents a single or a double bond.

* * * * *